United States Patent
Seayad et al.

(10) Patent No.: US 11,999,821 B2
(45) Date of Patent: Jun. 4, 2024

(54) COMPOUND, A REACTION PRODUCT OF SAID COMPOUND AND PRODUCTION METHODS THEREOF

(71) Applicant: AGENCY FOR SCIENCE, TECHNOLOGY AND RESEARCH, Singapore (SG)

(72) Inventors: Jayasree Seayad, Singapore (SG); Satyasankar Jana, Singapore (SG); Abdul Majeed Seayad, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 847 days.

(21) Appl. No.: 17/043,437

(22) PCT Filed: Mar. 29, 2019

(86) PCT No.: PCT/SG2019/050185
§ 371 (c)(1),
(2) Date: Sep. 29, 2020

(87) PCT Pub. No.: WO2019/190409
PCT Pub. Date: Oct. 3, 2019

(65) Prior Publication Data
US 2021/0053953 A1     Feb. 25, 2021

(30) Foreign Application Priority Data

Mar. 29, 2018  (SG) .............................. 10201802688T
Mar. 29, 2018  (SG) .............................. 10201802689R

(51) Int. Cl.
| C07D 407/14 | (2006.01) |
| C07D 405/14 | (2006.01) |
| C08F 283/00 | (2006.01) |
| C08G 71/04  | (2006.01) |
| C09D 175/12 | (2006.01) |

(52) U.S. Cl.
CPC ........... *C08G 71/04* (2013.01); *C07D 405/14* (2013.01); *C07D 407/14* (2013.01); *C08F 283/00* (2013.01); *C09D 175/12* (2013.01)

(58) Field of Classification Search
CPC ... C07D 407/14; C07D 405/14; C08F 283/00; C08G 71/04
See application file for complete search history.

(56) References Cited

U.S. PATENT DOCUMENTS

| 3,624,016 A | 11/1971 | Lew |
| 3,663,569 A | 5/1972 | Lew |
| 2012/0259087 A1 | 10/2012 | Cramail et al. |
| 2015/0247004 A1 | 9/2015 | Lombardo et al. |

FOREIGN PATENT DOCUMENTS

| CN | 105348071 A | 2/2016 |
| EP | 2679644 A1 | 1/2014 |
| EP | 3018163 A1 | 5/2016 |
| EP | 3536730 A1 | 9/2019 |
| EP | 3569597 A1 | 11/2019 |
| GB | 1293818 A | 10/1972 |
| JP | 2012172144 A | 9/2012 |
| JP | 2015074612 A | 4/2015 |
| JP | 2016033638 A | 3/2016 |
| JP | 2016194029 A | 11/2016 |
| WO | 2013028292 A1 | 2/2013 |
| WO | 2018183523 A1 | 10/2018 |

OTHER PUBLICATIONS

He, Polymers 2017, vol. 9 p. 649 (Year: 2017).*
Zhang et al., RSC Adv. 2007, vol. 7, lines 37-46 (Year: 2007).*
European Extended Search Report dated Dec. 2, 2021 for European Application No. 19775193.6.
Beniah et al: "Novel thermoplastic polyhydroxyurethane elastomers as effective damping materials over broad temperature ranges" European Polymer Journal, Pergamon Press Ltd Oxford, vol. 84, pp. 770-783 XP029832418, Jun. 2, 2016.
Leitsch et al: "Nonisocyanate Thermoplastic Polyhydroxyurethane Elastomers via Cyclic Carbonate Aminolysis: Critical Role of Hydroxyl Groups in Controlling Nanophase Separation" ACS Macro Letters, vol. 5, No. 4, pp. 424-429 XP055862262, Apr. 19, 2016.
Leitsch et al: "Supplementary Information Non-Isocyanate Thermoplastic Polyhydroxyurethane Elastomers vvia Cyclic Carbonate Aminolysis: Critical Role of Hydroxyl Groups in Controlling Nanophase Separation" ACS Macro Letters, pp. 1-30 XP55862270, Mar. 9, 2016.
Nobuhiro et al: "Synthesis and properties of poly(hydroxyurethane)s" Journal of Polymer Science Part A: Polymer Chemistry, John Wiley & Sons, Inc., US, vol. 31, No. 11, pp. 2765-2773 XP002599514, Oct. 1, 1993.
Prompers et al: "Polyurethanes with pendant hydroxy groups: Polycondensation of D-mannitol-1,2:5,6-dicarbonate with diamines" Designed Monomers and Polymers, VSP, Utrecht, vol. 8, No. 6, pp. 547-569 XP008155657, Apr. 2, 2012.

(Continued)

*Primary Examiner* — Robert D Harlan
(74) *Attorney, Agent, or Firm* — EIP US LLP; Jared A. Barnard

(57) ABSTRACT

There is provided a compound represented by general formula (Ib), wherein ring A is a carbocyclic or heterocyclic ring, a reaction product of the reaction between one or more said compounds and one or more amine containing compounds. Also provided is related production methods thereof.

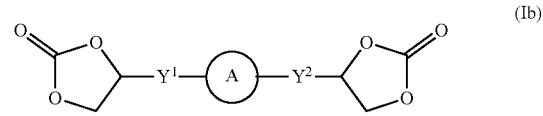

17 Claims, 9 Drawing Sheets

(56) References Cited

OTHER PUBLICATIONS

Fache et al: "Vanillin, a promising biobased building-block for monomer synthesis" Green Chemistry, vol. 16, No. 1, pp. 1987-1998 XP055502535, Feb. 18, 2014.

Schmidt et al: "Isocyanate-Free Route to Poly(carbohydrate-urethane) Thermosets and 100% Bio-Based Coatings Derived from Glycerol Feedstock" Macromolecules, vol. 49, No. 19, pp. 7268-7276 XP055420495, Oct. 11, 2016.

Martinez et al: "An Efficient and Versatile Lanthanum Heterscorpionate Catalyst for Carbon Dioxide Fixation into Cyxlic Carbonates" Chemsuschem, vol. 10, No. 14, pp. 2886-2890 XP055862285, Jun. 28, 2017.

Dabral et al: "Silver-Catalyzed Carboxylative Cyclization of Primary Propargyl Alcohols with CO2" Oraginc Letters, vol. 21, No. 5, pp. 1422-1425 XP055692235, Feb. 20, 2019.

Komura et al: "Synthetic Studies by the Use of Carbonates, II. An Easy Method of Preparing Cyclic Carbonates of Polyhydroxy Compounds by Transesterification with Ethylene Carbonate", Bulletin of HE Chemical Society of Japan, XP055180220, Jan. 1, 1973.

Hough et al: "363. Carbohydrate carbonates. Part II. Their preparation by ester-exchange methods" Journal of the Chemical Society (Resumed), p. 1934 XP055180229, Jan. 1, 1962.

International Search Report and Written Opinion dated Jun. 14, 2019 for PCT Application No. PCT/SG2019/050185.

International Preliminary Report on Patentability dated Sep. 29, 2020 for PCT Application No. PCT/SG2019/050185.

Zhang et al., "A novel 2,5-furandicarboxylic acid-based bis(cyclic carbonate) for the synthesis of biobased non-socyanate polyurethanes", RSC Adv., Dec. 22, 2017, vol. 7, No. 1, pp. 37-46, DOI: 10.1039/C6RA25045A.

Database Registry, Chemical Abstract Services, STN Accession No. 2099047-05-7. Jun. 26, 2017.

Database Registry, Chemical Abstract Services, STN Accession No. 23886-94-4, 23886-93-3. Nov. 16, 1984.

Beniah et al., "Functionalization of Hydroxyl Groups in Segmented Polyhydroxyurethane Eliminates Nanophase Separation", Journal of Polymer Science, Part A: Polymer Chemistry, Jul. 27, 2017, vol. 55, pp. 3347-3351.

Dolci, et al., "Thermoresponsive crosslinked isocyanate-free polyurethanes by Diels-Alder polymerization" J. Appl. Polym. Sci., Sep. 26, 2016, vol. 134, No. 5, pp. 44408 (1-11), DOI: 10.1002/APP. 44408.

He et al., Synthesis and Characterization of Dimmer-Acid-Based Nonisocyanate Polyurethane and Epoxy Resin Composite. Polymers, Nov. 28, 2017, vol. 9, No. 12, pp. 649 (1-12), DOI: 10.3390/POLYM9120649.

* cited by examiner

COMPOUND, A REACTION PRODUCT OF SAID COMPOUND AND PRODUCTION METHODS THEREOF

CROSS-REFERENCE TO RELATED APPLICATIONS

This application is a 371 of International Application No. PCT/SG2019/050185, filed Mar. 29, 2019, which claims priority to Singapore Application No. 10201802688T, filed Mar. 29, 2018 and 10201802689R filed Mar. 29, 2018, under 35 U.S.C. § 119(a). Each of the above-referenced patent applications is incorporated by reference in its entirety.

Various embodiments disclosed herein relate broadly to a compound, a reaction product of said compound, and related production methods thereof.

BACKGROUND

The global polyurethane market is growing rapidly due to the increase in demand for polyurethane in several applications such as in the manufacture of rigid and flexible foams, coatings, adhesives, sealants, elastomers and consumer & personal care products etc.

Traditional polyurethanes (PU) are synthesized by the reaction of di-functional or poly-functional hydroxyl compounds (HO—R—OH or —R—(OH)$_n$) with di-functional or poly-functional isocyanate compounds (O=C=N—R—N=C=O or —R—(N=C=O)$_n$), optionally in the presence of catalysts. However, such currently used production methods are faced with several drawbacks.

Firstly, isocyanates are moisture sensitive, necessitating stringent precautions for transportation, handling and storage.

Next, isocyanates and their predecessor compound, i.e. phosgene are highly toxic compounds and are considered chemical irritants. Some of the isocyanates have also been classified as potential human carcinogens. Using such toxic components in the current methods of synthesizing polyurethanes is potentially dangerous as they are hazardous to human health and also detrimental to the environment. As exposure to these toxic components can cause adverse health effects, the cost of production for such methods are high as implementation of safety measures and protocols are necessary to protect workers during the manufacturing process. New governmental regulations to limit the use of toxic chemicals also compound to the challenges faced by traditional methods of PU synthesis. Despite industries being actively involved in developing alternatives, synthesizing a suitable PU remains a challenge.

In view of the above, there is thus a need to address or at least ameliorate one of the problems described above.

SUMMARY

In one aspect, there is provided a compound represented by general formula (Ib):

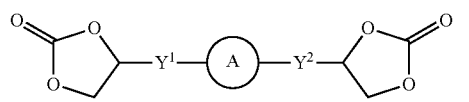

(Ib)

wherein
ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;
$Y^1$ and $Y^2$ are each independently selected from the group consisting of:
a single bond,
—Z—O—Z—,
—Z—NR$^b$—Z—,
—Z—O—C(=O)—Z—, —Z—C(=O)—O—Z—,
—Z—NR$^b$—C(=O)—Z—, —Z—C(=O)—NR$^b$—Z—,
—Z—NR$^b$—C(=O)—O—Z—, —Z—O—C(=O)—NR$^b$—Z—;
where each Z is independently selected from the group consisting of a single bond, optionally substituted saturated aliphatic chain and optionally substituted unsaturated aliphatic chain;
where R$^b$ is H or C$_1$-C$_6$ alkyl, and
with the proviso that when ring A is 1,4-phenylene, $Y^1$ is not —(CH$_2$)—O—C(=O)— and $Y^2$ is not —C(=O)—O—(CH$_2$)—.

In one embodiment, ring A is selected from the group consisting of benzene, furan, thiophene, pyrrole, oxazole, isoxazole, isothiazole, tetrahydrofuran, tetrahydrothiophene, pyrrolidine, pyridine, pyrone, pyridazine, pyrimidine, pyrazine, triazine, piperidine and piperazine.

In one embodiment, ring A is selected from any one of the general formulae (II) to (V):

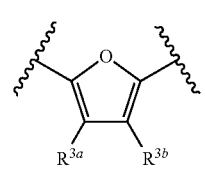

(II)

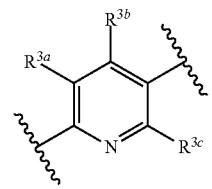

(III)

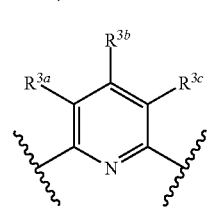

(IV)

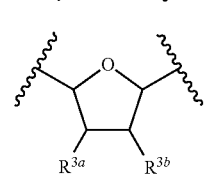

(V)

wherein
$R^{3a}$, $R^{3b}$ and $R^{3c}$ are each independently selected from the group consisting of a hydrogen, hydroxy, halogen, cyano, amino, nitro, carboxyl, alkyl, alkenyl, alkynyl, alkoxy, haloalkyl, haloalkoxy, cycloalkyl, cycloalkenyl, alkylcarbonyl and alkoxycarbonyl.

In one embodiment, $Y^1$ is selected from the group consisting of —Z—O—Z— and —Z—O—C(=O)—Z—; $Y^2$ is selected from the group consisting of —Z—O—Z— and —Z—C(=O)—O—Z—; each Z is independently selected from the group consisting of a single bond and $C_1$-$C_6$ alkyl.

In one embodiment, the compound is selected from the following:

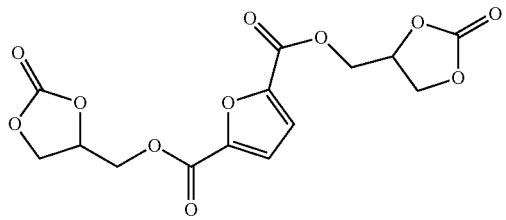 [SMILES: O=C1OCC(COC(=O)c2ccc(C(=O)OCC3COC(=O)O3)o2)O1]

bis((2-oxo-1,3-dioxolan-4-yl)methyl)furan-2,5-dicarboxylate (FBC-1);

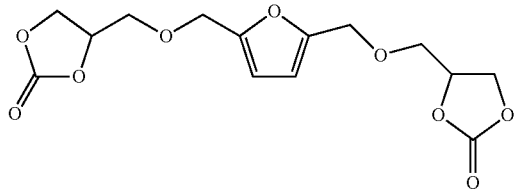 [SMILES: O=C1OCC(COCc2ccc(COCC3COC(=O)O3)o2)O1]

4,4'-(((furan-2,5-diylbis(methylene))bis(oxy))bis(methylene))bis(1,3-dioxolan-2-one) (FBC-2);

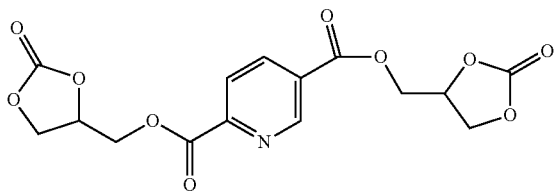 [SMILES: O=C1OCC(COC(=O)c2ccc(C(=O)OCC3COC(=O)O3)nc2)O1]

bis((2-oxo-1,3-dioxolan-4-yl)methyl)pyridine-2,5-dicarboxylate (PBC);

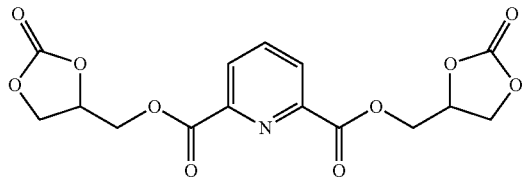 [SMILES: O=C1OCC(COC(=O)c2cccc(C(=O)OCC3COC(=O)O3)n2)O1]

bis((2-oxo-1,3-dioxolan-4-yl)methyl)pyridine-2,6-dicarboxylate (PBC-2); and

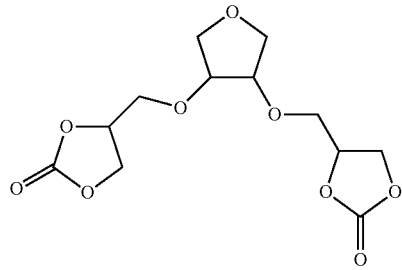 [SMILES: O=C1OCC(COC2COCC2OCC2COC(=O)O2)O1]

4,4'-(((tetrahydrofuran-3,4-diyl)bis(oxy))bis(methylene))bis(1,3-dioxolan-2-one) (HFBC).

In one aspect, there is provided a method of preparing the compound as disclosed herein, the method comprising:
converting a precursor compound represented by general formula (VI) to the compound as disclosed herein through one or more chemical reactions:

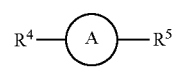 (VI)

wherein
ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;
$R^4$ and $R^5$ are each independently selected from the group consisting of —OH, —C(=O)H, —C(=O)—OH, —NR$^c$R$^d$, —C(=O)—NR$^c$R$^d$, —($C_1$-$C_6$ alkyl)-OH, —($C_1$-$C_6$ alkyl)-C(=O)H, —($C_1$-$C_6$ alkyl)-C(=O)—OH, —($C_1$-$C_6$ alkyl)-NR$^c$R$^d$ and —($C_1$-$C_6$ alkyl)-C(=O)—NR$^c$R$^d$,
where R$^c$ and R$^d$ are independently selected from the group consisting of H or $C_1$-$C_6$ alkyl,
wherein at least one of the one or more chemical reactions is carried out in the presence of a halogenated compound.

In one embodiment, ring A is selected from the group consisting of disubstituted benzene, disubstituted furan, disubstituted thiophene, disubstituted pyrrole, disubstituted oxazole, disubstituted isoxazole, disubstituted isothiazole, disubstituted tetrahydrofuran, disubstituted tetrahydrothiophene, disubstituted pyrrolidine, disubstituted pyridine, disubstituted pyrone, disubstituted pyridazine, disubstituted pyrimidine, disubstituted pyrazine, disubstituted triazine, disubstituted piperidine and disubstituted piperazine.

In one embodiment, the precursor compound is selected from the group consisting of 5-hydroxymethylfurfural (HMF), furan-2,5-diyldimethanol (FDM), furan-2,5-dicarboxylic acid (FDCA), furan-2,5-diyldimethanamine (FBA), pyridine-2,5-dicarboxylic acid, pyridine-2,6-dicarboxylic acid and 1,4-anhydroerythritol.

In one aspect, there is provided a reaction product of the reaction between one or more compounds as disclosed herein and one or more amine containing compounds, the reaction product having hydroxyl groups and urethane/carbamate linkages.

In one embodiment, the reaction product is a polymer having a repeating unit represented by general formula (VIIb) or a derivative thereof:

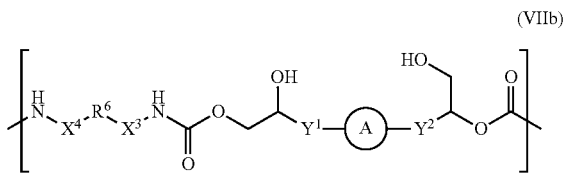

(VIIb)

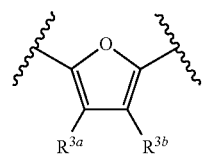

(II)

wherein ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;

$Y^1$ and $Y^2$ are each independently selected from the group consisting of: a single bond,

—Z—O—Z—,

—Z—NR$^b$—Z—,

—Z—O—C(=O)—Z—, —Z—C(=O)—O—Z—,

—Z—NR$^b$—C(=O)—Z—, —Z—C(=O)—NR$^b$—Z—,

—Z—NR$^b$—C(=O)—O—Z—, —Z—O—C(=O)—NR$^b$—Z—;

where each Z is independently selected from the group consisting of a single bond, optionally substituted saturated aliphatic chain and optionally substituted unsaturated aliphatic chain;

where $R^b$ is H or $C_1$-$C_6$ alkyl;

$R^6$ is selected from the group consisting of optionally substituted alkyl, optionally substituted alkenyl, optionally substituted alkynyl, optionally substituted polyether, optionally substituted 5-membered or 6-membered hydrocarbon cyclic ring and an optionally substituted 5-membered or 6-membered heterocyclic ring having up to three heteroatoms independently selected from the group consisting of O and S;

$X^3$ and $X^4$ are each independently selected from the group consisting of a single bond and —($C_1$-$C_6$ alkyl); and with the proviso that when ring A is 1,4-phenylene, $Y^1$ is not —(CH$_2$)—O—C(=O)— and $Y^2$ is not —C(=O)—O—(CH$_2$)—.

In one embodiment, ring A is selected from the group consisting of benzene, furan, thiophene, pyrrole, oxazole, isoxazole, isothiazole, tetrahydrofuran, tetrahydrothiophene, pyrrolidine, pyridine, pyrone, pyridazine, pyrimidine, pyrazine, triazine, piperidine and piperazine.

In on embodiment, ring A is selected from any one of the general formulae (II) to (V):

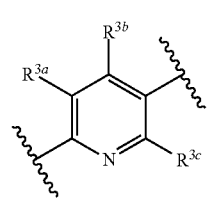

(III)

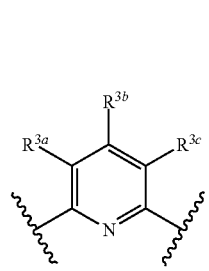

(IV)

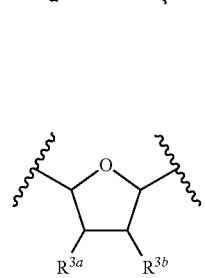

(V)

wherein $R^{3a}$, $R^{3b}$ and $R^{3c}$ are each independently selected from the group consisting of a hydrogen, hydroxy, halogen, cyano, amino, nitro, carboxyl, alkyl, alkenyl, alkynyl, alkoxy, haloalkyl, haloalkoxy, cycloalkyl, cycloalkenyl, alkylcarbonyl and alkoxycarbonyl.

In one embodiment, $Y^1$ is selected from the group consisting of —Z—O—Z— and —Z—O—C(=O)—Z—; $Y^2$ is selected from the group consisting of —Z—O—Z— and —Z—C(=O)—O—Z—; each Z is independently selected from the group consisting of a single bond and $C_1$-$C_6$ alkyl.

In one embodiment, the reaction product is selected from the following:

(1)

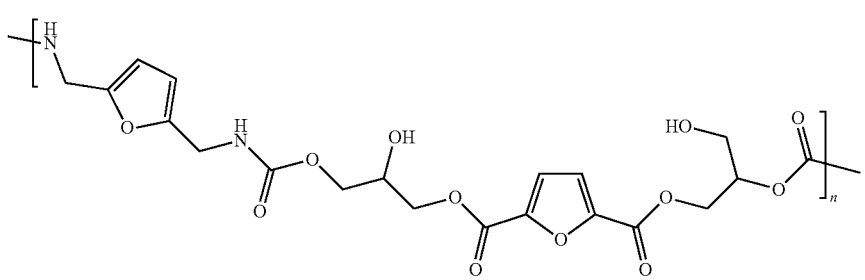

-continued
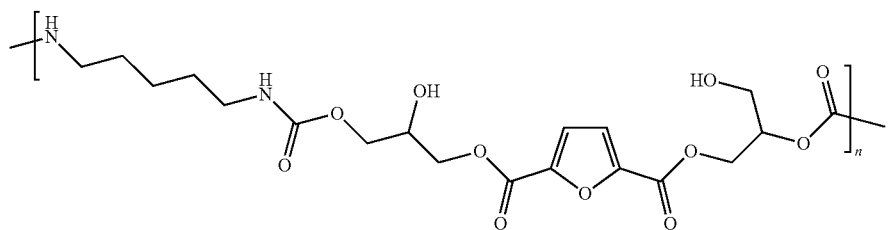
(2)
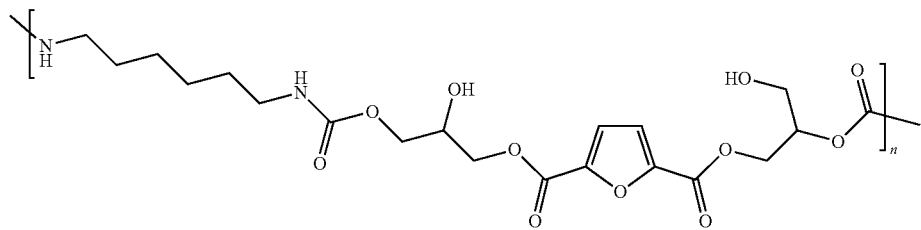
(3)
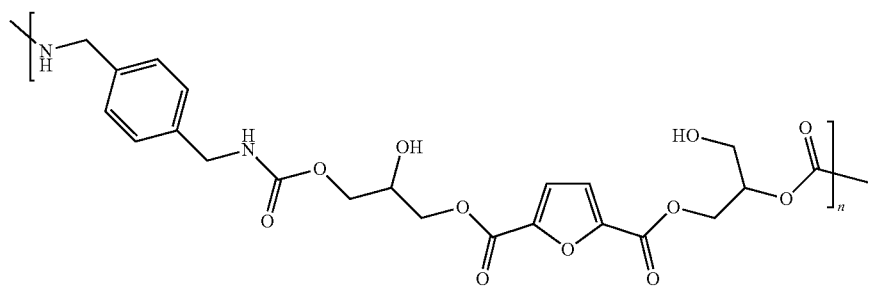
(4)
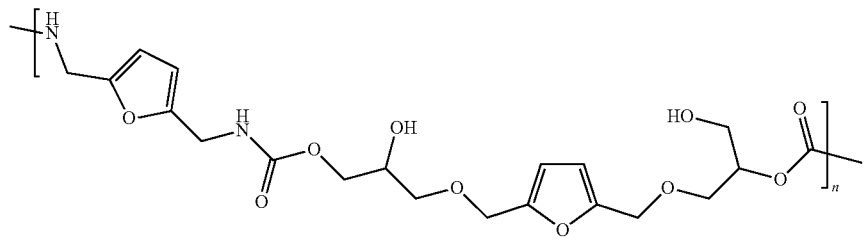
(5)
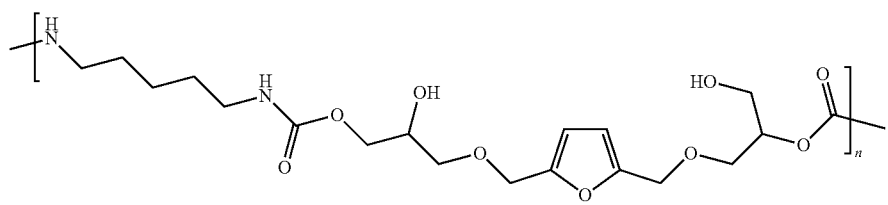
(6)
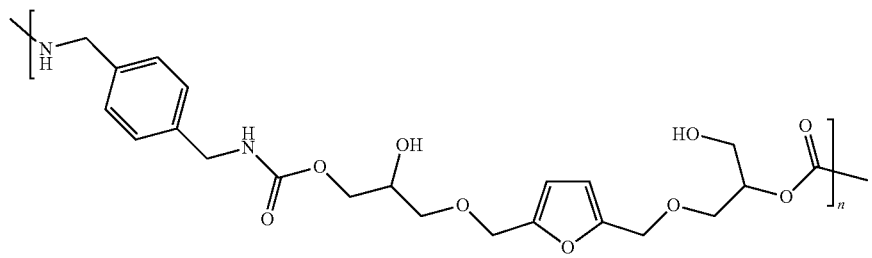
(7)

-continued
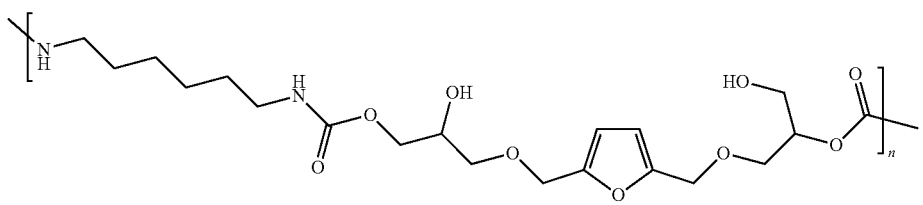
(8)
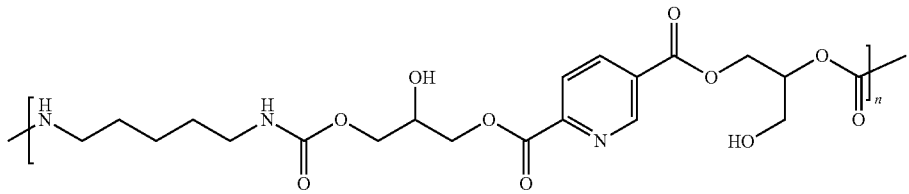
(9)
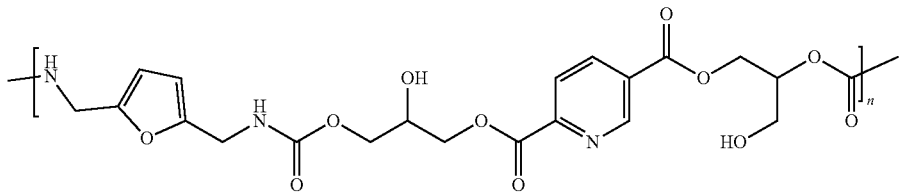
(10)
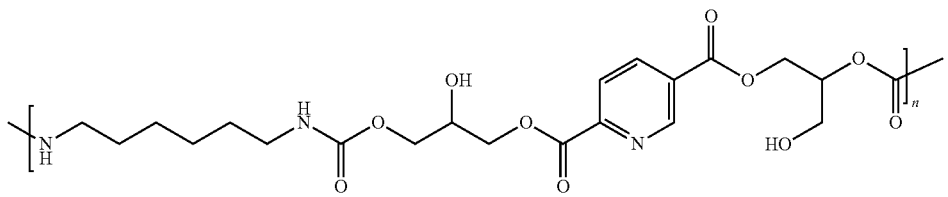
(11)
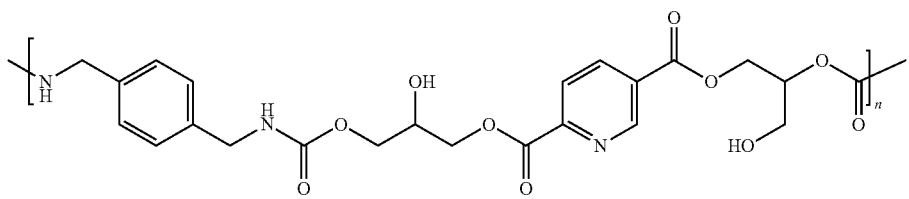
(12)
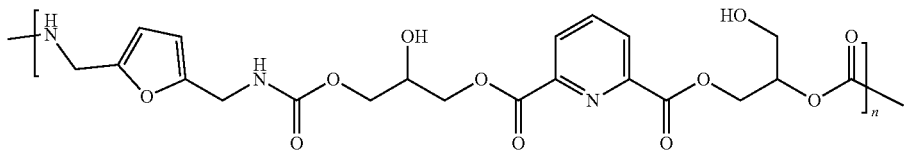
(13)
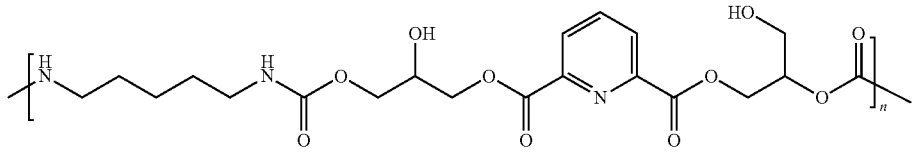
(14)
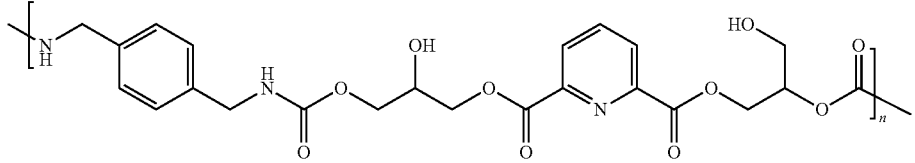
(15)

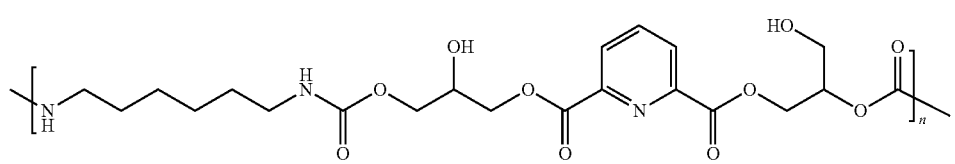
(16)
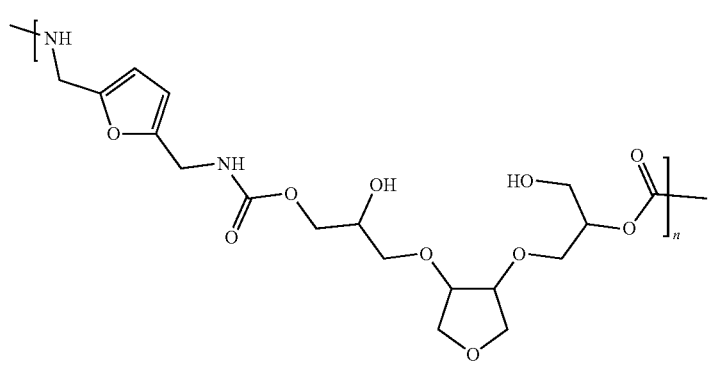
(17)
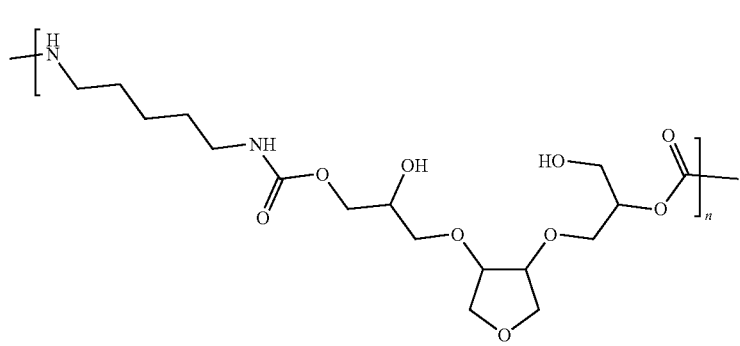
(18)
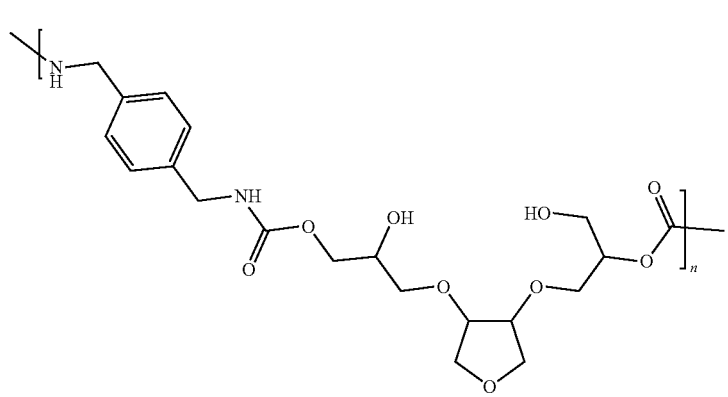
(19)
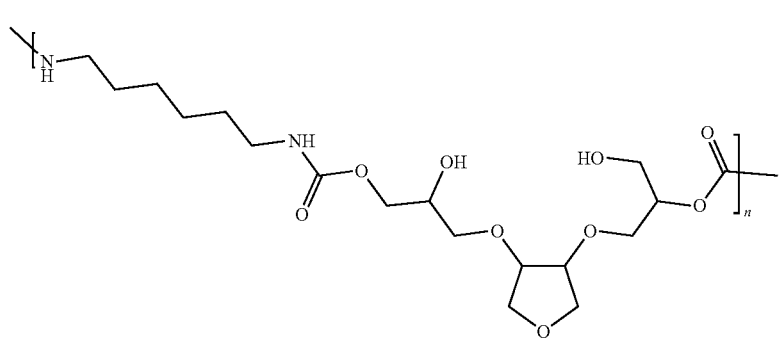
(20)
or a derivative thereof.
In one embodiment, the reaction product has one or more of the following properties: number average molecular weight (Mn) in the range of 2,000 g/mol to 50,000 g/mol, peak molecular weight (Mp) in the range of 1,500 g/mol to 60,000 g/mol and the polydispersity index (PDI) is in the range of 1.0 to 5.0, wherein the number average molecular weight, peak molecular weight and polydispersity index are determined by gel permeation chromatography using polymethyl methacrylate (PMMA) calibration.

In one aspect, there is provided a method of preparing the reaction product as disclosed herein, the method comprising:
reacting one or more compounds as disclosed herein with one or more amine containing compounds to obtain the reaction product.

In one embodiment, the amine containing compound comprises at least two amine functional groups.

In one embodiment, the amine containing compound is selected from the group consisting of furan-2,5-diyldimethanamine (FBA), xylene diamine (XDA), diaminopentane (DAP), hexamethylenediamine (HDA), ethylenediamine, diaminopropane, diaminobutane, ether diamine, polyether diamine, dimer diamine, lysine, isophorone diamine and phenylenediamine.

In one embodiment, the method is devoid of a step containing the use of isocyanates as a reactant.

In one embodiment, the method further comprises a step of functionalising one or more hydroxyl groups present in the reaction product.

In one embodiment, the method further comprises a step of grafting a polymer to one or more hydroxyl groups present in the reaction product.

In one embodiment, the method further comprises a step of grafting one or more molecular entities or polymers to one or more furan rings present in the reaction product.

In one aspect, there is provided a functionalised or grafted product obtained according to any one of the methods disclosed herein, wherein the functionalised or grafted polymer has one or more of the following properties: solubility or dispersibility in water, solubility or dispersibility in oil, photo or thermo or redox or pH response and crosslinking ability under air, photo, thermal, redox or ionic conditions.

Definitions

The term "cyclic" as used herein broadly refers to a structure where one or more series of atoms are connected to form at least one ring. The term includes, but is not limited to, both saturated and unsaturated 5-membered and saturated and unsaturated 6-membered rings. Examples of groups having a cyclic structure include, but are not limited to, cyclopentane, cyclopentene, cyclohexane, cyclohexene, benzene and the like. The term "cyclic" as used herein includes "heterocyclic".

The terms "alkyl", "alkenyl", "alkynyl", "alkoxy" or the like as used herein broadly include straight or branched hydrocarbon chains having up to 50 carbon atoms (i.e. $C_{1-50}$), up to 40 carbon atoms (i.e. $C_{1-40}$), up to 30 carbon atoms (i.e. $C_{1-30}$), up to 20 carbon atoms (i.e. $C_{1-20}$), up to 10 carbon atoms (i.e. $C_{1-10}$) or up to 6 carbon atoms (i.e. $C_{1-6}$). For example, the term "alkyl" includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like. For example, the term "alkenyl" includes, but is not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like. For example, the term "alkynyl" includes but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like. For example, the term "alkoxy" includes but is not limited to methoxy, ethoxy, n-propoxy, isopropoxy, tert-butoxy, and the like.

The term "heterocyclic" as used herein broadly refers to a structure where two or more different kinds of atoms are connected to form at least one ring. For example, a heterocyclic ring may be formed by carbon atoms and at least another atom (i.e. heteroatom) selected from oxygen (O), nitrogen (N) or (NH) and sulfur (S). The term also includes, but is not limited to, saturated and unsaturated 5-membered, and saturated and unsaturated 6-membered rings. Examples of groups having a heterocyclic structure include, but are not limited to furan, thiophene, 1H-pyrrole, 2H-pyrrole, 1-pyrroline, 2-pyrroline, 3-pyrroline, 1-pyrazoline, 2-pyrazoline, 3-pyrazoline, 2-imidazoline, 3-imidazoline, 4-imidazoline, pyrazole, imidazole, oxazole, isoxazole, thiazole, isothiazole, 1,2,3-triazole, 1,2,4-triazole, 1,2,3-oxadiazole, disubstituted 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, tetrahydrofuran, tetrahydrothiophene, pyrrolidine, 1,3-dioxolane, 1,2-oxathiolane, 1,3-oxathiolane, pyrazolidine, imidazolidine, pyridine, pyridazine, pyrimidine, pyrazine, 1,2-oxazine, 1,3-oxazine, 1,4-oxazine, thiazine, 1,2,3-triazine, 1,2,4-triazine, 1,3,5-triazine, 2H-pyran, 4H-pyran, 2-pyrone, 4-pyrone, 1,4-dioxin, 2H-thiopyran, 4H-thiopyran, tetrahydropyran, thiane, piperidine, 1,4-dioxane, 1,2-dithiane, 1,3-dithiane, 1,4-dithiane, 1,3,5-trithiane, piperazine, morpholine, thiomorpholine and the like.

The term "aromatic" as used herein when referring to hydrocarbons, refers broadly to hydrocarbons having a ring-shaped or cyclic structure with delocalised electrons between carbon atoms. The term encompasses, but is not limited to, monovalent ("aryl"), divalent ("arylene") monocyclic aromatic groups having 5 to 6 atoms. Examples of such groups include, but are not limited to, benzene, furan, thiophene, pyrrole, pyrazole, imidazole, oxazole, thiazole, triazole, oxadiazole, thiadiazole, tetrazole, benzofuran, benzothiophene, benzopyrrole, benzodifuran, benzodithiophene, benzodipyrrole, pyridine, pyridazine, pyrimidine, pyrazine, 1,2,3-triazine, 1,2,4-triazine, 1,3,5-triazine and the like.

The term "heteroaromatic" as used herein when referring to hydrocarbons, refers broadly to aromatic hydrocarbons that have one or more carbon atoms replaced by a heteroatom. The term encompasses, but is not limited to, monovalent ("aryl"), divalent ("arylene") monocyclic, polycyclic conjugated or fused aromatic groups having 5 to 14 atoms, where 1 to 6 atoms in each aromatic ring are heteroatoms selected from oxygen (O), nitrogen (N) or (NH) and sulfur (S). Examples of such groups include, but are not limited to, furan, thiophene, pyrrole, pyrazole, imidazole, oxazole, thiazole, triazole, oxadiazole, thiadiazole, tetrazole, benzofuran, benzothiophene, benzopyrrole, benzodifuran, benzodithiophene, benzodipyrrole, pyridine, pyridazine, pyrimidine, pyrazine, 1,2,3-triazine, 1,2,4-triazine, 1,3,5-triazine and the like.

The term "optionally substituted" as used herein when referring to a hydrocarbon or a chemical moiety, refers to both the situation where the hydrogen atoms originally present in the hydrocarbon or the chemical moiety are not substituted and the situation where one or more hydrogen atoms originally present in the hydrocarbon or the chemical moiety are substituted/replaced with another chemical group or atom. For example, the hydrogen atom(s) originally present may be substituted/replaced with/by a hydroxy group, a halogen, a cyano group, an amino group, a nitro group, a nitroalkyl group, a nitroalkenyl, a carboxyl group, an alkyl group, alkenyl group, an alkynyl group, an alkoxy group, a haloalkyl group, a haloalkoxy group, a haloalkenyloxy group, a cycloalkyl group, a cycloalkenyl group, a thioalkyl group, thioalkoxy group, heterocycloalkyl group, a nitroalkynyl group, a nitroheterocyclyl group, an alkylamino group, a dialkylamino group, an alkenylamine group, an alkynylamino group, an acyl group, an alkenoyl group, an alkynoyl group, an acylamino group, a diacylamino group, an acyloxy group, an alkylsulfonyloxy group, a heterocycloxy group, a heterocycloamino group, a haloheterocycloalkyl group, an alkylsulfenyl group, an alkylcarbonyloxy group, an alkylthio group, an acylthio group, phosphorus-containing groups such as phosphono and phosphinyl, an aryl group, a heteroaryl group, an alkylaryl group, an alkylheteroaryl group, silicon containing groups, boron containing groups or the like.

The term "monomer" as used herein broadly refers to a chemical entity that may be covalently linked to one or more of such entities to form a polymer.

The term "polymer" as used herein broadly refers to a chemical compound comprising a large number of repeating structural units (typically more than about 10, more than about, 20, more than about 30, more than about 40, or more than about 50) and is created through a process of polymerization. The units composing the polymer are typically derived from monomers. The term also encompasses homopolymers which are made up of one type of monomer and copolymers which are made up of two or more different monomers.

The term "precursor compound" as used herein broadly refers to a compound that may be chemically and/or physically transformed to eventually reach a compound of interest. The "precursor compound" may be transformed through one or more process steps. Therefore, it will also be understood that the "precursor compound" may be a compound that immediately or directly comes before the compound of interest in a production process for the compound of interest, or comes indirectly or several steps before the compound of interest in said production process. For example, Compound A may be transformed to Compound B before being transformed to Compound C. In this example, Compound A and Compound B may both be considered as precursor compounds of Compound C. Similarly, Compound A may be considered as a precursor compound of Compound B.

The terms "bio-based" or "bio-derived" as used herein broadly refer to the quality of being derived or being originated from living organisms or once-living organisms. Such living organisms may be animal or plants. Therefore, "bio-based source" includes, but is not limited to, a biofeedstock, a plant-based source or combinations thereof. Examples of "bio-based source" include, but are not limited to, biomass such as cellulose, hemicellulose, poly-/oligo-/di-saccharides, lignin, amino acids, triglycerides, hexose, glucose, fructose and erythritol.

The term "and/or", e.g., "X and/or Y" is understood to mean either "X and Y" or "X or Y" and should be taken to provide explicit support for both meanings or for either meaning.

Further, in the description herein, the word "substantially" whenever used is understood to include, but not restricted to, "entirely" or "completely" and the like. In addition, terms such as "comprising", "comprise", and the like whenever used, are intended to be non-restricting descriptive language in that they broadly include elements/components recited after such terms, in addition to other components not explicitly recited. For example, when "comprising" is used, reference to a "one" feature is also intended to be a reference to "at least one" of that feature. Terms such as "consisting", "consist", and the like, may in the appropriate context, be considered as a subset of terms such as "comprising", "comprise", and the like. Therefore, in embodiments disclosed herein using the terms such as "comprising", "comprise", and the like, it will be appreciated that these embodiments provide teaching for corresponding embodiments using terms such as "consisting", "consist", and the like. Further, terms such as "about", "approximately" and the like whenever used, typically means a reasonable variation, for example a variation of +/−5% of the disclosed value, or a variance of 4% of the disclosed value, or a variance of 3% of the disclosed value, a variance of 2% of the disclosed value or a variance of 1% of the disclosed value.

Furthermore, in the description herein, certain values may be disclosed in a range. The values showing the end points of a range are intended to illustrate a preferred range. Whenever a range has been described, it is intended that the range covers and teaches all possible sub-ranges as well as individual numerical values within that range. That is, the end points of a range should not be interpreted as inflexible limitations. For example, a description of a range of 1% to 5% is intended to have specifically disclosed sub-ranges 1% to 2%, 1% to 3%, 1% to 4%, 2% to 3% etc., as well as individually, values within that range such as 1%, 2%, 3%, 4% and 5%. The intention of the above specific disclosure is applicable to any depth/breadth of a range.

Additionally, when describing some embodiments, the disclosure may have disclosed a method and/or process as a particular sequence of steps. However, unless otherwise required, it will be appreciated that the method or process should not be limited to the particular sequence of steps disclosed. Other sequences of steps may be possible. The particular order of the steps disclosed herein should not be construed as undue limitations. Unless otherwise required, a method and/or process disclosed herein should not be limited to the steps being carried out in the order written. The sequence of steps may be varied and still remain within the scope of the disclosure.

DESCRIPTION OF EMBODIMENTS

Exemplary, non-limiting embodiments of a compound represented by general formula (Ia) and/or (Ib), a method of preparing said compound, a reaction product of the reaction between one or more said compound and one or more amine containing compounds, and a method of preparing said reaction product are disclosed hereinafter.

In various embodiments, there is provided a compound represented by general formula (Ia) and/or (Ib):

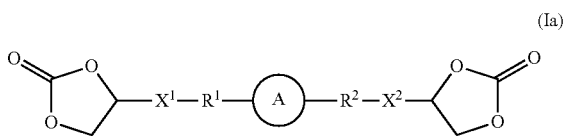

(Ia)

wherein
ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;
$R^1$ and $R^2$ are each independently selected from the group consisting of a single bond, —($C_1$-$C_6$ alkyl)-, —C(=O)—, —C(=O)—O—, —C(=O)—$NR^a$—, —C(=O)—($C_1$-$C_6$ alkyl)-, —C(=O)—O—($C_1$-$C_6$ alkyl)-, —C(=O)—$NR^a$—($C_1$-$C_6$ alkyl)-, —O—C(=O)—, —$NR^a$—C(=O)—, —($C_1$-$C_6$ alkyl)-C(=O)—, —($C_1$-$C_6$ alkyl)-O—C(=O)— and —($C_1$-$C_6$ alkyl)-$NR^a$—C(=O)—;
$X^1$ and $X^2$ are each independently selected from the group consisting of a single bond, —O—, —$NR^a$—, —($C_1$-$C_6$ alkyl)-O—, —($C_1$-$C_6$ alkyl)-$NR^a$—, —O—($C_1$-$C_6$ alkyl)- and —$NR^a$—($C_1$-$C_6$ alkyl)-;
$R^a$ is H or $C_1$-$C_6$ alkyl, and
wherein one or more hydrogen atom(s) in $C_1$-$C_6$ alkyl and ring A are optionally substituted and
with the proviso that when ring A is 1,4-phenylene, both $R^1$ and $R^2$ are not —C(=O)—, $X^1$ is not —($CH_2$)—O— and $X^2$ is not —O—($CH_2$)—,
or

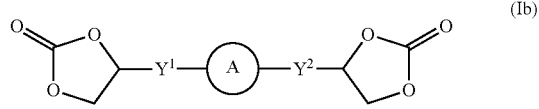

(Ib)

wherein
ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;
$Y^1$ is —$X^1$—$R^1$— and $Y^2$ is —$R^2$—$X^2$—, or
$Y^1$ and $Y^2$ are each independently selected from the group consisting of:
a single bond,
—Z—O—Z—,
—Z—$NR^b$—Z—,
—Z—O—C(=O)—Z—, —Z—C(=O)—O—Z—,
—Z—$NR^b$—C(=O)—Z—, —Z—C(=O)—$NR^b$—Z—,
—Z—$NR^b$—C(=O)—O—Z—, —Z—O—C(=O)—$NR^b$—Z—;
where each Z is independently selected from the group consisting of a single bond, optionally substituted saturated aliphatic chain and optionally substituted unsaturated aliphatic chain;
where $R^b$ is H or $C_1$-$C_6$ alkyl, and
with the proviso that when ring A is 1,4-phenylene, $Y^1$ is not —($CH_2$)—O—C(=O)— and $Y^2$ is not —C(=O)—O—($CH_2$)—.

In various embodiments, ring A is a 5-membered heterocyclic ring having three heteroatoms, two heteroatoms or one heteroatom independently selected from the group consisting of O, N, S and NH. For example, ring A may be selected from a furan (e.g. disubstituted furan), a thiophene (e.g. disubstituted thiophene), a pyrrole (e.g. disubstituted 1H-pyrrole, disubstituted 2H-pyrrole), pyrone, a pyrroline (e.g. disubstituted 1-pyrroline, disubstituted 2-pyrroline, disubstituted 3-pyrroline), a pyrazoline (e.g. disubstituted 1-pyrazoline, disubstituted 2-pyrazoline, disubstituted 3-pyrazoline), an imidazoline (e.g. disubstituted 2-imidazoline, disubstituted 3-imidazoline, disubstituted 4-imidazoline), a pyrazole (e.g. disubstituted pyrazole), a imidazole (e.g. disubstituted imidazole), a oxazole (e.g. disubstituted oxazole, disubstituted isoxazole), a thiazole (e.g. disubstituted thiazole, disubstituted isothiazole), a triazole (e.g. disubstituted 1,2,3-triazole, disubstituted 1,2,4-triazole), a oxadiazole (e.g. disubstituted 1,2,3-oxadiazole, disubstituted 1,2,4-oxadiazole, disubstituted 1,2,5-oxadiazole, disubstituted 1,3,4-oxadiazole), a thiadiazole (e.g. disubstituted 1,2,3-thiadiazole, disubstituted 1,2,4-thiadiazole, disubstituted 1,2,5-thiadiazole, disubstituted 1,3,4-thiadiazole), a tetrahydrofuran (e.g. disubstituted tetrahydrofuran), a tetrahydrothiophene (e.g. disubstituted tetrahydrothiophene), a pyrrolidine (e.g. disubstituted pyrrolidine), a dioxolane (e.g. disubstituted 1,3-dioxolane, disubstituted 1,2-oxathiolane, disubstituted 1,3-oxathiolane), a pyrazolidine (e.g. disubstituted pyrazolidine), a imidazolidine (e.g. disubstituted imidazolidine) and the like. It will be appreciated that in various embodiments, ring A may be termed as a disubstituted ring due to it having two bonds to $R^1$ and $R^2$ or $Y^1$ and $Y^2$.

In various embodiments, the 5-membered heterocyclic ring is heteroaromatic. In these embodiments, ring A is selected from disubstituted furan, disubstituted thiophene, disubstituted pyrrole, disubstituted pyrazole, disubstituted imidazole, oxazole, disubstituted thiazole, disubstituted triazole, disubstituted oxadiazole, disubstituted thiadiazole and the like.

In various embodiments, ring A is a 6-membered hydrocarbon cyclic ring. For example, ring A may be selected from disubstituted cyclohexane, disubstituted cyclohexene and disubstituted benzene.

In various embodiments, ring A is a 6-membered heterocyclic ring having three heteroatoms, two heteroatoms or one heteroatom independently selected from the group consisting of O, N, S and NH. For example, ring A may be selected from disubstituted pyridine, disubstituted pyridazine, disubstituted pyrimidine, disubstituted pyrazine, disubstituted 1,2-oxazine, disubstituted 1,3-oxazine, disubstituted 1,4-oxazine, disubstituted thiazine, disubstituted 1,2,3-triazine, 1,2,4-triazine, disubstituted 1,3,5-triazine, disubstituted 2H-pyran, disubstituted 4H-pyran, disubstituted 1,4-dioxin, disubstituted 2H-thiopyran, disubstituted 4H-thiopyran, disubstituted tetrahydropyran, disubstituted thiane, disubstituted piperidine, disubstituted 1,4-dioxane, disubstituted 1,2-dithiane, disubstituted 1,3-dithiane, disubstituted 1,4-dithiane, disubstituted 1,3,5-trithiane, disubstituted piperazine, disubstituted morpholine, disubstituted thiomorpholine and the like.

In various embodiments, the 6-membered hydrocarbon ring A is heteroaromatic. In these embodiments, ring A is selected from disubstituted pyridine, disubstituted pyridazine, disubstituted pyrimidine, disubstituted pyrazine, disubstituted 1,2,3-triazine, disubstituted 1,2,4-triazine and disubstituted 1,3,5-triazine and the like.

In various embodiments, ring A is selected from the group consisting of disubstituted furan, disubstituted tetrahydrofuran and disubstituted pyridine. In various embodiments, ring A is selected from the group consisting of 2,5-disubstituted furan, 3,4-disubstituted furan, 2,3-disubstituted furan, 2,4-disubstituted furan, 2,5-disubstituted pyridine, 2,6-disubstituted pyridine, 2,3-disubstituted pyridine, 2,4-disubstituted pyridine, 3,5-disubstituted pyridine, 3,4-disubstituted pyridine, 3,4-disubstituted tetrahydrofuran, 2,5-disubstituted tetrahydrofuran, 2,3-disubstituted tetrahydrofuran and 2,4-disubstituted tetrahydrofuran. In some embodiments, ring A is 2,5-disubstituted furan, 2,5-disubstituted pyridine, 2,6-disubstituted pyridine, 2,4-disubstituted pyridine, 3,5-disubstituted pyridine, or 3,4-disubstituted tetrahydrofuran.

In various embodiments, ring A is selected from any one of the general formulae (II) to (V):

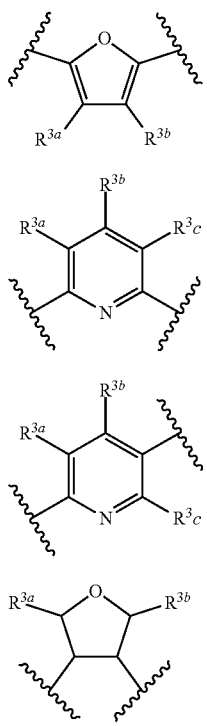

wherein $R^{3a}$, $R^{3b}$ and $R^{3c}$ are each independently selected from the group consisting of a hydrogen atom, a hydroxyl group, a halogen atom, a cyano group, an amino group, a nitro group, a carboxyl group, $C_1$-$C_6$ alkyl group, a $C_2$-$C_6$ alkenyl group, a $C_2$-$C_6$ alkynyl group a $C_1$-$C_6$ alkoxy group, a $C_1$-$C_6$ haloalkyl group, a $C_1$-$C_6$ haloalkoxy group, a $C_3$-$C_7$ cycloalkyl group, a $C_3$-$C_7$ cycloalkenyl group, a $C_1$-$C_6$ alkylcarbonyl group and a $C_1$-$C_6$ alkoxycarbonyl group.

In various embodiments, $R^{3a}$, $R^{3b}$ and $R^{3c}$ are each a hydrogen atom.

In various embodiments, $R^1$ is selected from the group consisting of a single bond, —($C_1$-$C_6$ alkyl)-, —C(=O)—, —C(=O)—O—, —C(=O)—NR$^a$—, —C(=O)—($C_1$-$C_6$ alkyl)-, —C(=O)—O—($C_1$-$C_6$ alkyl)- and —C(=O)—NR$^a$—($C_1$-$C_6$ alkyl)-, where $R^a$ is H or $C_1$-$C_6$ alkyl. In various embodiments, $R^2$ is selected from the group consisting of a single bond, —($C_1$-$C_6$ alkyl)-, —C(=O)—, —O—C(=O)—, —NR$^a$—C(=O)—, —($C_1$-$C_6$ alkyl)-C(=O)—, —($C_1$-$C_6$ alkyl)-O—C(=O)— and —($C_1$-$C_6$ alkyl)-NR$^a$—C(=O)—, where $R^a$ is H or $C_1$-$C_6$ alkyl.

In various embodiments, $R^1$ is selected from the group consisting of a single bond, —($C_1$-$C_6$ alkyl)-, —C(=O)—, —C(=O)—O— and —C(=O)—NR$^a$—, where $R^a$ is H or $C_1$-$C_6$ alkyl. In various embodiments, $R^2$ is selected from the group consisting of a single bond, —($C_1$-$C_6$ alkyl)-, —C(=O)—, —O—C(=O)— and —NR$^a$—C(=O)—, where $R^a$ is H or $C_1$-$C_6$ alkyl. In some embodiments, $R^a$ is H.

In various embodiments, $X^1$ is selected from the group consisting of —O—, —NR$^a$—, —($C_1$-$C_6$ alkyl)-O— and —($C_1$-$C_6$ alkyl)-NR$^a$—, where $R^a$ is H or $C_1$-$C_6$ alkyl. In various embodiments, $X^2$ is selected from the group consisting of —O—, —NR$^a$—, —O—($C_1$-$C_6$ alkyl)- and —NR$^a$—($C_1$-$C_6$ alkyl)-, where $R^a$ is H or $C_1$-$C_6$ alkyl. In some embodiments, $R^a$ is H.

In various embodiments, $Y^1$ is selected from the group consisting of a single bond, —Z—O—Z—, —Z—NR$^b$—Z—, —Z—O—C(=O)—Z—, —Z—NR$^b$—C(=O)—Z— and —Z—NR$^b$—C(=O)—O—Z—, where $R^b$ is H or $C_1$-$C_6$ alkyl.

In various embodiments, $Y^2$ is selected from the group consisting of a single bond, —Z—O—Z—, —Z—NR$^b$—Z—, —Z—C(=O)—O—, —Z—C(=O)—NR$^b$—Z— and Z—O—C(=O)—NR$^b$—Z—, where $R^b$ is H or $C_1$-$C_6$ alkyl.

In various embodiments, the compound represented by general formula (Ia) and/or (Ib) comprises cyclic biscarbonate functionality. The cyclic biscarbonate may be furan-based cyclic biscarbonate, a pyridine-based cyclic biscarbonate or a tetrahydrofuran-based cyclic biscarbonate. Advantageously, embodiments of the compound disclosed herein possessing said cyclic biscarbonate functionality make the compounds disclosed herein attractive for use as monomers in polymerization reactions.

In various embodiments, the compound represented by general formula (Ia) and/or (Ib) comprises ether, amine, ester, amide or carbamate linkages.

In various embodiments, when the compound disclosed herein is a cyclic biscarbonate comprising ether linkages, $R^1$ and $R^2$ are each independently selected from the group consisting of a single bond and —($C_1$-$C_6$ alkyl)-; $X^1$ is —($C_1$-$C_6$ alkyl)-O—; and $X^2$ is —O—($C_1$-$C_6$ alkyl)-. In some embodiments, $R^1=R^2=$a single bond; $X^1=$—($C_1$-$C_6$ alkyl)-O—; and $X^2=$—O—($C_1$-$C_6$ alkyl)-. In some other embodiments, $R^1=R^2=$—($C_1$-$C_6$ alkyl)-; $X^1=$—($C_1$-$C_6$ alkyl)-O—; and $X^2=$—O—($C_1$-$C_6$ alkyl)-, or $Y^1$ and $Y^2$ are each —Z—O—Z—.

In various embodiments, when the compound disclosed herein is a cyclic biscarbonate comprising amine linkages, $R^1$ and $R^2$ are each independently selected from the group consisting of a single bond and —($C_1$-$C_6$ alkyl)-; $X^1$ is —($C_1$-$C_6$ alkyl)-NR$^a$—; and $X^2$ is —NR$^a$—($C_1$-$C_6$ alkyl)-, where $R^a$ is H or $C_1$-$C_6$ alkyl. In some embodiments, $R^1=R^2=$a single bond; $X^1=$—($C_1$-$C_6$ alkyl)-NH—; and $X^2=$—HN—($C_1$-$C_6$ alkyl)-. In some embodiments, $R^1=R^2=$—($C_1$-$C_6$ alkyl)-; $X^1=$—($C_1$-$C_6$ alkyl)-NH—; and $X^2=$—HN—($C_1$-$C_6$ alkyl)-, or $Y^1$ and $Y^2$ are each —Z—NR$^b$—Z—.

In various embodiments, when the compound disclosed herein is a cyclic biscarbonate comprising ester linkages, $R^1$ is selected from the group consisting of —C(=O)— and —C(=O)—($C_1$-$C_6$ alkyl)-; $R^2$ is selected from the group consisting of —C(=O)— and —($C_1$-$C_6$ alkyl)-C(=O)—; $X^1$ is —($C_1$-$C_6$ alkyl)-O—; and $X^2$ is —O—($C_1$-$C_6$ alkyl)-. In some embodiments, $R^1=R^2=$—C(=O)—; $X^1=$—($C_1$-$C_6$ alkyl)-O—; and $X^2=$—O—($C_1$-$C_6$ alkyl)-, or $Y^1$ and $Y^2$ are each independently selected from the group consisting of —Z—O—C(=O)—Z— and —Z—C(=O)—O—Z—. In some embodiments, $Y^1$ is —Z—O—C(=O)—Z— and $Y^2$ is —Z—C(=O)—O—Z—.

In various embodiments, when the compound disclosed herein is a cyclic biscarbonate comprising amide linkages, $R^1$ is selected from the group consisting of —C(=O)— and —C(=O)—($C_1$-$C_6$ alkyl)-; $R^2$ is selected from the group consisting of —C(=O)— and —($C_1$-$C_6$ alkyl)-C(=O)—; $X^1$ is —($C_1$-$C_6$ alkyl)-$NR^a$—; and $X^2$ is —$NR^a$—($C_1$-$C_6$ alkyl)-, where $R^a$ is H or $C_1$-$C_6$ alkyl. In some embodiments, $R^1$=$R^2$=—C(=O)—; $X^1$=—($C_1$-$C_6$ alkyl)-NH—; and $X^2$=—HN—($C_1$-$C_6$ alkyl)-, or $Y^1$ and $Y^2$ are each independently selected from the group consisting of —Z—$NR^b$—C(=O)—Z— and —Z—C(=O)—$NR^b$—Z—. In some embodiments, $Y^1$ is —Z—$NR^b$—C(=O)—Z— and $Y^2$ is —Z—C(=O)—$NR^b$—Z—.

In various embodiments, when the compound disclosed herein is a cyclic biscarbonate comprising carbamate linkages, $R^1$ is selected from the group consisting of —C(=O)—O—, —C(=O)—$NR^a$—, —C(=O)—O—($C_1$-$C_6$ alkyl)- and —C(=O)—$NR^a$—($C_1$-$C_6$ alkyl)-; $R^2$ is selected from the group consisting of —O—C(=O)—, —$NR^a$—C(=O)—, —($C_1$-$C_6$ alkyl)-O—C(=O)— and —($C_1$-$C_6$ alkyl)-$NR^a$—C(=O)—; $X^1$ is selected from the group consisting of —($C_1$-$C_6$ alkyl)-O— and —($C_1$-$C_6$ alkyl)-$NR^a$—; $X^2$ is selected from the group consisting of —O—($C_1$-$C_6$ alkyl)- and —$NR^a$—($C_1$-$C_6$ alkyl)-, where $R^a$ is H or $C_1$-$C_6$ alkyl. In some embodiments, $R^1$=—C(=O)—O—; $R^2$=—O—C(=O)—, $X^1$=—($C_1$-$C_6$ alkyl)-NH—; and $X^2$=—HN—($C_1$-$C_6$ alkyl)-. In some other embodiments, $R^1$=—C(=O)—NH—; $R^2$ is —NH—C(=O)—, $X^1$=—($C_1$-$C_6$ alkyl)-O—; and $X^2$=—($C_1$-$C_6$ alkyl)-, or $Y^1$ and $Y^2$ are each independently selected from the group consisting of —Z—$NR^b$—C(=O)—O—Z— and —Z—O—C(=O)—$NR^b$—Z—. In some embodiments, $Y^1$ is —Z—$NR^b$—C(=O)—O—Z— and $Y^2$ is —Z—O—C(=O)—$NR^b$—Z—.

In various embodiments, $R^1$ and $R^2$ are each independently selected from the group consisting of a single bond, —($C_1$-$C_6$ alkyl)- and —C(=O)—. In various embodiments, —($C_1$-$C_6$ alkyl)- may be a straight or branched alkyl chain. In some embodiments, —($C_1$-$C_6$ alkyl)- is a linear alkyl chain selected from the group consisting of methyl (i.e. $C_1$ alkyl), ethyl (i.e. $C_2$ alkyl), propyl (i.e. $C_3$ alkyl), butyl (i.e. $C_4$ alkyl), pentyl (i.e. C alkyl) and hexyl (i.e. C alkyl). In other embodiments, —($C_1$-$C_6$ alkyl)- is a branched alkyl chain selected from the group consisting of isopropyl (i.e. $C_3$ alkyl), isobutyl (i.e. $C_4$ alkyl), sec-butyl (i.e. $C_4$ alkyl), tert-butyl (i.e. $C_4$ alkyl), 2-methylbutyl (or isopentyl) (i.e. C alkyl), 2,2-dimethylpropyl (or neopentyl) (i.e. C alkyl), tert-amyl (i.e. $C_5$ alkyl), 2-methylpentyl (isohexyl) (i.e. C alkyl), 3-methylpentyl (i.e. C alkyl), 2,2-dimethylbutyl (i.e. C alkyl) and 2,3-dimethylbutyl (i.e. C alkyl).

In various embodiments, $X^1$ is selected from the group consisting of —($C_1$-$C_6$ alkyl)-O— and —($C_1$-$C_6$ alkyl)-NH—. In various embodiments, $X^2$ is selected from the group consisting of —O—($C_1$-$C_6$ alkyl)- and —NH—($C_1$-$C_6$ alkyl)-. In various embodiments, —($C_1$-$C_6$ alkyl)- may be a straight or branched alkyl chain. In some embodiments, —($C_1$-$C_6$ alkyl)- is a linear alkyl chain selected from the group consisting of methyl (i.e. $C_1$ alkyl), ethyl (i.e. $C_2$ alkyl), propyl (i.e. $C_3$ alkyl), butyl (i.e. $C_4$ alkyl), pentyl (i.e. $C_5$ alkyl) and hexyl (i.e. C alkyl). In other embodiments, —($C_1$-$C_6$ alkyl)- is a branched alkyl chain selected from the group consisting of isopropyl (i.e. $C_3$ alkyl), isobutyl (i.e. $C_4$ alkyl), sec-butyl (i.e. $C_4$ alkyl), tert-butyl (i.e. $C_4$ alkyl) and tert-amyl (i.e. $C_5$ alkyl).

In various embodiments, $X^1$ is selected from the group consisting of —$H_2C$—O— and —$H_2C$—NH—. In various embodiments, $X^2$ is selected from the group consisting of —O—$CH_2$— and —NH—$CH_2$—. In various embodiments, $R^1$ and $R^2$ are each independently selected from the group consisting of a single bond, —$CH_2$— and —C(=O)—.

In various embodiments, $R^1$ and $R^2$ are the same. For example, $R^1$=$R^2$=a single bond, or $R^1$=$R^2$=—($C_1$-$C_6$ alkyl)- or $R^1$=$R^2$=—C(=O)—. As may be appreciated, when $R^1$ and $R^2$ are indicated to be the same, it includes the situation where $R^1$ shares the same chemical functionality/chemical group as $R^2$ even though the structural formula of $R^1$ is recited in the reverse direction from that of $R^2$, for example, when $R^1$=—C(=O)—O— and $R^2$=—O—C(=O)—; or when $R^1$=—C(=O)—NH— and $R^2$=—NH—C(=O)—.

In various embodiments, $X^1$ and $X^2$ are the same. As may be appreciated, when $X^1$ and $X^2$ are indicated to be the same, it includes the situation where $X^1$ shares the same chemical functionality/chemical group as $X^2$ even though the structural formula of $X^1$ is recited in the reverse direction as that of $X^2$, for example, when $X^1$=—($C_1$-$C_6$ alkyl)-O— and $X^2$=—O—($C_1$-$C_6$ alkyl)-; or when $X^1$=—($C_1$-$C_6$ alkyl)-$NR^a$— and $X^2$=—$NR^a$—($C_1$-$C_6$ alkyl)-.

In various embodiments, $Y^1$ and $Y^2$ are the same. As may be appreciated, when $Y^1$ and $Y^2$ are indicated to be the same, it includes the situation where $Y^1$ shares the same chemical functionality/chemical group as $Y^2$ even though the structural formula of $Y^1$ is recited in the reverse direction as that of $Y^2$, for example, when $Y^1$=—($C_1$-$C_6$ alkyl)-O— and $Y^2$=—($C_1$-$C_6$ alkyl)-; or when $Y^1$=—($C_1$-$C_6$ alkyl)-O—C(=O)— and $Y^2$=—C(=O)—O—($C_1$-$C_6$ alkyl)-.

In various embodiments, ring A is not 1,4-phenylene, or is not phenylene or is not an aromatic group containing 6 or more carbon atoms. In some embodiments, $R^1$ is not —C(=O)—. In some embodiments, $R^2$ is not —C(=O)—. In some embodiments, $X^1$ is not —($CH_2$)—O—. In some embodiments, $X^2$ is not —O—($CH_2$)—. In some embodiments, $Y^1$ is not —($CH_2$)—O—C(=O)—. In some embodiments, $Y^2$ is not —C(=O)—O—($CH_2$)—.

In various embodiments, each Z can be the same or different and is each independently selected from the group consisting of a single bond, saturated aliphatic chain and unsaturated aliphatic chain. In various embodiments, the saturated or unsaturated aliphatic chain is unsubstituted. In various embodiments, the saturated or unsaturated aliphatic chain comprises linear, branched and/or cyclic hydrocarbon compound having from 1 carbon atom to 12 carbon atoms, or from 1 carbon atom to 6 carbon atoms. For example, the saturated aliphatic chain may be —$C_1$-$C_{12}$ alkyl- or —$C_1$-$C_{12}$ cycloalkyl- and the unsaturated aliphatic chain may be —$C_1$-$C_{12}$ alkenyl-, —$C_1$-$C_{12}$ alkynyl- or —$C_1$-$C_{12}$ cycloalkenyl-. In some embodiments, the saturated or unsaturated aliphatic chain further comprises at least one substituent selected from the group consisting of O, N, S and NH. For example, the saturated aliphatic chain may be —$C_1$-$C_{12}$ heteroalkyl-, —$C_1$-$C_{12}$ alkylcarbonyl- or —$C_1$-$C_{12}$ alkylamino- and the unsaturated aliphatic chain may be —$C_1$-$C_{12}$ heteroalkenyl-, —$C_1$-$C_{12}$ alkenylcarbonyl- or —$C_1$-$C_{12}$ alkenylamino-. In various embodiments, one or more hydrogen atom(s) in the saturated aliphatic chain and unsaturated aliphatic chain are optionally substituted.

In various embodiments, the compound is selected from the following:

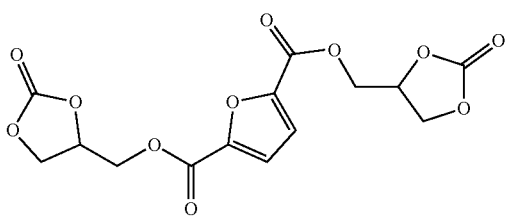 [SMILES: O=C1OCC(COC(=O)c2ccc(C(=O)OCC3COC(=O)O3)o2)O1]

bis((2-oxo-1,3-dioxolan-4-yl)methyl)furan-2,5-dicarboxylate (FBC-1);

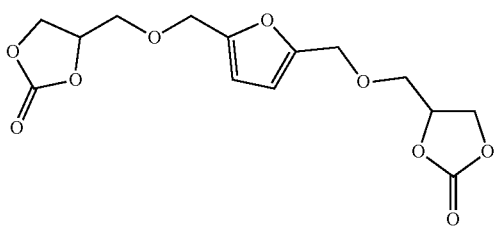 [SMILES: O=C1OCC(COCc2ccc(COCC3COC(=O)O3)o2)O1]

4,4'-(((furan-2,5-diylbis(methylene))bis(oxy))bis(methylene))bis(1,3-dioxolan-2-one) (FBC-2);

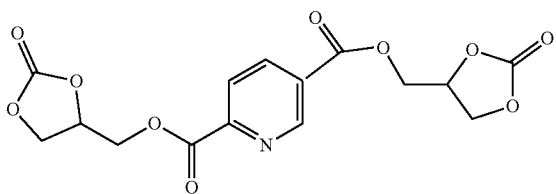 [SMILES: O=C1OCC(COC(=O)c2ccc(C(=O)OCC3COC(=O)O3)nc2)O1]

bis((2-oxo-1,3-dioxolan-4-yl)methyl)pyridine-2,5-dicarboxylate (PBC);

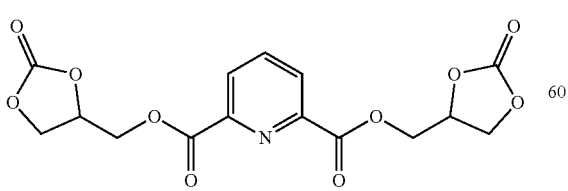

bis((2-oxo-1,3-dioxolan-4-yl)methyl)pyridine-2,6-dicarboxylate (PBC-2); and

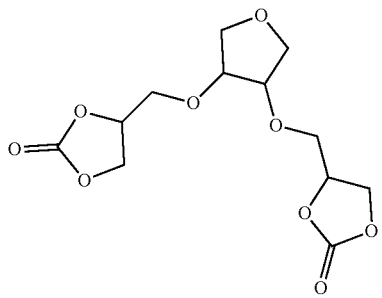 [SMILES: O=C1OCC(COC2COCC2OCC2COC(=O)O2)O1]

4,4'-(((tetrahydrofuran-3,4-diyl)bis(oxy))bis(methylene))bis(1,3-dioxolan-2-one) (HFBC).

In various embodiments, the aromatic units present in the compound disclosed herein are in the form of a disubstituted furan or in the form of a disubstituted pyridine. Various embodiments of the compound disclosed herein do not contain or is substantially devoid of structures that resemble bisphenol A, p-terephathlic acid and vanillin-based linkers.

Various embodiments of the compound disclosed herein differ from a similar compound containing bisphenol A at least in that embodiments of compound disclosed herein does not contain

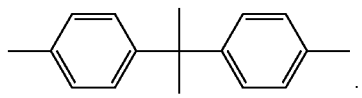

Various embodiments of the compound disclosed herein differ from a similar compound containing p-terephathlic acid at least in that embodiments of compound disclosed herein does not contain

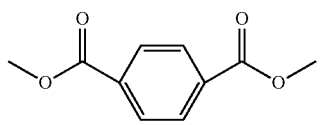

Various embodiments of the compound disclosed herein differ from a similar compound containing p-terephathlic acid at least in that embodiments of compound disclosed herein does not contain

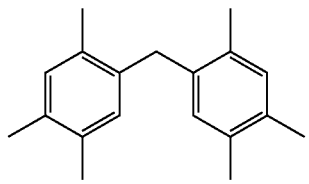

In various embodiments, there is provided a method of preparing a compound represented by general formula (Ia) and/or (Ib), the method comprising:

deriving a precursor compound represented by general formula (VI), optionally from a bio-based source:

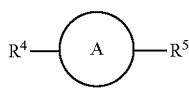

(VI)

wherein
ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;

$R^4$ and $R^5$ are each independently selected from the group consisting of —OH, —C(=O)H, —C(=O)—OH, —$NR^cR^d$, —C(=O)—$NR^cR^d$, —($C_1$-$C_6$ alkyl)-OH, —($C_1$-$C_6$ alkyl)-C(=O)H, —($C_1$-$C_6$ alkyl)-C(=O)—OH, —($C_1$-$C_6$ alkyl)-$NR^cR^d$ and —($C_1$-$C_6$ alkyl)-C(=O)—$NR^cR^d$, where $R^c$ and $R^d$ are independently selected from the group consisting of H or $C_1$-$C_6$ alkyl; and converting the precursor compound to said compound through one or more chemical reactions, wherein at least one of the one or more chemical reactions is carried out in the presence of a halogenated compound.

In various embodiments, the step of deriving a precursor compound from a bio-based source comprises subjecting the bio-based source to a variety of chemical, physical and/or biological steps/reactions/processes. In various embodiments, the chemical and/or biological reactions comprise biocatalysis, fermentation and dehydration, optionally catalysed with an acid or a base. Physical steps or processes may include milling, grinding, crushing, pulverizing or the like.

In various embodiments, the bio-based source comprises biomass selected from plant-based polymers/molecules and sugar molecules. In some embodiments, the plant-based polymer/molecules comprises phenolic groups. In one embodiment, the plant-based polymer is cellulose, hemicellulose, and lignin. In some embodiments, the sugar molecules are selected from the group consisting of hexose, glucose, fructose and erythritol.

In various embodiments, the bio-based source is biomass feedstock.

In various embodiments, the step of deriving the precursor compound comprises deriving the precursor compound from a bio-based source selected from cellulose, hemicellulose, lignin, triglycerides, amino acids, hexose, glucose, fructose and erythritol.

In various embodiments of the method disclosed herein, the precursor compound is selected from the group consisting of 5-hydroxymethylfurfural (HMF), furan-2,5-diyldimethanol (FDM), furan-2,5-dicarboxylic acid (FDCA), furan-2,5-diyldimethanamine (FBA), pyridine-2,5-dicarboxylic acid, pyridine-2,6-dicarboxylic acid, pyridine-3-5 dicarboxyllic acid and 1,4-anhydroerythritol.

In various embodiments, ring A is similar to that described above.

In various embodiments, $R^4$ and $R^5$ are each independently selected from the group consisting of —OH, —C(=O)H, —C(=O)—OH, —($C_1$-$C_6$ alkyl)-OH and —($C_1$-$C_6$ alkyl)-$NR^cR^d$, where $R^c$ and $R^d$ are independently selected from the group consisting of H or $C_1$-$C_6$ alkyl. In various embodiments, both $R^c$ and $R^d$ are H. In various embodiments, $R^4$ and $R^5$ are each independently selected from the group consisting of —OH, —C(=O)H, —C(=O)—OH, —$CH_2$—OH and —$CH_2$—$NH_2$.

In various embodiments, $R^4$ and $R^5$ are the same. For example, in some embodiments, both $R^4$ and $R^5$ are each —$CH_2$—OH. In some embodiments, both $R^4$ and $R^5$ are each —C(=O)—OH. In some embodiments, both $R^4$ and $R^5$ are each —$CH_2$—$NH_2$. In some embodiments, both $R^4$ and $R^5$ are each —OH.

In various embodiments, $R^4$ and $R^5$ are not the same. For example, in some embodiments, $R^4$ is —$CH_2$—OH and $R^5$ is —C(=O)H. In some embodiments, $R^5$ is —$CH_2$—OH and $R^4$ is —C(=O)H.

In various embodiments, the step of converting the precursor compound to the compound represented by general formula (Ia) and/or (Ib) through one or more chemical reactions comprises performing at least one of the one or more chemical reactions to form an ester, an ether, an amine, an amide, or a carbamate.

In various embodiments, the step of converting the precursor compound to the compound represented by general formula (Ia) and/or (Ib) through one or more chemical reactions comprises performing at least one of the one or more chemical reactions in the presence of a halogenated compound. The halogen in the halogenated compound may be selected from the group consisting of F, Cl, Br and I.

In various embodiments, the halogenated compound comprises a halogenating agent. The halogenating agent may be a compound added to introduce halogen atom(s) to the precursor compound. Any suitable halgenating agent that effectively add halogen atom(s) to the precursor compound may be used in embodiments of the method disclosed herein. In various embodiments, the halogenating agent (e.g. chlorinating agent) is added to convert carboxylic acid groups in the precursor compound into acid chloride groups. In these embodiments, the chlorinating agent may be selected from the group consisting of thionyl chloride, oxalyl chloride, phosphorus (V) chloride ($PCl_5$), phosphorus (III) chloride ($PCl_3$) and cyanuric chloride and the like.

In various embodiments, the halogenated compound may be used to introduce a functional group. For example, the halogenated compound may be epichlorohydrin which may be used to introduce an epoxide functional group. Accordingly, in various embodiments, the halogenated compound comprises an alkylating agent. The alkylating agent may be a compound added to introduce desired aliphatic carbon chain(s) to the precursor compound. Any suitable alkylating agent that effectively add aliphatic carbon chain(s) to the precursor compound may be used in embodiments of the method disclosed herein. In various embodiments, the alkylating agent is added to convert hydroxy groups in the precursor compound into alkoxy groups. In these embodiments, the alkylating agent may be selected from the group consisting of allylbromide and epichlorohydrin.

In various embodiments, the one or more chemical reactions comprises performing at least one of the one or more chemical reactions in the presence of an alcohol after the addition of a halogenated compound. In some embodiments, the alcohol may be selected from the group consisting of glycerol carbonate and pyridinedimethanol.

In various embodiments, the one or more chemical reactions are performed in a solvent system. Any suitable solvent that effectively serves as a medium to contain the components of the mixture may be used in embodiments of the method disclosed herein. In various embodiments, the solvent is capable of substantially dissolving the components present in the composition. In some embodiments, the solvent system comprises an organic solvent. The organic solvent may be anhydrous or dry solvent. In other embodiments, the solvent system comprises aqueous solutions. In some embodiments, the solvent system is made up of solvents selected from the group consisting of dimethylformamide (DMF), tetrahydrofuran (THF), acetone, dichloromethane (DCM), acetonitrile (ACN), dimethyl sulfoxide (DMSO), γ-valerolactone (GVL), propylene carbonate (PC), dimethylcarbonate (DMC), dioxane, dioxolane, diglyme, acetone, methyl ethyl ketone (MEK), alcohols, esters, ethers, water, sodium hydroxide solution, potassium hydroxide solution and the like and combinations thereof. In various embodiments, the solvent may be used a catalyst to catalyse one or more chemical reactions.

In various embodiments, the method of preparing a compound represented by general formula (Ia) and/or (Ib) from a precursor compound has a yield of no less than about 35%, no less than about 45%, no less than about 50%, no less than about 55%, no less than about 60%, no less than about 65%, no less than about 70%, no less than about 75%, no less than about 80%, no less than about 85%, or no less than about 90%.

In various embodiments, the method of preparing a compound represented by general formula (Ia) and/or (Ib) is bio-based or bio-derived. Unlike conventional methods which generally use toxic precursor compounds as starting materials, embodiments of the method disclosed herein use precursor compounds derived from readily available biomass, thereby making the presently disclosed method an environmentally benign process. At the same time, utilising renewable biomass feedstock promotes resource conservation, thereby contributing to environmental sustainability.

In various embodiments, the compounds disclosed herein are capable of being used as monomers for polymerisation reactions, particularly in the synthesis of polymers containing hydroxyl groups and urethane/carbamate linkages, i.e. polyhydroxyurethanes.

In various embodiments, there is provided a reaction product of the reaction between one or more compounds represented by general formula (Ia) and/or (Ib) and one or more amine containing compounds, the reaction product having hydroxyl groups and urethane/carbamate linkages. In one embodiment, the reaction product is a polymer obtained from the polymerisation of one or more compounds represented by general formula (Ia) and/or (Ib) and one or more amine containing compounds. The reaction product may be an oligomer or a polymer.

In various embodiments, there is provided a reaction product that is a polymer having a repeating unit represented by general formula (VIIa) and/or (VIIb):

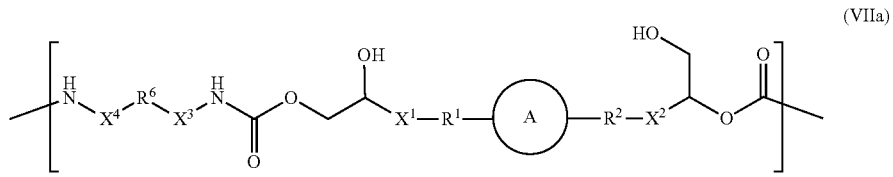

(VIIa)

wherein
ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;

$R^1$ and $R^2$ are each independently selected from the group consisting of a single bond, —($C_1$-$C_6$ alkyl)-, —C(=O)—, —C(=O)—O—, —C(=O)—$NR^a$—, —C(=O)—($C_1$-$C_6$ alkyl)-, —C(=O)—O—($C_1$-$C_6$ alkyl)-, —C(=O)—$NR^a$—($C_1$-$C_6$ alkyl)-, —O—C(=O)—, —$NR^a$—C(=O)—, —($C_1$-$C_6$ alkyl)-C(=O)—, —($C_1$-$C_6$ alkyl)-O—C(=O)— and —($C_1$-$C_6$ alkyl)-$NR^a$—C(=O)—;

$X^1$ and $X^2$ are each independently selected from the group consisting of a single bond, —O—, —$NR^a$—, —($C_1$-$C_6$ alkyl)-O—, —($C_1$-$C_6$ alkyl)-$NR^a$—, —O—($C_1$-$C_6$ alkyl)- and —$NR^a$—($C_1$-$C_6$ alkyl)-;

$R^a$ is H or $C_1$-$C_6$ alkyl; and $R^6$ is selected from the group consisting of optionally substituted alkyl, optionally substituted alkenyl, optionally substituted alkynyl, optionally substituted polyether, optionally substituted 5-membered or 6-membered hydrocarbon cyclic ring and an optionally substituted 5-membered or 6-membered heterocyclic ring having up to three heteroatoms independently selected from the group consisting of O and S;

$X^3$ and $X^4$ are each independently selected from the group consisting of a single bond and —($C_1$-$C_6$ alkyl), and with the proviso that when ring A is 1,4-phenylene, both $R^1$ and $R^2$ are not —C(=O)—, $X^1$ is not —($CH_2$)—O— and $X^2$ is not —O—($CH_2$)— or

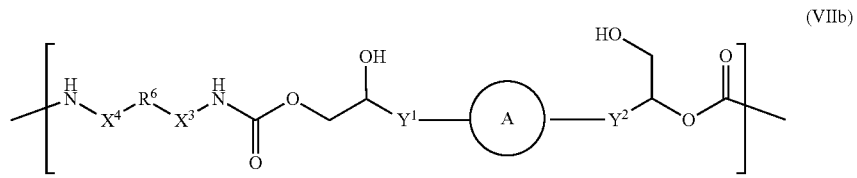

(VIIb)

wherein
ring A is an optionally substituted 5-membered or 6-membered hydrocarbon cyclic ring, or an optionally substituted 5-membered or 6-membered heterocyclic ring having up to three heteroatoms independently selected from the group consisting of O, N, S and NH;

$Y^1$ is —$X^1$—$R^1$— and $Y^2$ is —$R^2$—$X^2$—, or $Y^1$ and $Y^2$ are each independently selected from the group consisting of:

a single bond,
—Z—O—Z—,
—Z—$NR^b$—Z—,
—Z—O—C(=O)—Z—, —Z—C(=O)—O—Z—,
—Z—$NR^b$—C(=O)—Z—, —Z—C(=O)—$NR^b$—Z—,
—Z—$NR^b$—C(=O)—O—Z—, —Z—O—C(=O)—$NR^b$—Z—;

where each Z is independently selected from the group consisting of a single bond, optionally substituted saturated aliphatic chain and optionally substituted unsaturated aliphatic chain;

where $R^b$ is H or $C_1$-$C_6$ alkyl, and with the proviso that when ring A is 1,4-phenylene, $Y^1$ is not —(CH$_2$)—O—C(=O)— and $Y^2$ is not —C(=O)—O—(CH$_2$)—.

In various embodiments of the reaction product disclosed herein, ring A, $R^1$, $R^2$, $R^6$, $X^1$, $X^2$, $X^3$, $X^4$, $Y^1$ and $Y^2$ are similar to that described above.

In various embodiments, the reaction product comprises a derivative of a polymer of Formula VIIa and/or VIIb.

In various embodiments, the reaction product is selected from the following:

(1)

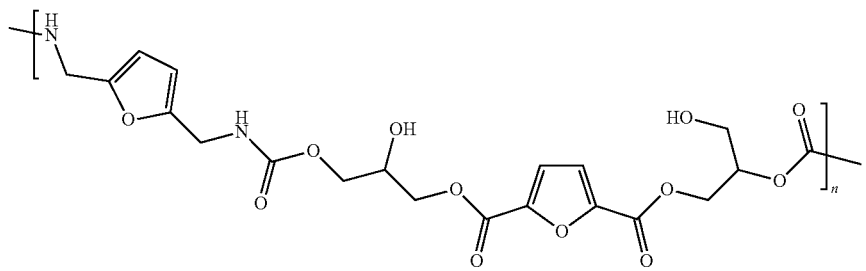

(2)

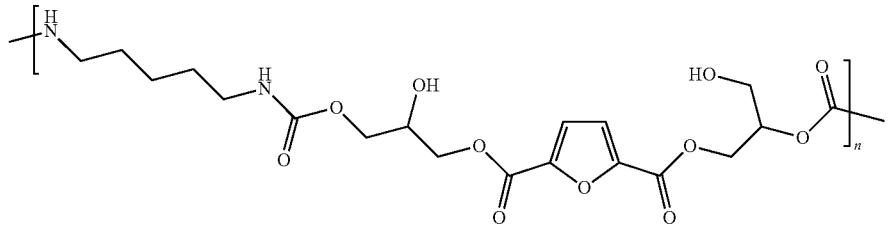

(3)

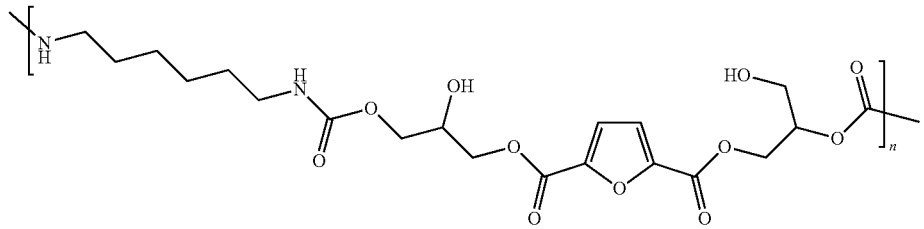

(4)

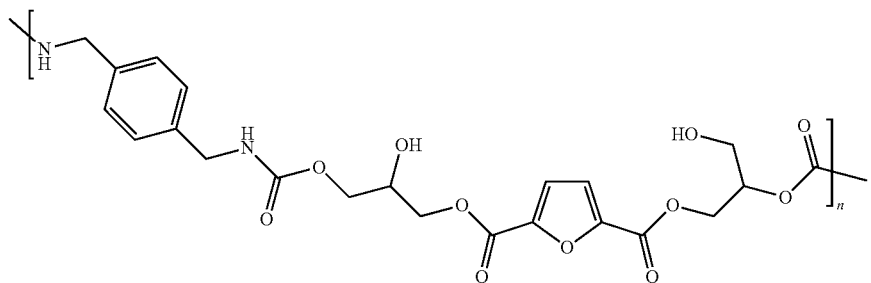

-continued
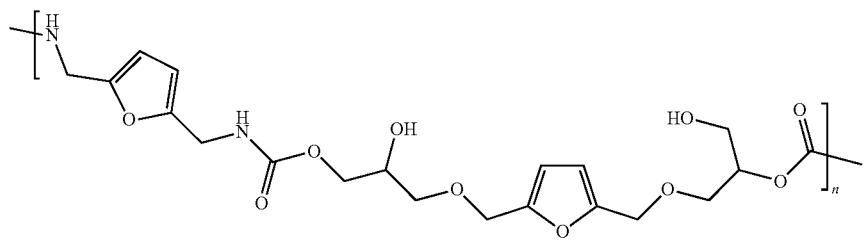
(5)
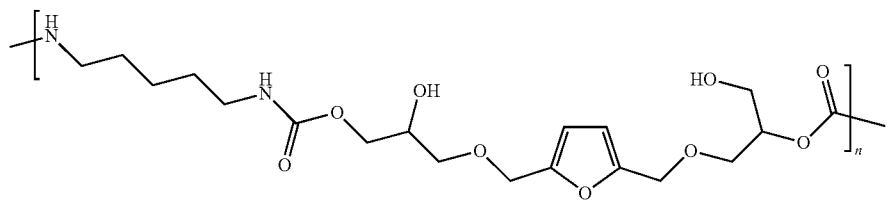
(6)
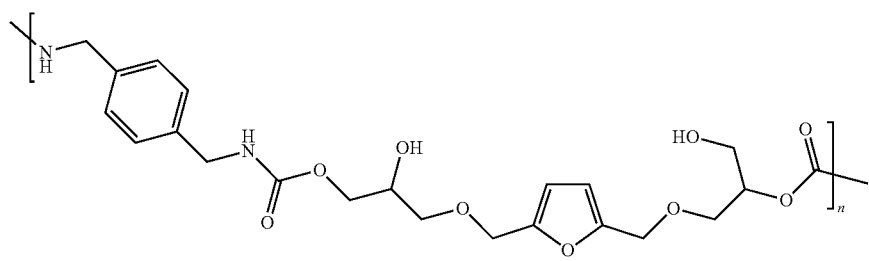
(7)
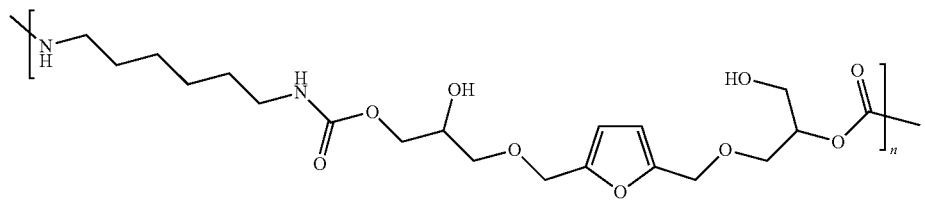
(8)
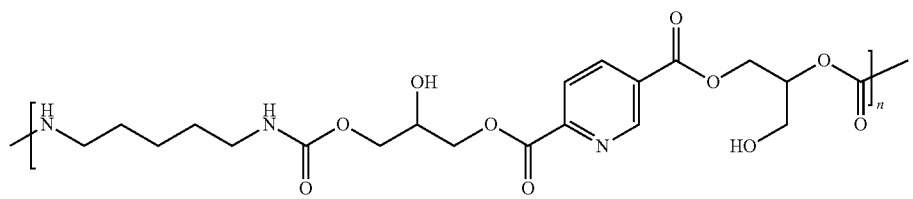
(9)
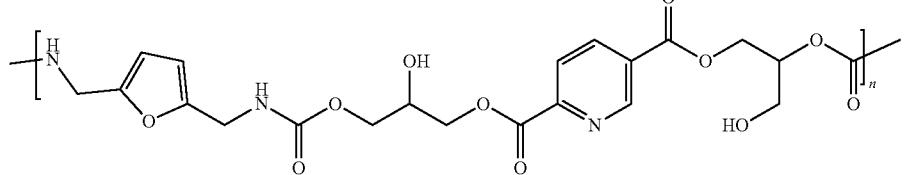
(10)
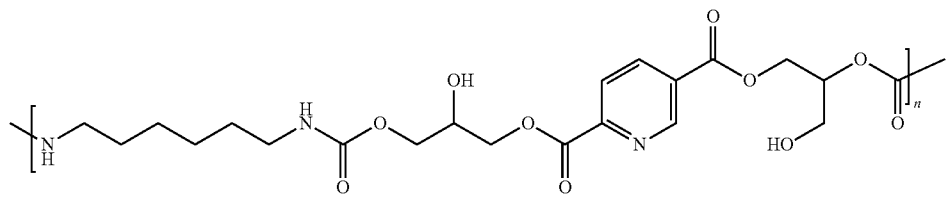
(11)

-continued
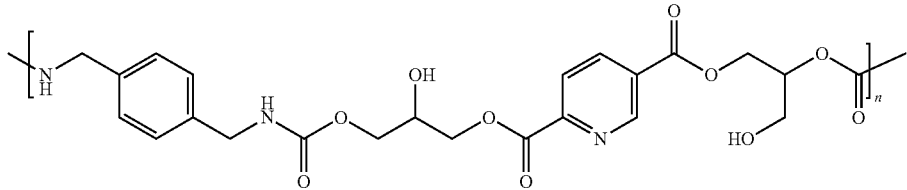
(12)
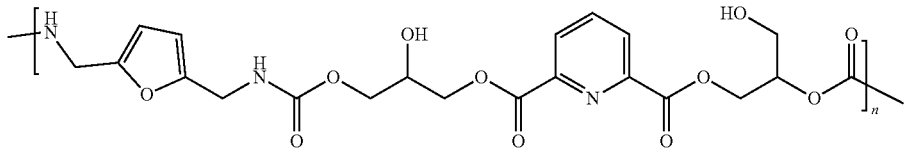
(13)
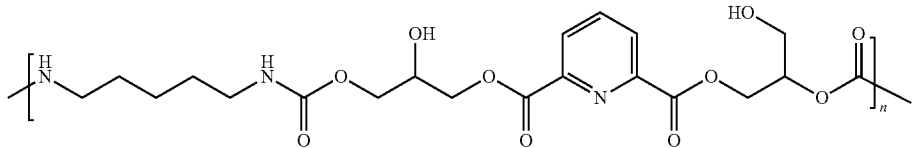
(14)
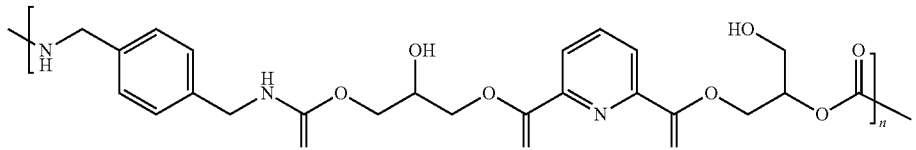
(15)
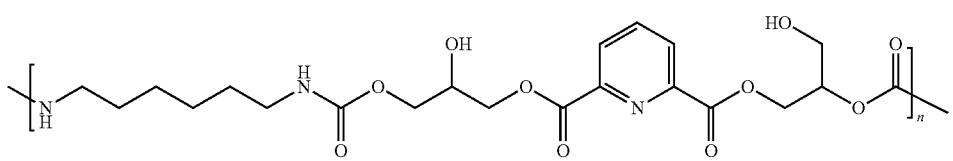
(16)
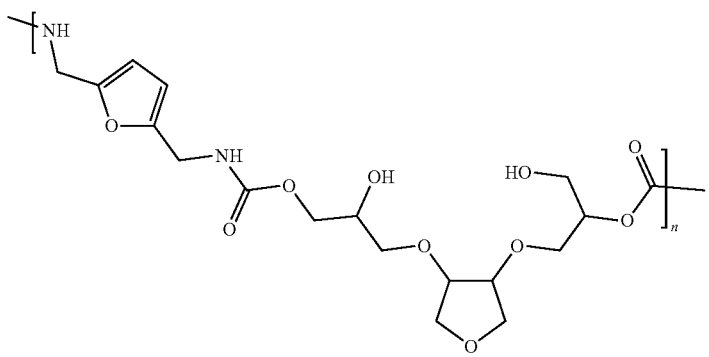
(17)
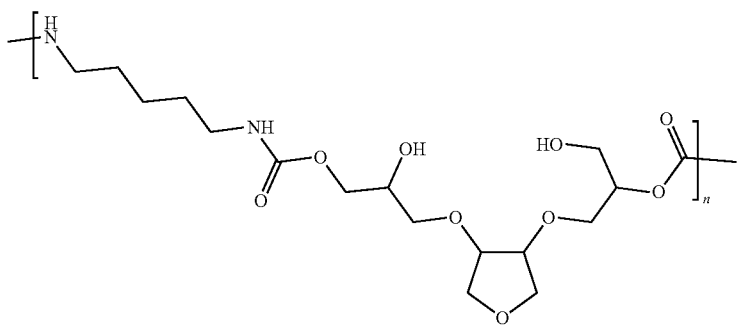
(18)

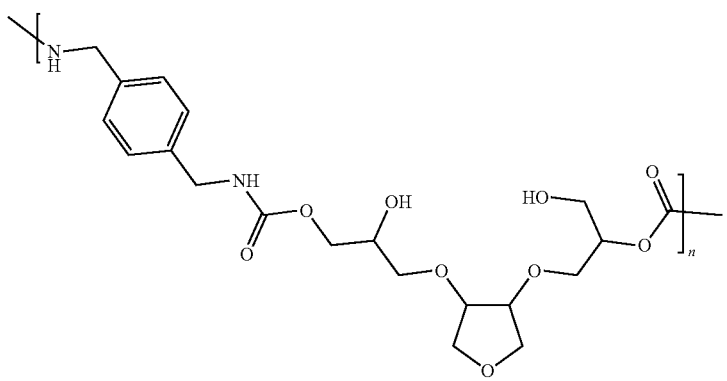

(19)

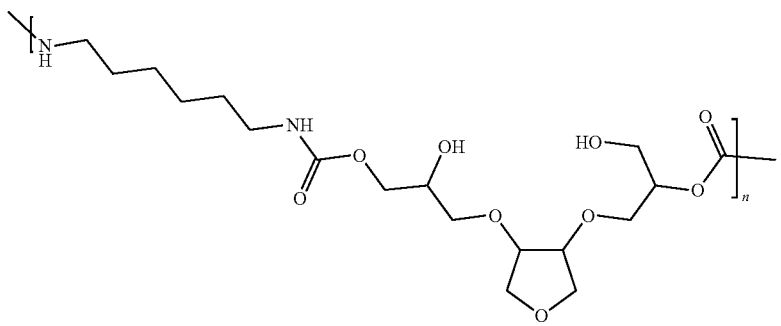

(20)

or a derivative thereof, wherein n is an integer that is indicative of the degree of polymerization.

As may be appreciated, the present disclosure also provides a derivative of the reaction product disclosed above. For example, the derivative may be obtained from functionalising one or more of the hydroxyl groups present in the reaction product, or the derivative may be obtained from grafting a polymer to one or more of the hydroxyl groups and/or to one or more of the furan rings present in the reaction product.

In various embodiments, the derivative of the reaction product is a polymer having a backbone structure represented by a repeating unit of general formula (VIIc):

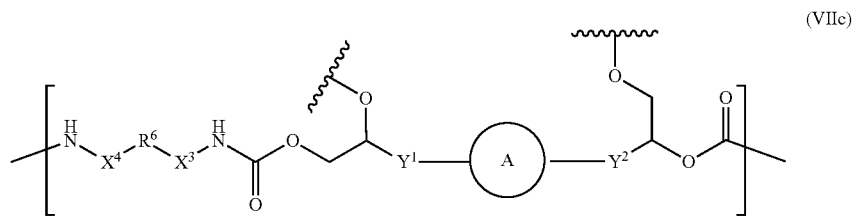

(VIIc)

In various embodiments, when the reaction product undergoes a post polymerisation functionalisation or grafting to form a derivative thereof, the derivative comprises a repeating unit that may be represented by general formula (VIId):

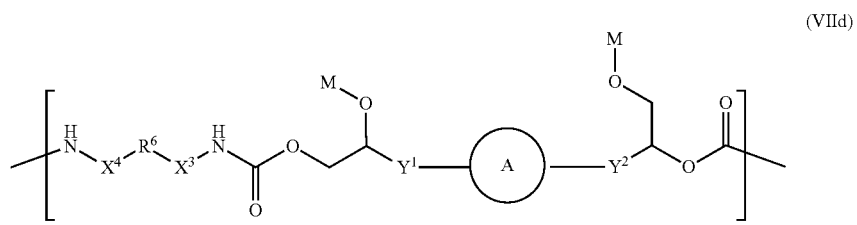

(VIId)

wherein M is independently selected from the group consisting of hydrogen, phosphoryl, alkyl sulfonate, amino, thiol, aminocarbonyl, aminoalkylcarbonyl, thiolcarbonyl, alkyl, alkylcarbonyl, alkenyl, alkenylcarbonyl, arylalkyl, arylalkylcarbonyl, arylalkenyl, arylalkenylcarbonyl, hydroxyl, alkylhydroxycarbonyl, polyester, polyamide, polycarbonate, polysiloxane, peptide, protein and combinations thereof.

In various embodiments, only one M is H, i.e. both M are not H at the same time.

In various embodiments, the alkyl sulfonate may be n-butyl sulfonate, polysiloxane may be selected from polydimethylsiloxane (PDMS) and the polyester may be selected from polylactide (PLA) and polycaprolactone (PCL).

In various embodiments, M is derived from a molecular entity that is capable of reacting with hydroxyl groups present in the reaction product. In some embodiments, the molecular entity is selected from the group consisting of phosphate, sultone, amino acid, peptide, protein (or their derivatives such as amino acid chloride hydrochloride), fatty acid and carboxylic acid (or their derivatives such as fatty acid anhydride and fatty acid chloride). In other embodiments, the molecular entity is selected from the group consisting of polysiloxane (such as polydimethylsiloxane), cyclic amides (such as lactams), cyclic carbonates and cyclic esters. The cyclic esters may be selected from the group consisting of lactide and lactone (such as propiolactone, butyrolactone, and caprolactone).

In various embodiments, a molecular entity selected from tetra-n-butylammonium dihydrogen phosphate, 1,4-butane sultone, glycine chloride hydrochloride, D-phenylalanine chloride hydrochloride, N-acetyl cysteine chloride, butyric acid anhydride, palmitic acid chloride, cinnamic acid chloride, oleic acid chloride, linoleic acid chloride may be used for the functionalisation of the —OH groups of the reaction product, i.e. converting a reaction product having —OH groups to a derivative having —OM groups. In various embodiments, a molecular entity selected from hydroxylated/oxalylated polydimethylsiloxane, lactide and caprolactone may be used for grafting to the —OH groups of the reaction product, i.e. converting a reaction product having —OH groups to a graft polymer having —OM groups. In various embodiments, the graft polymer is represented by the formula: PHU-g-OM.

In various embodiments, $X^4$, $R^6$, $X^3$, $Y^1$, ring A and $Y^2$ in the formulae VIIc and VIId are similar to that described above.

In various embodiments, the derivative of the reaction product is represented by the formula: PHU-g-P, where P is one or more of molecular entity, a monomer, a oligomer, a polymer, peptide or protein.

In various embodiments, one or more molecular entities or polymers containing maleimide end groups may be used for grafting to one or more furan rings present in the reaction product, i.e. converting a reaction product having one or more furan group(s) to a graft polymer having one or more Diels-Alder adduct(s) that resembles the following structure:

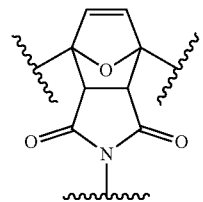

Structure (I)

For example, the derivative may be obtained from grafting a polymer containing maleimide end groups to one or more furan rings present at $X^4$ and/or ring A of the reaction product as disclosed herein.

In various embodiments, the reaction product has a number average molecular weight (Mn) in the range of from about 2,000 g/mol to about 50,000 g/mol, from about 2,500 g/mol to about 40,000 g/mol, from about 3,000 g/mol to about 30,000 g/mol, from about 3,500 g/mol to about 20,000 g/mol, from about 4,000 g/mol to about 19,000 g/mol, from about 4,500 g/mol to about 18,000 g/mol, from about 5,000 g/mol to about 17,000 g/mol, from about 5,500 g/mol to about 16,500 g/mol, from about 6,000 g/mol to about 16,000 g/mol, from about 6,500 g/mol to about 15,500 g/mol, from about 7,000 g/mol to about 15,000 g/mol, from about 7,500 g/mol to about 14,500 g/mol, from about 8,000 g/mol to about 14,000 g/mol, from about 8,500 g/mol to about 13,500 g/mol, from about 9,000 g/mol to about 13,000 g/mol, from about 9,500 g/mol to about 12,500 g/mol, from about 10,000 g/mol to about 12,000 g/mol, from about 10,500 g/mol to about 11,500 g/mol, or about 11,000 g/mol. In some embodiments, the number average molecular weight of the reaction product is about 2,358 g/mol, about 2,473 g/mol, about 2,538 g/mol, about 2,667 g/mol, about 2,695 g/mol, about 3,018 g/mol, about 3,207 g/mol, about 3,413 g/mol, about 3,921 g/mol or about 3,953 g/mol.

In various embodiments, the reaction product has a peak molecular weight (Mp) in the range of from about 1,500 g/mol to about 60,000 g/mol, from about 2,000 g/mol to about 50,000 g/mol, from about 2,500 g/mol to about 40,000 g/mol, from about 3,000 g/mol to about 30,000 g/mol, from about 3,500 g/mol to about 29,000 g/mol, from about 4,000 g/mol to about 28,000 g/mol, from about 4,500 g/mol to about 27,000 g/mol, from about 5,000 g/mol to about 26,500 g/mol, from about 5,500 g/mol to about 26,000 g/mol, from about 6,000 g/mol to about 25,500 g/mol, from about 6,500 g/mol to about 25,000 g/mol, from about 7,000 g/mol to about 24,500 g/mol, from about 7,500 g/mol to about 24,000 g/mol, from about 8,000 g/mol to about 23,500 g/mol, from about 8,500 g/mol to about 23,000 g/mol, from about 9,000 g/mol to about 22,500 g/mol, from about 9,500 g/mol to about 22,000 g/mol, from about 10,000 g/mol to about 21,500 g/mol, from about 10,500 g/mol to about 21,000 g/mol, from about 11,000 g/mol to about 20,000 g/mol, from about 11,500 g/mol to about 19,500 g/mol, from about 12,000 g/mol to about 19,000 g/mol, from about 12,500 g/mol to about 18,500 g/mol, from about 13,000 g/mol to about 18,000 g/mol, from about 13,500 g/mol to about 17,500 g/mol, from about 14,000 g/mol to about 17,000 g/mol, from about 14,500 g/mol to about 16,500 g/mol, from about 15,000 g/mol to about 16,000 g/mol, or about 15,500 g/mol. In some embodiments, the peak molecular weight of the reaction product is about 1,970 g/mol, about 2,050 g/mol, about 2,590 g/mol, about 2,870 g/mol, about 3,380 g/mol, about 3,600 g/mol, about 3,740 g/mol, about 4,900 g/mol, about 5,390 g/mol or about 6,300 g/mol.

In various embodiments, the reaction product has a polydispersity index (PDI) in the range of from about 1.0 to about 5.0, from about 1.1 to about 4.9, from about 1.2 to about 4.8, from about 1.3 to about 4.7, from about 1.4 to about 4.6, from about 1.5 to about 4.5, from about 1.6 to about 4.4, from about 1.7 to about 4.3, from about 1.8 to about 4.2, from about 1.9 to about 4.1, from about 2.0 to about 4.0, from about 2.1 to about 3.9, from about 2.2 to about 3.8, from about 2.3 to about 3.7, from about 2.4 to about 3.6, from about 2.5 to about 3.5, from about 2.6 to about 3.4, from about 2.7 to about 3.3, from about 2.8 to about 3.2, from about 2.9 to about 3.1 or about 3.0.

In various embodiments, the number average molecular weight, peak molecular weight and polydispersity index are determined by gel permeation chromatography using polymethyl methacrylate (PMMA) calibration.

Embodiments of the reaction product represented by general formula (VIIa) and/or (VIIb) disclosed herein are structurally different from traditional polyurethanes at least in that embodiments of the reaction product disclosed herein contain hydroxyl groups. In various embodiments, the reaction products disclosed herein are non-isocyanate polyhydroxyl-urethanes (NIPUs/PHUs) comprising free secondary or primary hydroxyl functional groups in their structure in addition to the carbamate linkages. In various embodiments, the reaction products are hydrophilic. Without being bound by theory, it is believed that the hydroxyl groups present within the reaction product increase the adhesion properties and can be further functionalized or cross-linked. Without being bound by theory, it is also believed that hydrogen bonds will increase the thermal and hydrolytic stability as well as chemical resistance to non-polar solvents.

As compared to known polyurethanes, embodiments of the reaction product disclosed herein have higher degradation temperature and higher chemical stability to hydrolysis. As compared to known polyurethanes, embodiments of the reaction product disclosed herein also have better adhesion properties and can be further functionalized/cross-linked for use in a wide array of applications.

In various embodiments, there is provided a method of preparing the reaction product disclosed herein, the method comprising: reacting one or more compounds represented by general formula (Ia) and/or (Ib) with one or more amine containing compounds to obtain the reaction product.

In various embodiments of the method disclosed herein, the one or more amine containing compound comprises at least two amine functional groups. In various embodiments, the amine containing compound is an aliphatic diamine or an aromatic diamine. The amine containing compound may comprise two, three, four, five, six, seven or eight amine functional groups.

In various embodiments of the method disclosed herein, the amine containing compound comprises a bio-based amine. The bio-based amine is derived from natural resources selected from the group consisting of isosorbide-based diamine, vanillin-based diamine, grapeseed oil-based polyamine, fatty acid based diamine, pentaerythritol-based triamine.

In various embodiments of the method disclosed herein, the amine containing compound is selected from the group consisting of furan-2,5-diyldimethanamine (FBA), xylene diamine (XDA), diaminopentane (DAP), hexamethylenediamine (HDA), isophorone diamine, ether diamine, polyether diamine, dimer diamine and lysine.

In various embodiments, the method of preparing a compound represented by general formula (Ia) and/or (Ib) and the method of preparing a reaction product represented by general formula (VIIa) and/or (VIIb) disclosed herein are devoid of a step containing the use of isocyanates as a reactant.

In various embodiments, the methods disclosed herein are advantageous over existing technologies at least in that the aromatic and aliphatic cyclic biscarbonate monomers and polyhydroxyurethanes produced from the polymerisation of said monomers are bio-based/bio-derived. In various embodiments of the method disclosed herein, the amine precursors used for the preparation of the reaction product are derived from a bio-based source. In various embodiments therefore, the reaction products disclosed herein are innocuous biocompatible polymers, making them attractive as alternative sustainable materials for future applications such as in coatings, additives, adhesives, film formers, pigment dispersing agents and oil thickeners.

In various embodiments, the methods disclosed herein is less toxic, relatively safer and more environmentally friendly than the method described in Scheme 1 below.

Scheme 1. Method of synthesizing polyurethane from 4,4'-methylene diphenyl diisocyanate (MDI) and ethane-1,2-diol

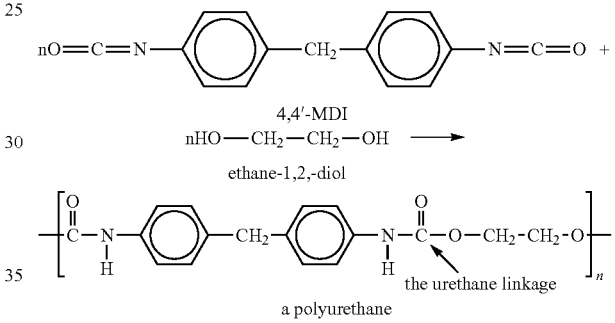

In various embodiments, the method of preparing a reaction product represented by general formula (VIIa) and/or (VIIb) has a monomer conversion % of no less than about 45%, no less than about 50%, no less than about 55%, no less than about 60%, no less than about 65%, no less than about 70%, no less than about 75%, no less than about 80%, no less than about 85%, or no less than about 90%.

In various embodiments, the method further comprises a step of functionalising the hydroxyl groups present in the reaction product. In various embodiments, the step of functionalising the hydroxyl groups comprises a step whereby the hydroxyl groups are phosphorylated by a phosphate, a step whereby the hydroxyl groups are sulfonated by a sultone or a step where the hydroxyl groups undergo esterification with amino acids, peptides, proteins, (or their derivatives such as amino acid chloride hydrochloride), carboxylic acids (or their derivatives such as acid chloride or anhydride) fatty acids, (or their derivatives such as fatty acids chloride or fatty acids anhydride).

In various embodiments, the method further comprises a step of grafting a polymer from the hydroxyl groups present in the reaction product to obtain a graft polymer. In various embodiments, the step of grafting comprises ring opening polymerisation of cyclic amides (such as lactams), cyclic carbonates and cyclic esters. The cyclic esters may be selected from the group consisting of lactide and lactone (such as propiolactone, butyrolactone, and caprolactone). In various embodiments, the step of grafting comprises grafting polysiloxane (such as hydroxylated/oxalylated polydimethylsiloxane) to the —OH groups present in the reaction product.

In various embodiments, the method further comprises a step of grafting a polymer containing maleimide end group(s) to the furan rings present in the reaction product to obtain a graft polymer. In various embodiments, the step of grafting comprises Diels-Alder reaction(s) between the maleimide end group(s) of the polymer and the furan ring(s) of the reaction product. The furan ring(s) may be present at $X^4$ and/or ring A of the reaction product.

In various embodiments, the method further comprises a step of functionalising one or more hydroxyl groups present in the reaction product disclosed herein or polyhydroxyurethanes that are obtained through the reaction between one or more bis/multi-carbonates and an amine containing compound.

In various embodiments, the method further comprises a step of grafting a polymer to one or more hydroxyl groups present in the reaction product disclosed herein or polyhydroxyurethanes that are obtained through the reaction between one or more bis/multi-carbonates and an amine containing compound.

In various embodiments, the functionalised or grafted polymer has one or more of the following properties: solubility or dispersibility in water, solubility or dispersibility in oil, photo or thermo or redox or pH response and crosslinking ability under air, photo, thermal or ionic conditions.

EXAMPLES

Example embodiments of the disclosure will be better understood and readily apparent to one of ordinary skill in the art from the following examples, tables and if applicable, in conjunction with the figures.

The examples describe a method of preparing a compound and a method of preparing a reaction product of said compound from a bio-based source in an environmentally benign process in accordance with various embodiments of the present disclosure. Broadly, the general concept of methods disclosed herein may be illustrated in FIG. 7, FIG. 8 and FIG. 9 as follows.

Figure 7:
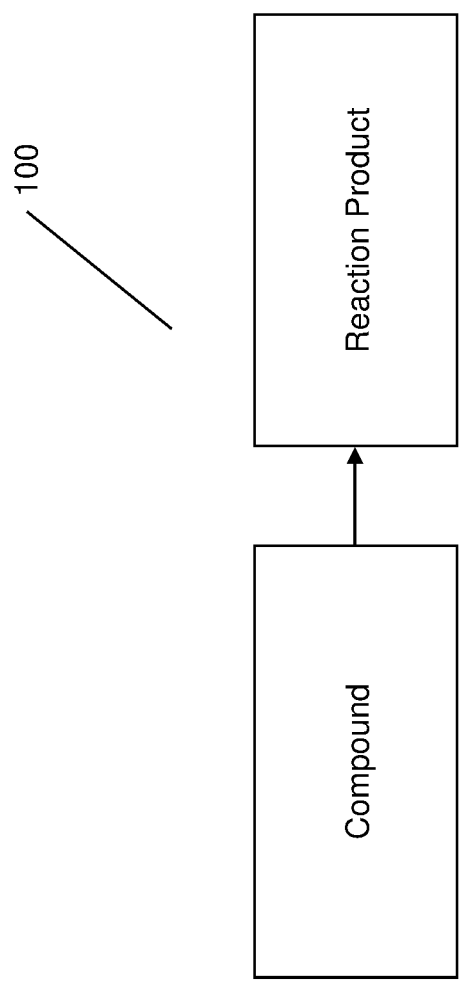
FIG. 7 is a schematic flowchart 100 for illustrating a method of preparing a reaction product represented by general formula (VIIa) and/or (VIIb) from a bio-based source in accordance with various embodiments disclosed herein.

Referring to FIG. 7, it can be seen that a reaction product represented by general formula (VIIa) and/or (VIIb) and/or (VIIc) and/or (VIId) and/or PHU-g-P (for example, any one of polymers (1)-(20) or a derivative thereof described herein) may be prepared from a compound represented by general formula (Ia) and/or (Ib) (for example any one of FBC-1, FBC-2, PBC, PBC-2 and HFBC described herein) which in turn may be optionally derived from a bio-based source (for example, lignin, hexose, glucose and erythriol disclosed herein).

Figure 8:
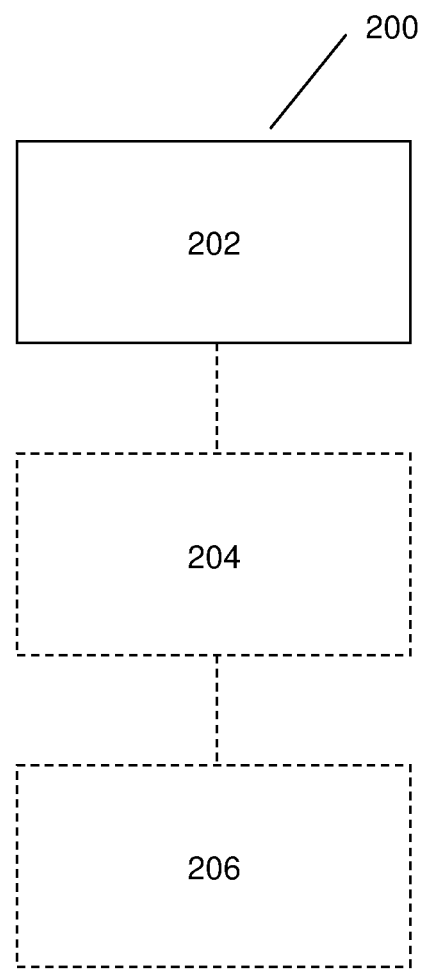
FIG. 8 is a schematic flowchart 200 for illustrating a method of preparing a compound represented by general formula (Ia) and/or (Ib) in accordance with various embodiments disclosed herein.

Referring now to FIG. 8, there is shown a schematic flowchart 200 for illustrating a method of preparing a compound represented by general formula (Ia) and/or (Ib) (for example any one of FBC-1, FBC-2, PBC, PBC-2 and HFBC described herein). At step 202, a precursor compound represented by general formula (VI) (for example any one of HMF, FDM, FDCA, FBA, pyridine-2,5-dicarboxylic acid, pyridine-2,6-dicarboxylic acid and 1,4-anhydroerythritol described herein), optionally derived from a bio-based source. At step 204, the method further comprises converting the precursor to said compound through one or more chemical reactions, wherein at least one of the one or more chemical reactions is carried out in the presence of a halogenated compound. At step 206, the method further comprises reducing or oxidising the precursor compound (for example, when the precursor is HMF, HMF may be reduced to FDM or oxidized to FDCA) prior to undergoing one or more chemical reactions in the presence of a halogenated compound (i.e. a compound containing a halogen such as but not limited to thionyl chloride, epichlorohydrin allylbromide). As will be appreciated, the choice of the halogenated compound may varied depending on the identity of the precursor compound. The dotted lines of the boxes containing steps 204 and 206 indicate that these steps may be absent in some embodiments of the present disclosure depending on factors such as which part of a broader process the method pertains to and/or the identity of the bio-based source and/or the identity of the precursor compound desired.

Figure 9:
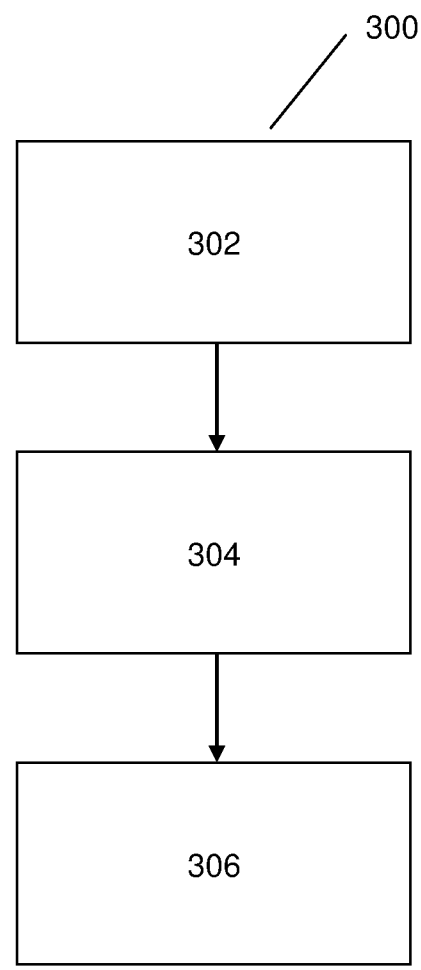
FIG. 9 is a schematic flowchart 300 for illustrating a method of preparing a reaction product represented by general formula (Vila) and/or (VIIb) in accordance with various embodiments disclosed herein.

Turning to FIG. 9, there is shown a schematic flowchart 300 for illustrating a method of preparing a reaction product in the form of a polymer represented by general formula (VIIa) and/or (VIIb) and/or (VIIc) and/or (VIId) and/or PHU-g-P in accordance with various embodiments disclosed herein.

At step 302, one or more compounds in the form of a first monomer type represented by general formula (Ia) and/or (Ib) are provided. At step 304, one or more amine containing compounds in the form of a second monomer type are provided. At step 306, the first and second monomer types are reacted to obtain a polymer represented by general formula (VIIa) and/or (VIIb).

In addition, the following examples further show that embodiments of the presently disclosed method provide a green and sustainable strategy to produce cyclic biscarbonates and polyhydroxyurethanes as use of toxic isocyanates and phosgene may be avoided.

As will be shown in the following examples, embodiments of the presently disclosed method synthesize new aliphatic and aromatic cyclic biscarbonates and new polyhydroxyurethanes that are capable of addressing several problems of conventional methods used in the art. The polyhydroxyurethanes disclosed herein are innocuous biocompatible polymers, making them attractive as greener, safer, bio-renewable and sustainable materials for a wide array of applications. It should be appreciated that the examples provided below are meant to be merely illustrative and not in any way meant to be exhaustive or restrictive.

Bio-Based Cyclic Biscarbonate Monomers

Several biscarbonate monomers have been developed from bio-based platform chemicals such as 5-hydroxymethylfurfural (HMF), 1,4-anhydroerythritol, pyridine dicarboxylic acid and glycerol. Renewable C-1 feedstock such as $CO_2$ was also utilized towards creating cyclic carbonate structures. The synthesis protocols for the monomers and the polyhydroxy urethane polymers are summarized in Schemes 2.1, 2.2 and 2.3, and explained below.

Scheme 2.1. Synthesis of Bis-carbonate monomers from HMF derived from hexoses

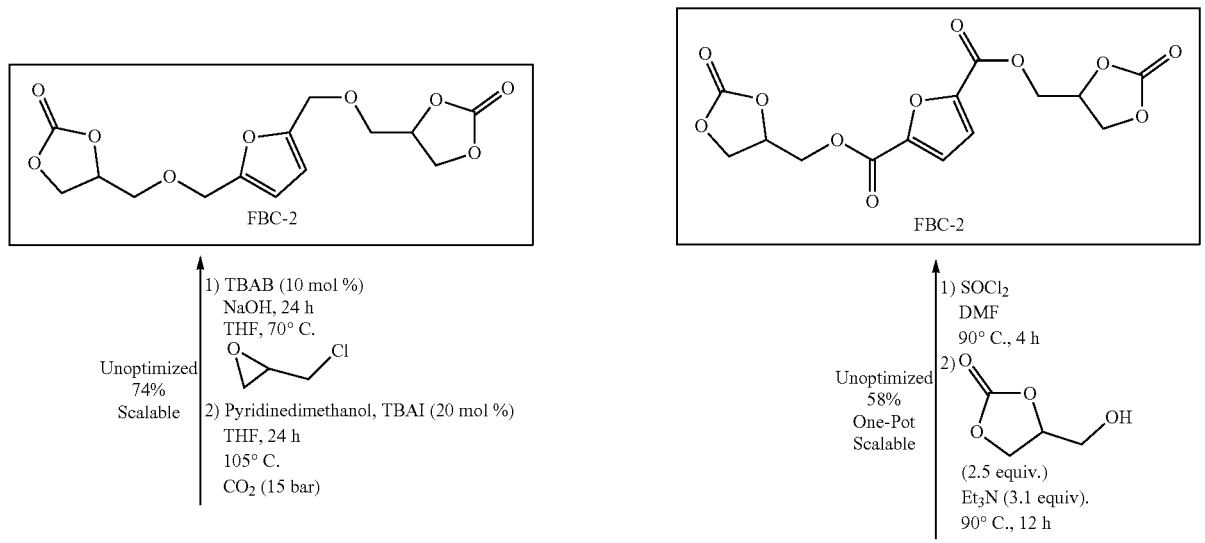

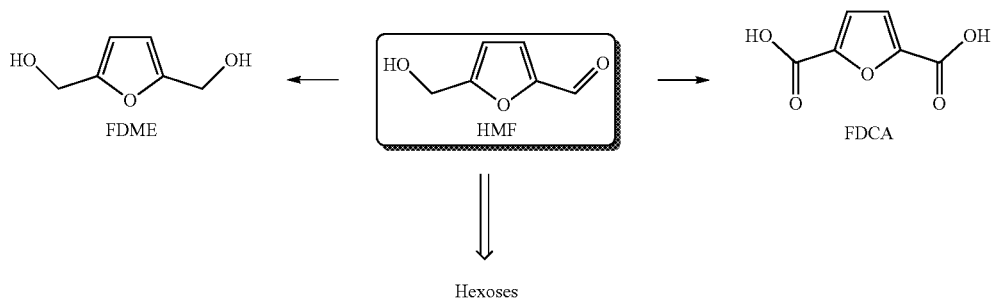

Scheme 2.2. Synthesis of Bis-carbonate monomers from pyridine dicarboxylic acid derived from lignin
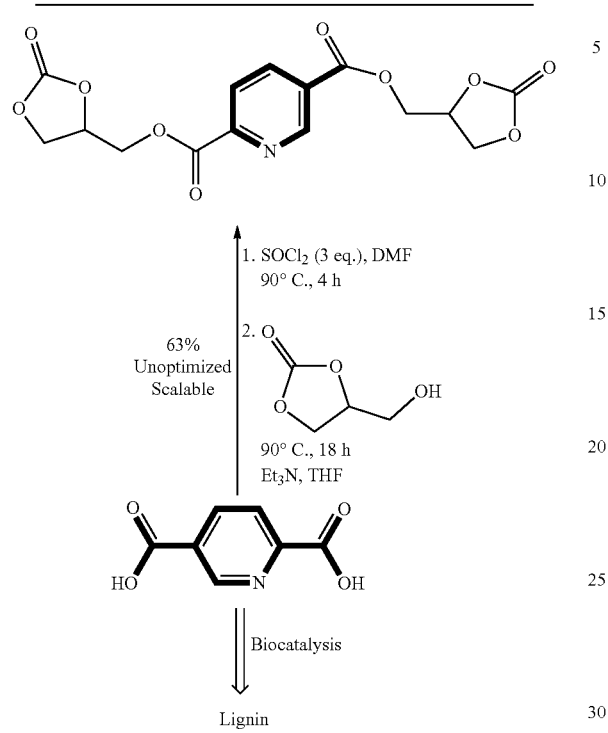
Scheme 2.3. Synthesis of Bis-carbonate monomers from 1,4-anhydroerythritol derived from glucose and/or erythritol
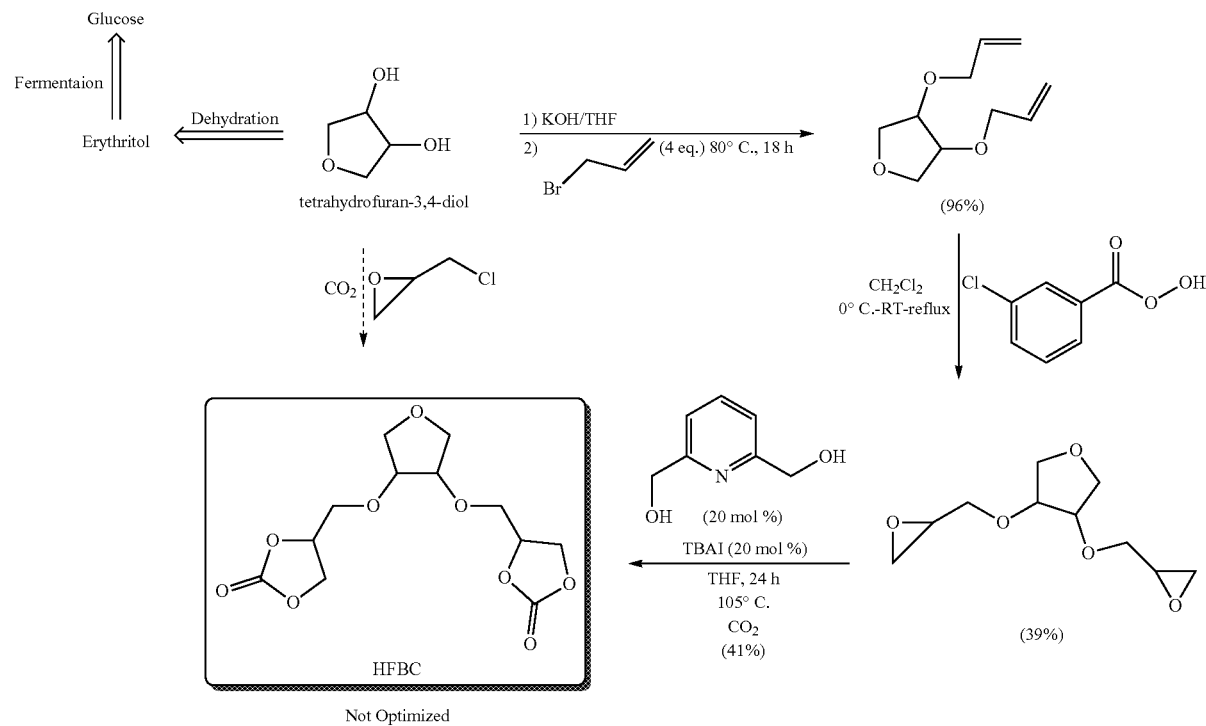

Furan Based Cyclic Biscarbonate Monomers

The initial synthetic focus was based on the bio-feedstock 5-hydroxymethylfurfural (HMF), which is manufactured by the acid-catalyzed dehydration of hexoses. Recent commercialization of a 20 tons/year scale by AVA Biochem in Muttenz, Switzerland adds to its feedstock security. HMF derived bis-carboxylic acid (FDCA) and bis-diol (FDM) can be good linkers for the synthesis of bis-cyclic carbonate monomers. FDCA is an oxidation product of HMF. Companies such as Aventium (40 tons/y pilot scale), Synbias, Carbone Scientific Tokyo Chemical Industry, V & V Pharma Industries, Chemsky and Good Scents Company are involved in the pilot scale production of FDCA. FDM is a reduction product of HMF and could be available commercially in future. The Bis-carbonate monomers (Scheme 3) can be conveniently synthesized from HMF derivatives using simple organic transformations through ester, ether, amine, amide, or carbamate linkages.

Furan based cyclic biscarbonate with ester linkage can be synthesized from FDCA or its acid chloride or esters with glycerol carbonate via by standard esterification or transesterification protocols e.g. catalytic esterification/transesterification or by using coupling agents. Furan containing cyclic carbonates with ether linkages can be synthesized from corresponding furan containing diols via alkylations using a carbonate containing halide or pseudo halide or epoxide containing halide or pseudo halide followed by $CO_2$ insertion.

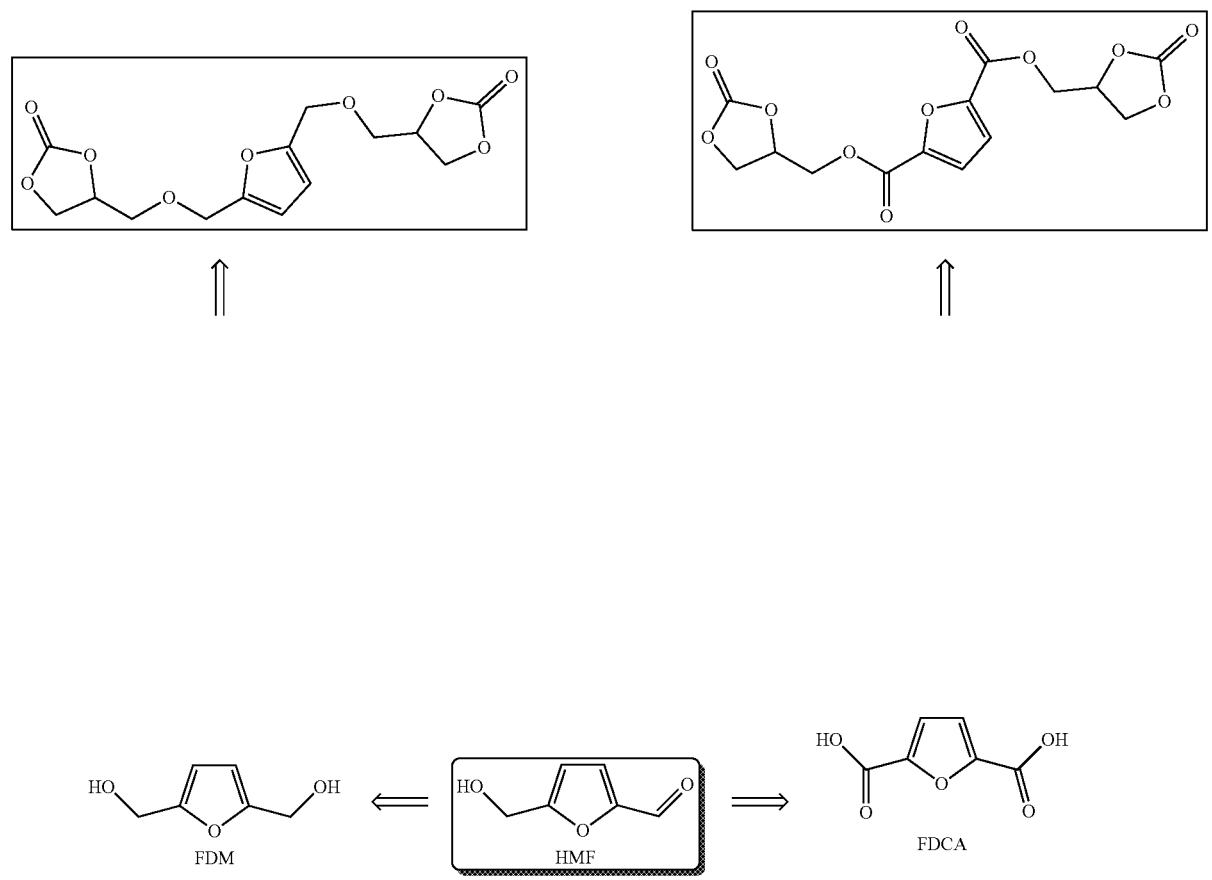

Scheme 3. Synthesis of Bis-carbonate monomers from HMF (simplified)

Example 1

Synthesis of Furan Based Cyclic Biscarbonate with Ester Linkage

Furan based cyclic biscarbonate with ester linkage was synthesized from FDCA by a one pot esterification with glycerol carbonate as shown in Scheme 4.

Scheme 4. Synthesis of Furan based bis-Cyclic-carbonate with Ester Linkage (FBC-1)

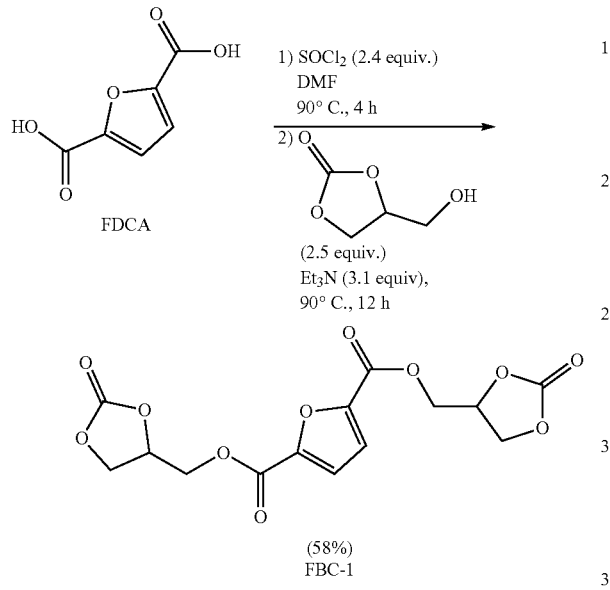

(58%)
FBC-1

To a round bottom flask connected with condenser, FDCA (40 mmol, 6.24 g), $SOCl_2$ (96 mmol, 7 mL) and 5 mL of dimethylformamide (DMF) were added and the reaction was carried out at 90° C. under argon for 4 h. The reaction mixture was then cooled down to room temperature. $Et_3N$ (125 mmol, 20 mL) and glycerol carbonate (100 mmol, 11.8 g in 25 mL of dry THF) were added slowly and the mixture was further heated to 90° C. overnight. After the reaction, the excess amount of $Et_3N$, $SOCl_2$ and DMF were removed under high vacuum. The product was isolated as a white solid, filtered and washed with water (100 mL, 2 times) and with $Et_2O$ (100 mL, 2 times) to give 8.24 g (23.13 mmol) of pure bis((2-oxo-1,3-dioxolan-4-yl)methyl)furan-2,5-dicarboxylate (58%) which was characterized by $^1H$, $^{13}C$-NMR and HRMS. $^1$H-NMR (DMSO, 400 MHz): 7.42 (s, 2H), 5.16 (m, 2H), 4.6 (m, 6H), 4.4 (dd, J=8.6, 6.1 Hz, 2H). $^{13}C$ NMR (DMSO, 100 MHz): =156.7, 154.6, 145.8, 119.6, 74.1, 67.0, 64.5. HRMS (ESI) (M+H)$^+$ m/z Calcd. For $C_{14}H_{12}O_{11}$: 357.0452. Found: 357.0459.

Example 2

Synthesis of Furan Based Cyclic Biscarbonate with Ether Linkage

The novel cyclic biscarbonate 4,4'-(((furan-2,5-diylbis(methylene))-bis(oxy))bis(methylene)) bis(1,3-dioxolan-2-one), FBC-2, was synthesized by using a two-step protocol in multi gram scale starting from FDM as shown in Scheme 5.

Scheme 5. Synthesis of Furan based bis-Cyclic-carbonate with Ether Linkage (FBC-2)

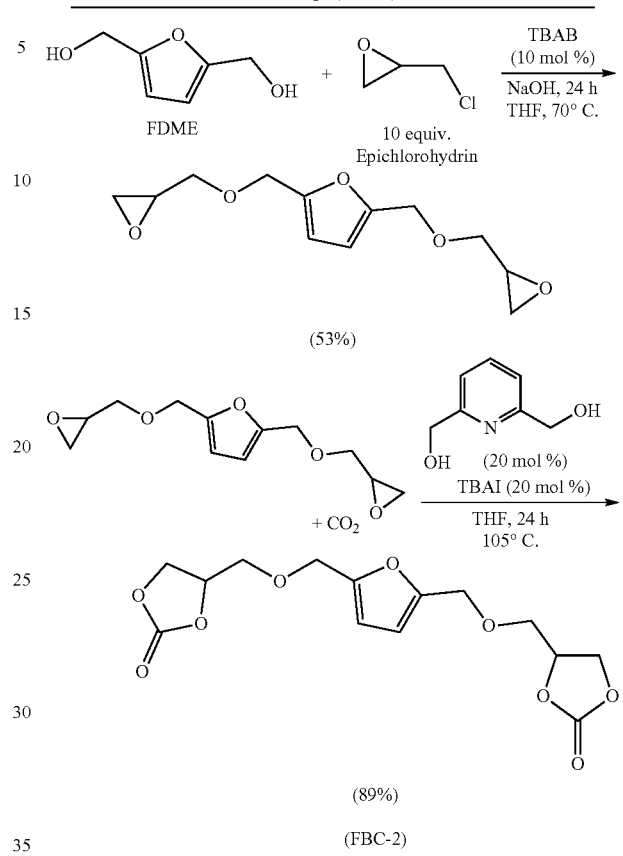

(89%)
(FBC-2)

In the first step, a solution of furandimethanol (FDM) (20 mmol, 2.56 g), epichlorohydrin (200 mmol, 18.5 g) and tetrabutylammonium bromide (TBAB) (20 mol %, 2.57 g) in THF (30 mL) was added into aqueous NaOH (20 g in 20 mL). This mixture was heated and stirred at 70° C. for 24 h. After the reaction, the reaction mixture was diluted with 50 mL of water and the product was extracted into EtOAc (100 mL, 3 times) and the combined organic layers were dried over $MgSO_4$. After evaporation of the solvent and column chromatography of the crude reaction mixture, the diepoxy product 2,5-bis((oxiran-2-ylmethoxy)-methyl)furan was isolated in 4.32 g (18 mmol), 89% (yellow oil) and characterized by NMR and HRMS as follows. $^1$H-NMR (CDCl$_3$, 400 MHz): 6.27 (s, 2H), 4.48 (q, J=8.3 Hz, 4H), 3.74 (dd, J=11.5, 3.1 Hz, 2H), 3.42 (dd, J=11.5, 5.8 Hz, 2H), 3.13 (m, 2H), 2.76 (dd, J=5.1, 4.2 Hz, 2H), 2.58 (dd, J=5.0, 2.7 Hz, 2H). $^{13}C$ NMR (CDCl$_3$, 100 MHz): δ=151.9, 110.3, 70.8, 65.3, 50.8, 44.3. HRMS (ESI) (M+H)$^+$ m/z Calcd. For $C_{12}H_{16}O_5$: 258.1336. Found: 258.1344.

In the second step, the diepoxy product 2,5-bis((oxiran-2-ylmethoxy)-methyl)furan (18 mmol, 4.32 g), tetrabutyl ammonium iodide (TBAI) (20 mol %, 3.6 mmol) and pyridinedimethanol (20 mol %, 3.6 mmol) were dissolved in 12 mL of dry THF, transferred into a Parr reactor and pressurized with $CO_2$ up to 150 psig after purging with $N_2$ followed by $CO_2$. The reaction was carried out under stirring at 105° C. for 24 h. After the reaction, the reactor was cooled to room temperature and depressurized. The reaction mixture was collected, the solvent evaporated and the product was purified by column chromatography. The bicarbonate product 4,4'-(((furan-2,5diylbis(methylene))bis(oxy))-bis(methylene))bis(1,3-dioxolan-2-one) was isolated as a white solid (5.1 g, 15.53 mmol, 86% yield) and characterized by $^1$H, $^{13}$C-NMR and HRMS as follows. $^1$H-NMR (CDCl$_3$, 400 MHz): 6.29 (s, 2H), 4.81 (m, 2H), 4.48 (m, 6H), 4.33 (dd, J=8.4, 6.0 Hz, 2H), 3.72 (ddd, J=11.1, 3.6, 2.0 Hz, 2H), 3.62 (dd, J=11.1, 3.8 Hz, 2H). $^{13}$C NMR (CDCl$_3$, 100 MHz): δ=155.1, 151.6, 110.8, 75.2, 68.8, 66.3, 65.4. HR-MS (ESI) (M+Na)$^+$ m/z Calcd. for C$_{14}$H$_{16}$O$_9$Na: 351.0687. Found: 351.0695.

Example 3

Synthesis of Tetrahydrofuran Based Bis-Cyclic-Carbonate with Ether Linkage

Bioderived aliphatic cyclic diols such as 1,4-anhydroerythritol can be another class of linkers to form aliphatic cyclic biscarbonates with tetrahydrofuran backbone. An aliphatic bio-based cyclic biscarbonate 4,4'-(((tetrahydrofuran-3,4-diyl)bis(oxy))bis(methylene))bis(1,3-dioxolan-2one) was synthesized from 1,4-anhydroerythritol, which was derived from the bio-feedstock erythritol. The synthetic protocol for converting 1.4-anhydroerythritol to 4,4'-(((tetrahydrofuran3,4-diyl)bis(oxy))bis(methylene))-bis(1,3-dioxolan-2-one) is shown in Scheme 6.

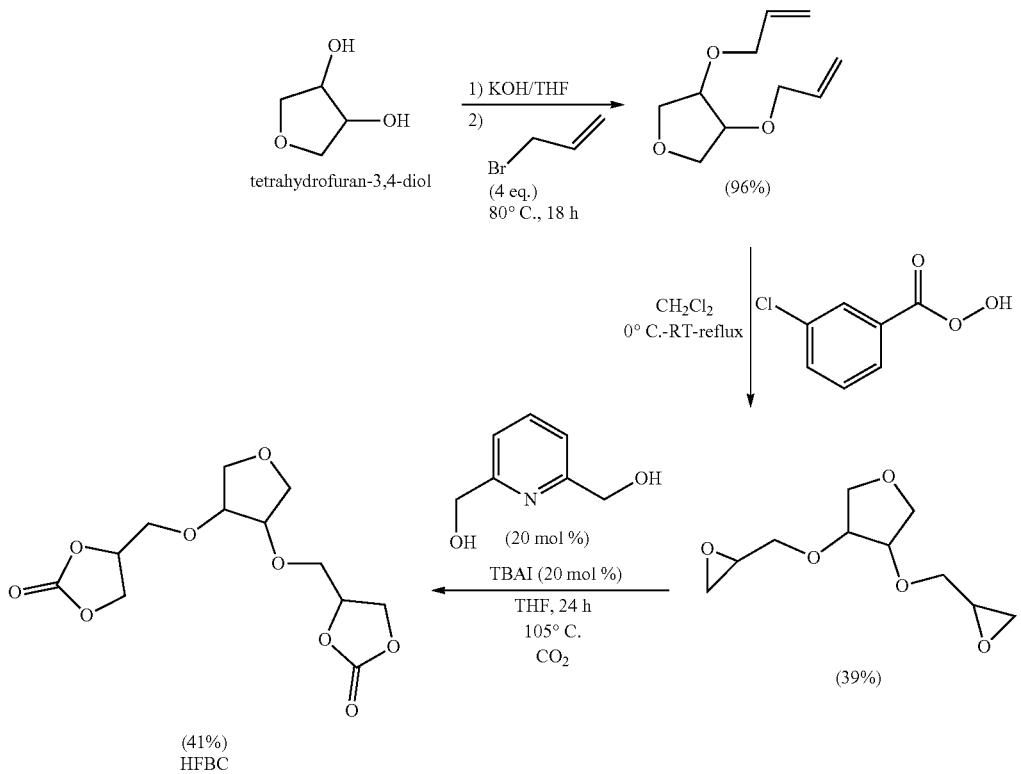

Scheme 6. Synthesis of tetrahydrofuran based bis-Cyclic-carbonate with ether Linkage (HFBC)

1,4-anhydroerithritol (20 mmol, 2.08 g) was added into a mixture of KOH/THF (100 mmol (5.6 g)/40 mL). Allylbromide (60 mmol, 7.26 g) was added slowly into the mixture. This mixture was heated and stirred at 80° C. (under refluxing) for 18 h. After reaction, the crude reaction mixture was diluted with water (50 mL) and extracted with EtOAc (100 mL, 3 times). The combined organic layers were then dried using MgSO$_4$, solvent evaporated and the product 3,4-bis(allyloxy)tetrahydrofuran was isolated by column chromatography in 3.53 g, 19.2 mmol (96%) as an yellow oil and characterized by $^1$H-NMR, $^{13}$C-NMR and HRMS. $^1$H-NMR (CDCl$_3$, 400 MHz): 6.04-5.79 (m, 2H), 5.37-5.11 (m, 4H), 4.09 (m, 4H), 4.00 (m, 2H), 3.97-3.89 (m, 2H), 3.80 (m, 2H). $^{13}$C NMR (CDCl$_3$, 100 MHz): δ=134.8, 117.4, 77.7, 71.4, 70.5. HR-MS (ESI) (M+H)$^+$ m/z Calcd. for C$_{10}$H$_{17}$O$_3$: 185.1172. Found: 185.1172.

In the second step, a solution of 3,4-bis(allyloxy)tetrahydrofuran (10 mol, 1.84 g) in dichloromethane (30 mL) was cooled down to 0° C. followed by the addition of m-chloroperoxybenzoic acid (30 mmol, 5.2 g) under stirring. The reaction mixture was allowed to stir and the temperature was slowly brought to room temperature (22° C.) during 6 h. Another portion of m-chloroperoxybenzoic acid (30 mmol) was added into the reaction mixture and the reaction mixture refluxed overnight. The reaction was cooled down to room temperature, 50 mL of water was added and the crude mixture was extracted with EtOAc (100 mL, 3 times). The combined organic layers were dried over MgSO$_4$, solvent evaporated and the product 3,4-bis(oxiran-2-ylmethoxy)tetrahydrofuran was isolated as a diastereomeric mixture by column chromatography to yield 0.841 g, 3.9 mmol (39%) of product as a colourless oil and was characterized by $^1$H NMR, $^{13}$C-NMR and HRMS. $^1$H-NMR (CDCl$_3$, 400 MHz): 4.09-3.97 (m, 2H), 3.94-3.68 (m, 6H), 3.43 (ddd, J=28.0, 11.8, 5.9 Hz, 2H), 3.11 (ddq, J=5.5, 4.0, 2.7 Hz, 2H), 2.73 (m, 2H), 2.61-2.48 (m, 2H). $^{13}$C NMR (CDCl$_3$, 100 MHz): δ=78.9-78.7, 71.3-71.0, 70.5-70.0, 50.9-50.7, 44.1-44.0. HR-MS (ESI) (M+NH$_4$)$^+$ m/z Calcd. for C$_{10}$H$_{20}$NO$_5$: 234.1336 Found: 234.1343.

In the third step, 3,4-bis(oxiran-2-ylmethoxy)tetrahydrofuran (1.5 mmol, 324 mg), tetrabutyl ammonium iodide (20 mol %, 110 mg) and pyridine-2,6-diyldimethanol (20 mol %, 42 mg) were dissolved in 12 mL dry THF in a Parr reactor and pressurized with CO$_2$ (up to 150 psi) after purging with N$_2$ followed by CO$_2$. This mixture was heated at 105° C. under stirring for 24 h. After reaction, the Parr reactor was cooled down to room temperature and depressurized. The reaction mixture was collected, the solvent evaporated and the product 4,4'-(((tetrahydrofuran-3,4-diyl)bis(oxy))bis (methylene))-bis(1,3-dioxolan-2-one) was isolated as a diastereomeric mixture by column chromatography in 0.187 g, (0.615 mmol, 41% yield) as an yellow oil and characterized by $^1$H, $^{13}$C-NMRs and MS. $^1$H-NMR (CDCl$_3$, 400 MHz): 4.84 (m, 2H), 4.52 (m, 2H), 4.40 (m, 2H), 4.09 (m, 2H), 3.95 (m, 2H), 3.61-3.82 (m, 6H). $^{13}$C NMR (CDCl$_3$, 100 MHz): δ=155.1-155.0, 79.4-79.0, 75.3-75.0, 70.5-70.1, 69.8-69.3, 66.1-66.0. HR-MS (ESI) (M+H)$^+$ m/z Calcd. for C$_{12}$H$_{17}$O$_9$: 305.0867. Found: 305.0879.

Pyridine Containing Cyclic Carbonates

Pyridine containing cyclic biscarbonate with ester linkage can be synthesized from pyridine containing dicarboxylic acids or esters with glycerol carbonate via standard esterification by or transesterification protocols e.g. catalytic esterification/transesterification or by using coupling agents. Pyridine containing cyclic carbonates with ether linkages can be synthesized from corresponding furan containing diols via alkylations using a cyclic carbonate containing halide or pseudo halide or epoxide containing halide or pseudo halide followed by CO$_2$ insertion.

Example 4

Synthesis of Pyridine Based Cyclic Biscarbonate with Ester Linkage

The synthetic protocol for converting pyridine-2,5-dicarboxylic acid to bis((2-oxo-1,3-dioxolan4-yl)methyl)-pyridine-2,5-dicarboxylate is shown in Scheme 7.

Scheme 7. Synthesis of pyridine based cyclic biscarbonate with ester linkage (PBC)

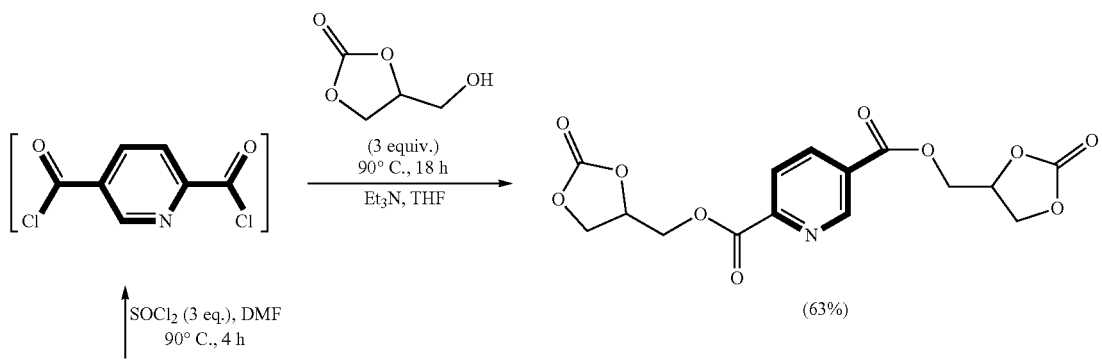

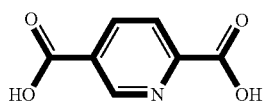

To a round bottom flask connected with condenser, pyridine-2,5-dicarboxylic acid (20 mmol, 3.34 g), SOCl$_2$ (60 mmol, 7.14 g) and 5 mL of DMF were added and the reaction was carried out at 90° C. under argon for 4 h. The reaction mixture was then cooled down to room temperature, Et$_3$N (6 equiv., 16.8 mL) and glycerol carbonate (80 mmol, 9.45 g in 12 mL of THF) were added slowly and was further heated at 90° C. overnight. After the reaction, the excess amount of Et$_3$N, SOCl$_2$ and solvent were removed under vacuum. The product bis((2-oxo-1,3-dioxolan-4-yl)methyl)pyridine-2,5-dicarboxylate was isolated as a white solid, filtered and washed with water (30 mL, 2 times) and with Et$_2$O (30 mL, 2 times) to give 4.61 g (12.6 mmol) of pure product (63%) which was characterized by $^1$H, $^{13}$C-NMR and HRMS. $^1$H-NMR (CDCl$_3$, 400 MHz): 9.19 (dd, J=2.1, 0.8 Hz, 1H), 8.49 (dd, J=8.2, 2.2 Hz, 1H), 8.21 (dd, J=8.1, 0.8 Hz, 1H), 5.36-5.05 (m, 2H), 4.84-4.31 (m, 8H). $^{13}$C NMR (CDCl$_3$, 100 MHz): δ=168.8, 168.6, 159.9, 159.8, 155.5, 155.4, 143.8, 133.2, 130.3, 79.4, 79.3, 71.4, 71.3, 70.2, 70.1. HR-MS (ESI) (M+H)$^+$ m/z Calcd. for C$_{15}$H$_{14}$NO$_{10}$: 368.0612. Found: 368.0610.

Example 5

Process Improvement for FBC-1

Synthesis of Furan Based Cyclic Biscarbonate with Ester Linkage

Scheme 8. Synthesis of furan based bi-s-cylic-carbonate with ester linkage (FBC-1)

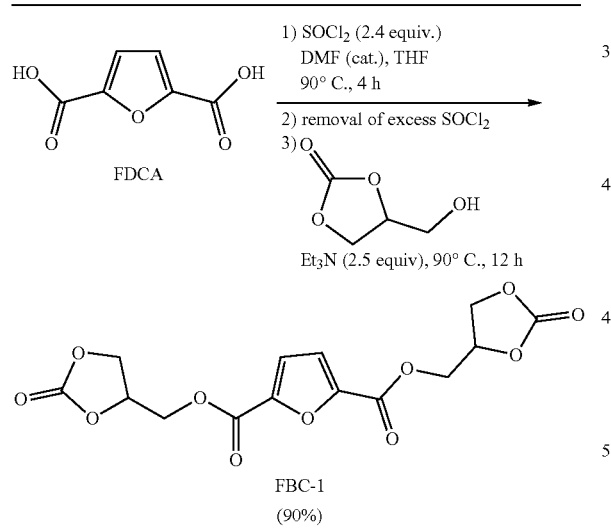

Preparation of FDCA chloride in THF solution: To a round bottom flask connected with condenser, 2,5-furandicarboxylic acid (FDCA) (12.5 g, 80 mmol), thionyl chloride (SOCl$_2$) (14 mL, 192 mmol) and catalytic amount of DMF (0.1 mL) were added and the reaction was carried out at 90° C. under argon for 4 h. Excess of SOCl$_2$ were removed under vacuum. Then the residue solid was redissolved in 40 mL anhydrous THF.

To a solution of trimethylamine (Et$_3$N) (200 mmol, 27.9 mL) and glycerol carbonate (23.6 g, 100 mmol) in 250 ml of anhydrous THF were added slowly to the FDCA chloride in THF solution (40 mL) at 0° C. After stirring at room temperature for 3 h, the reaction was further heated to 90° C. for 18 h. The reaction was quenched by addition of water (100 mL). The product bis((2-oxo-1,3-dioxolan-4-yl)methyl)furan-2,5-dicarboxylate was precipitated out as a white solid. The solid was filtered and washed with water (2*50 mL) and with THF (2*50 mL) to give FBC-1 in 25.8 g (72.4 mmol, 90% yield) which was characterized by $^1$H, $^{13}$C-NMR and HRMS.

$^1$H-NMR (DMSO, 400 MHz): 7.42 (s, 2H), 5.16 (m, 2H), 4.6 (m, 6H), 4.4 (dd, J=8.6, 6.1 Hz, 2H). $^{13}$C NMR (DMSO, 100 MHz): δ=156.7, 154.6, 145.8, 119.6, 74.1, 67.0, 64.5. HRMS (ESI) (M+H)$^+$ m/z Calcd. For C$_{14}$H$_{12}$O$_{11}$: 357.0452. Found: 357.0459.

Example 6

Process Improvement for FBC-2

Optimized Synthesis of Furan Based Cyclic Biscarbonate with Ether Linkage

The scale up and optimized synthesis of cyclic biscarbonate 4,4'-(((furan-2,5-diylbis(methylene))bis(oxy))bis(methylene))bis(1,3-dioxolan-2-one), FBC-2, is shown in Scheme 9. The yield of the first step di-alkylation was increased by changing the phase transfer catalyst from tetrabutylammonium bromide to tetrabutylammonium hydrogen sulfate (TBHS). In addition, the reaction was carried out at room temperature.

Scheme 9. Optimization of synthesis of furan based bis-cyclic-carbonate (FBC-2)

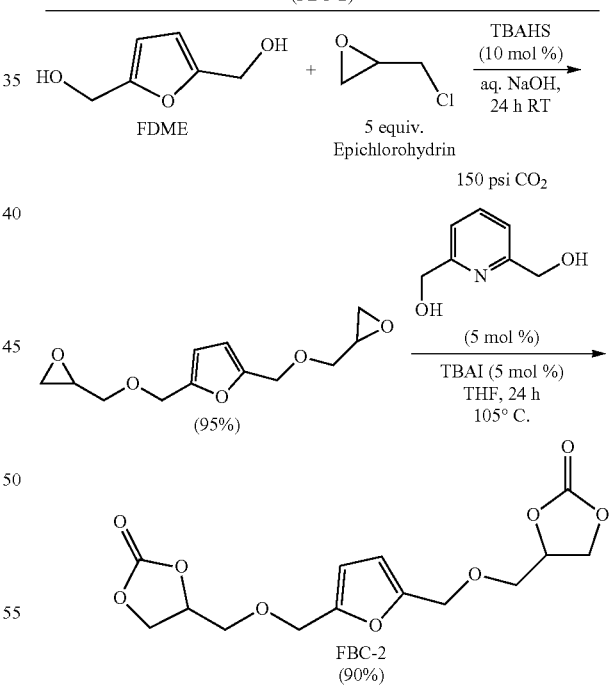

To a solution of sodium hydroxide solution (1:2 w/w) was added with furandimethanol (FDM) (10.2 g, 80 mmol) and 10 mol % of tetrabutylammonium hydrogen sulfate (2.7 g, 8.0 mmol). The reaction mixture was cooled to 0° C., epichlorohydrin (32.5 mL, 400 mmol) was added dropwise over 30 min. The mixture was stirred at room temperature for 16 h. The reaction was quenched by addition of water (50 mL). The aqueous layer was extracted with pentane (10 mL)

to remove excess epichlorohydrin. Then the aqueous layer was extracted with EtOAc (4*30 mL). The combined EtOAc extracts were washed with water (30 mL) and were allowed to pass through a short pad of silica gel. The solvent was evaporated to obtain a pure yellow oil diepoxy product 2,5-bis((oxiran-2-ylmethoxy)methyl)furan in 18.4 g (76 mmol, 95% yield) and characterized by $^1$H and $^{13}$C NMR.

In the second step, the diepoxy product 2,5-bis((oxiran-2-ylmethoxy)methyl)furan (8.6 g, 36 mmol), tetrabutyl ammonium iodide (TBAI) (0.66 g, 1.8 mmol, 5 mol %) and pyridinedimethanol (0.25 g, 1.8 mmol, 5 mol %) were dissolved in 20 mL of anhydrous THF, transferred into a Parr reactor and pressurized with $CO_2$ up to 150 psig after purging with $N_2$ followed by $CO_2$. The reaction was carried out under stirring at 105° C. for 24 h. After the reaction, the reactor was cooled to room temperature and depressurized. The solvent THF was removed and the mixture was redissolved in 200 mL of EtOAc. The organic layer was washed with sodium thiosulfate (3*20 mL) to remove the iodine followed by brine (2*20 mL). The organic layer was separated and dried by sodium sulfate. Then the volume of EtOAc was reduced to 20 mL and a white solid was precipitated out. The solid was filtered, collected and washed with pentane (3*20 mL). The solid was dried in an oven under vacuum at 60° C. for 24 h. The bicarbonate product 4,4'-(((furan-2,5-diylbis(methylene))bis(oxy))-bis(methylene))bis(1,3-dioxolan-2-one) was isolated as a white solid (10.6 g, 32.3 mmol, 90% yield) and characterized by $^1$H NMR.

Example 7

Multigram Scale Synthesis of 2,5-bis((oxiran-2-ylmethoxy)methyl)furan

To a solution of sodium hydroxide in water (30 g in 60 mL), furan-2,5-diyldimethanol (20 g, 156 mmol), and tetrabutylammonium hydrogen sulfate (5.3 g, 1.60 mmol) was added and the mixture was cooled to 0° C. followed by addition of epichlorohydrin (65 mL, 1020 mmol) dropwise over 30 min. The mixture was then stirred at room temperature for 16 h. Deionised water (50 mL) was added and the mixture was extracted with ethyl acetate (3×60 mL). The extracts were passed through a pad of silica gel using ethyl acetate:petroleum ether (1:1) as eluent and concentrated under reduced pressure. Product was obtained as a yellow liquid (31.1 g, 81%).

Example 8

Multigram Scale Synthesis of FBC-2 Under Optimized Conditions 2,5-bis((oxiran-2-ylmethoxy)methyl)furan (50 g, 208 mmol) and tetrabutylammonium bromide (TBABr) (2 g, 6.24 mmol) were dissolved in 135 mL of dry THF and transferred into a Parr reactor. The reactor was purged with $N_2$ followed by $CO_2$ and then pressurized with $CO_2$ up to 18 bar. The reaction was carried out under stirring at 75° C. for 18 h. After the reaction, the reactor was cooled to room temperature and depressurized. THF was removed under reduced pressure and the crude product was then dissolved in ethyl acetate and filtered to afford the pure white product and a dark brown solution. Dark brown filtrate was passed through a pad of silica gel using ethyl acetate: petroleum ether (2:1) as eluent and solvent removed under reduced pressure to afford the remaining product (59 g, 86%).

Example 9

Synthesis of Pyridine Based Cyclic Biscarbonate with Ester Linkage

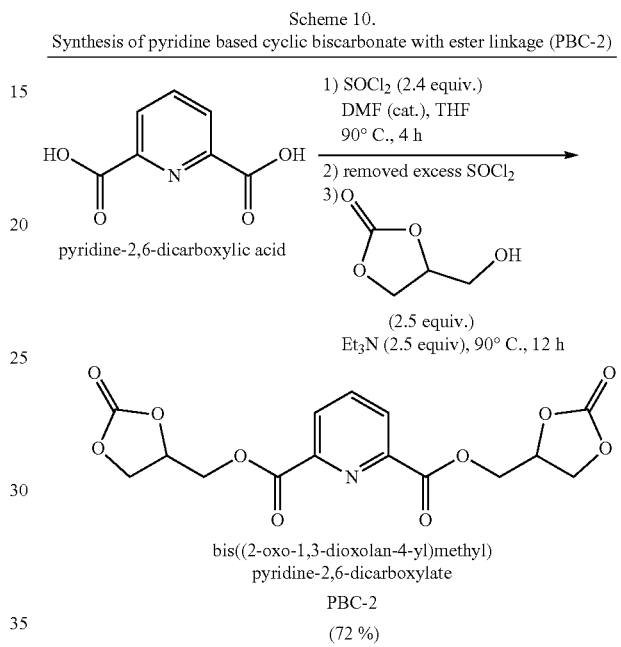

Scheme 10.
Synthesis of pyridine based cyclic biscarbonate with ester linkage (PBC-2)

pyridine-2,6-dicarboxylic acid bis((2-oxo-1,3-dioxolan-4-yl)methyl) pyridine-2,6-dicarboxylate
PBC-2
(72 %)

Preparation of pyridine-2,6-dicarboxylic acid chloride in DMF solution: To a round bottom flask connected with condenser, pyridine-2,6-dicarboxylic acid (3.68 g, 40 mmol), thionyl chloride ($SOCl_2$) (8.7 mL, 120 mmol) and 3 mL of DMF (catalytic amount) were added and the reaction was heated at 80° C. under argon for 3 h. After that a colorless solution was obtained. The solvent together with excess thionyl chloride were removed under vacuum. The remained pyridine-2,6-dicarboxylic acid chloride was redissolved in 10 mL of anhydrous DMF.

To a solution of the reaction mixture of $Et_3N$ (50.3 mL, 360 mmol) and glycerol carbonate (14.2 g, 120 mmol) in 150 mL of THF were added slowly the pyridine-2,6-dicarboxylic acid chloride in DMF solution at 0° C. After stirring at room temperature for 3 h, the reaction was heated at 80° C. for 18 h. The reaction was quenched by addition of water (100 mL). The product bis((2-oxo-1,3-dioxolan-4-yl)methyl)-pyridine-2,6-dicarboxylate was precipitated out from reaction mixture. The solids were collected, filtered and washed with water (2*50 mL) and with THF (2*50 mL) to give 10.6 g (26.3 mmol) of off-white solids (72% yield) which were characterized by $^1$H-NMR, $^{13}$C-NMR and HRMS. $^1$H NMR (400 MHz, DMSO-$d_6$) δ 8.43-8.08 (m, 3H), 5.27-5.10 (m, 2H), 4.77-4.52 (m, 6H), 4.45 (dd, J=8.6, 6.2 Hz, 2H); $^{13}$C NMR (101 MHz, DMSO-$d_6$) δ 163.4, 154.8, 147.4, 139.6, 128.4, 74.3, 66.2, 64.9 HR-MS (ESI$^+$): Calcd. for $C_{15}H_{13}NO_{10}$ [M+Na]$^+$: 390.0432; Found: 390.0450.

Example 10

Synthesis of Novel Hydroxypolyurethanes (PHUs)

Linear hydroxypolyurethane structures were synthesized by polyaddition of the prepared cyclic biscarbonates with various readily available diamines, as shown in Scheme 11.

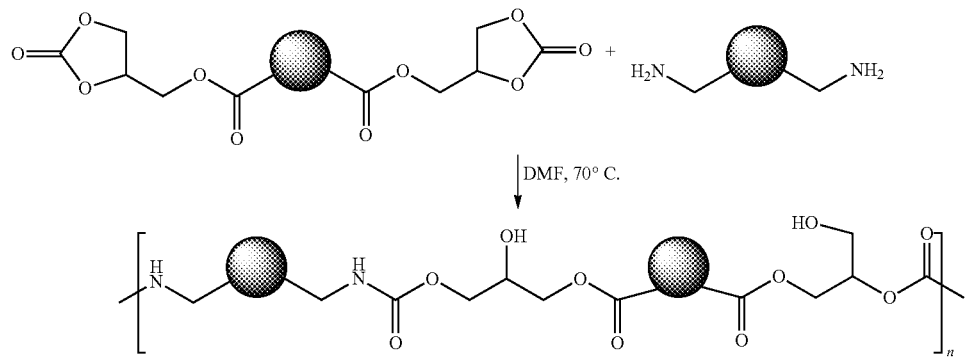

Scheme 11.1. Synthesis Procedure of PHUs using biobased bis-carbonates and comercial bis-amines

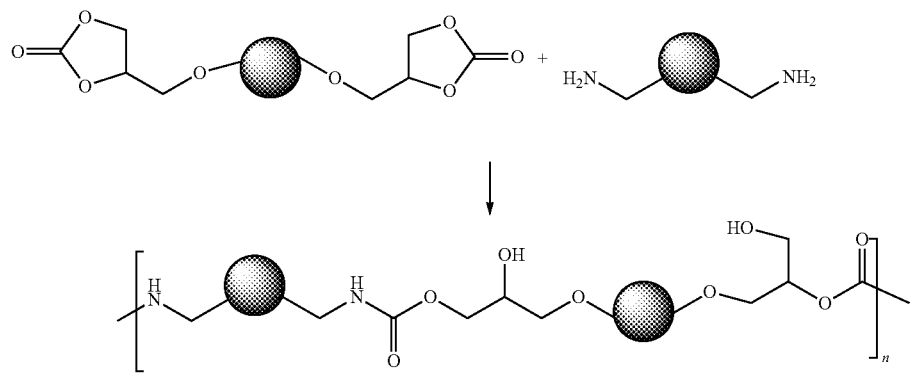

Scheme 11.2. Synthesis Procedure of PHUs using biobased bis-carbonates with ether linkage and commercial bis-amines

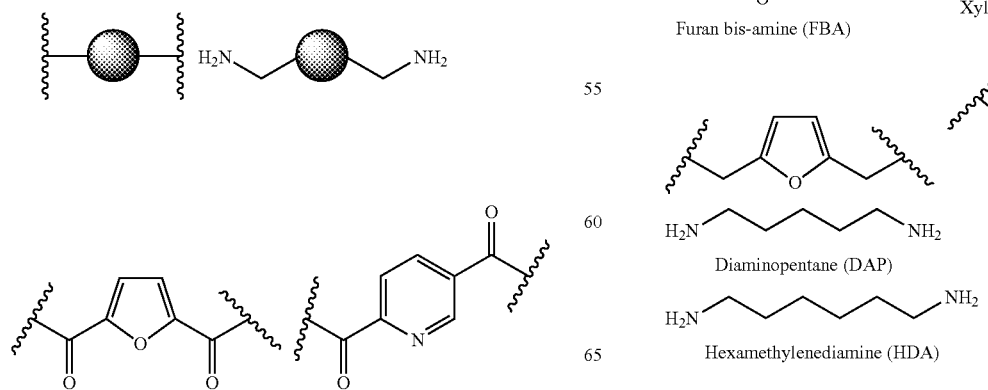

Scheme 11.3. Chemical structure of examples of functional groups present in the bis-carbonates and bis-amines used in Schemes 11.1 and 11.2.

In the synthesis of PHUs of the present application, the cyclic biscarbonate (e.g. 250 mg) and two drops of mesitylene (as internal standard) were taken into a (e.g. 10 ml) glass reactor and the content was dissolved in anhydrous DMF (e.g. 0.5 or 1 ml) while stirring on an oil bath at 70° C. (oil bath temperature). The solution was then purged with nitrogen for 15-20 min. A solution of the diamine (1 mol equiv) was prepared separately in anhydrous DMF, purged with nitrogen and charged into the reaction tube to initiate the reaction.

For polymerizations using less soluble diamines (e.g. XDA), the diamine was first dissolved in dry DMF at 70° C. and then equimolar quantity of cyclic biscarbonate monomer solution (nitrogen purged) was added to it. Reaction mixture was then allowed to stir for 48 h. Time to time samples were collected by syringe to monitor monomer conversion by $^1$H NMR spectroscopy. Finally, the reaction mixture was cooled down to room temperature and the polymer was precipitated using excess diethyl ether. Light brown polymer was then dried under air followed by heating at 80° C. in high vacuum oven. A small amount of polymer was re-dissolved in small amount of dry DMF, re-precipitated using ether and dried before the final characterization by gel permeation chromatography (GPC) using DMF as eluent and NMR spectroscopy.

Polymer Characterization $^1$H NMR spectra were recorded on a 400 MHz Bruker Ultra-Shield AVANCA 400SB spectrometer. Mesitylene or residual solvent peaks were used as internal standard.

Number average molecular weight (Mn), peak molecular weight (Mp) and polydispersity index (PDI) analysis of polymers synthesized according to the method disclosed herein were performed in size exclusion chromatography (SEC) systems using DMF as solvent. The DMF GPC system was equipped with Waters 515 HPLC pump, Waters 717 plus autosampler, Waters 2414 refractive index (RI) detector, two PLgel 5 μm mixed-C columns. The eluent flow rate was 0.8 ml/min and the columns were maintained at 50° C. The injected sample solution concentration was 5 mg/ml and injected volume was 50 μl.

The details of the polymerization conditions and GPC data of the PHUs synthesized according to the method disclosed herein are provided in Table 1 as follows.

TABLE 1

Details of polymerization conditions and GPC data of the PHUs synthesized according to the method disclosed herein.

| PHU code | Monomer Bis-carbonate | Bis-amine | Conversion (%) | GPC (DMF)[b] Mn, g/mol | Mp, g/mol | PDI | Tg, ° C. |
|---|---|---|---|---|---|---|---|
| BP75 | FBC1 | FBA | >98 | 3200 | 3750 | 1.31 | 44 |
| BP76 | FBC1 | DAP | >99 | 3900 | 5400 | 1.37 | 22 |
| BP77 | FBC1 | XDA | >81 | 2700 | 2600 | 1.35 | 51 |
| BP78 | PBC1 | FBA | >99 | 3100 | 3600 | 1.32 | 34 |
| BP79 | PBC1 | DAP | >99 | 3950 | 4900 | 1.41 | 10 |
| BP80 | PBC1 | XDA | 52 | 2450 | 2050 | 1.40 | 67 |
| BP81 | FBC2 | FBA | >95 | 2650 | 3400 | 1.49 | 14 |
| BP82 | FBC2 | DAP | >99 | 3400 | 6300 | 1.85 | — |
| BP83 | FBC2 | XDA | 59 | 2500 | 2900 | 1.74 | 12 |
| BP89 | FBC2 | HMDA | >98 | 8000 | 11600 | 1.45 | −7 |
| BP84 | HFBC | DAP | >99 | 2350 | 2000 | 1.24 | 18 |
| BP85 | HFBC | FBA | >99 | 2412 | 2129 | 1.18 | −18 |
| BP86 | HFBC | XDA | >99 | 2659 | 2381 | 1.23 | 23 |
| BP90 | FBC1 | HMDA | 99 | 4100 | 5250 | 1.49 | 19 |

Figure 1:
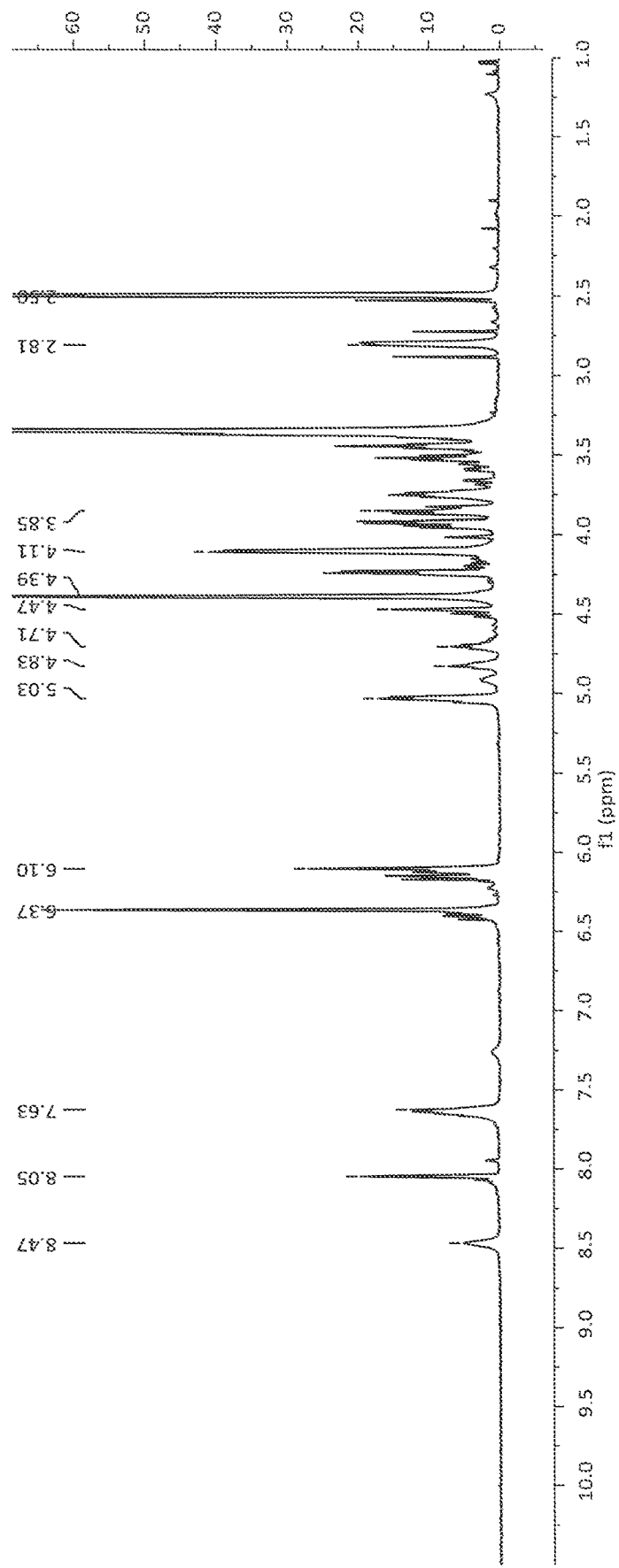
FIG. 1 is $^1$H NMR spectrum (in DMSO-$d_6$) of polyhydroxyurethanes (PHUs) obtained from the polymerisation of FBC-2 and FBA in accordance with various embodiments disclosed herein.
Figure 2:
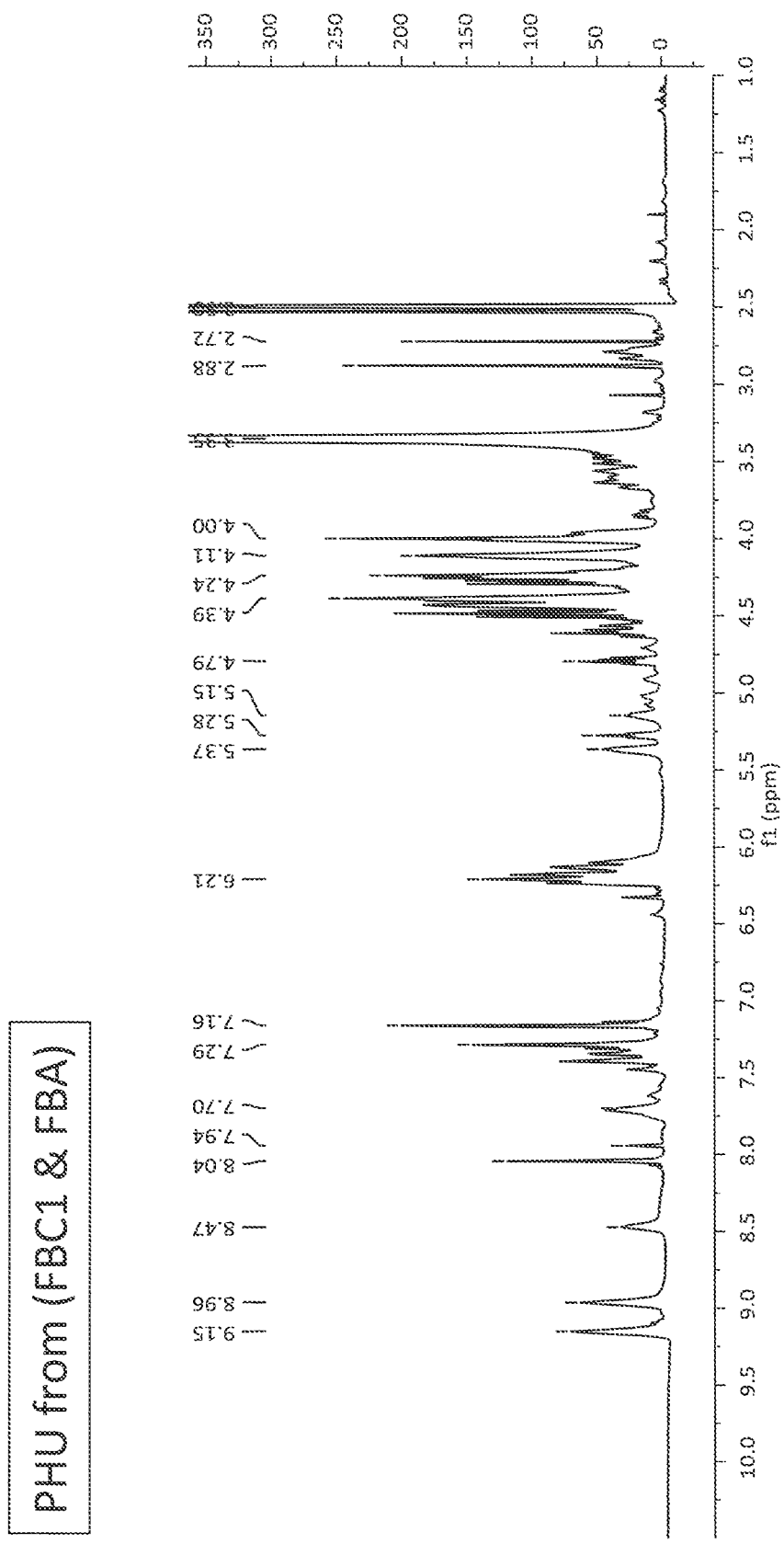
FIG. 2 is $^1$H NMR spectrum (in DMSO-$d_6$) of polyhydroxyurethanes (PHUs) obtained from the polymerisation of FBC-1 and FBA in accordance with various embodiments disclosed herein.
Figure 3:
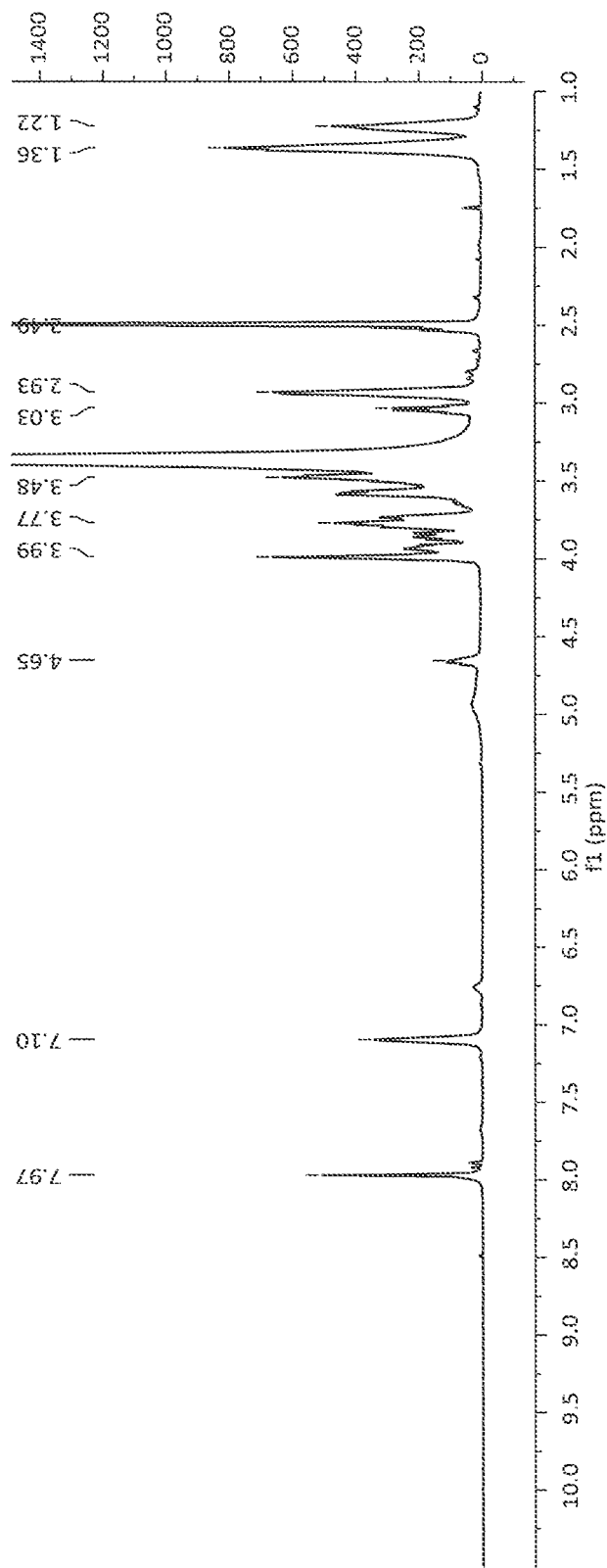
FIG. 3 is $^1$H NMR spectrum (in DMSO-$d_6$) of polyhydroxyurethanes (PHUs) obtained from the polymerisation of HFBC and DAP in accordance with various embodiments disclosed herein.
Figure 4:
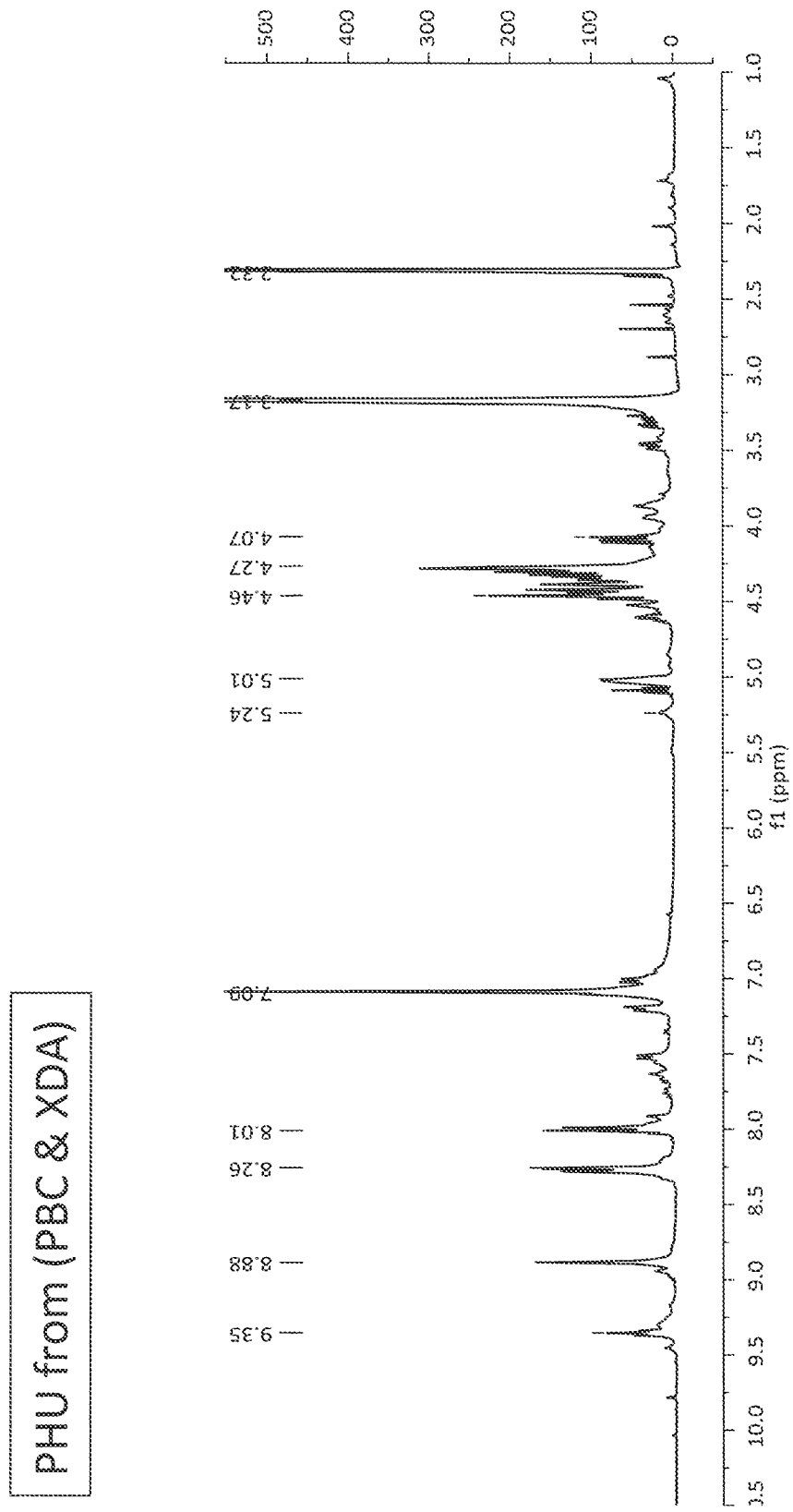
FIG. 4 is $^1$H NMR spectrum (in DMSO-$d_6$) of polyhydroxyurethanes (PHUs) obtained from the polymerisation of PBC and XDA in accordance with various embodiments disclosed herein.

$^1$H NMR spectra (in DMSO-d$_6$) of polyhydroxyurethanes (PHUs) obtained using different bis-carbonate and bis-amine monomers according to the method disclosed herein are provided in FIGS. 1 to 4. FIG. 1 is $^1$H NMR spectrum (in DMSO-d$_6$) of polyhydroxyurethanes (PHUs) obtained using FBC-2 and FBA. FIG. 2 is $^1$H NMR spectrum (in DMSO-d$_6$) of polyhydroxyurethanes (PHUs) obtained using FBC-1 and FBA. FIG. 3 is $^1$H NMR spectrum (in DMSO-d$_6$) of polyhydroxyurethanes (PHUs) obtained using HFBC and DAP. FIG. 4 is $^1$H NMR spectrum (in DMSO-d$_6$) of polyhydroxyurethanes (PHUs) obtained using PBC and XDA.

Figure 5:
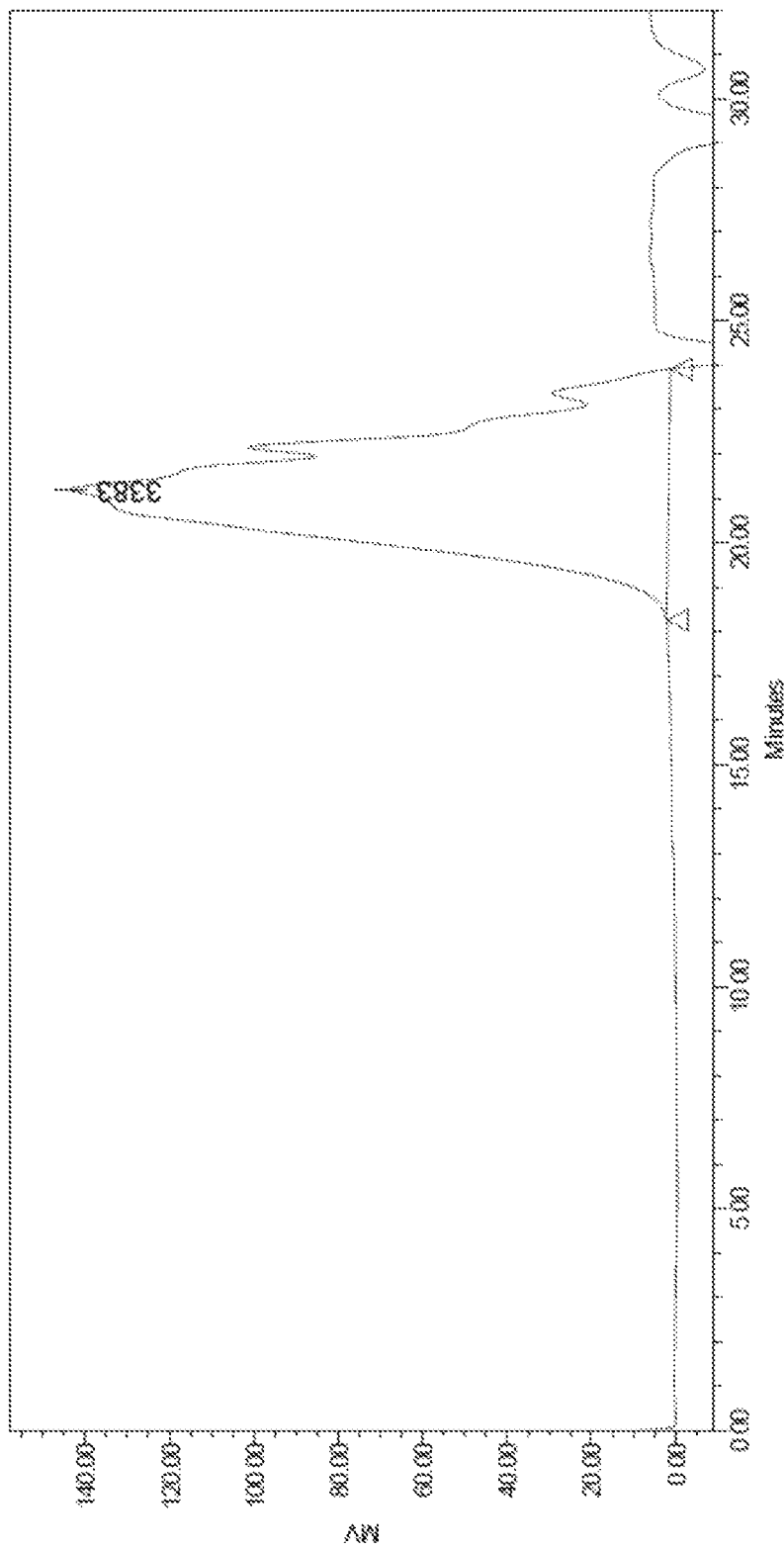
FIG. 5 shows the GPC chromatogram of polyhydroxyurethanes (PHUs) obtained by the polymerization of FBC-2 and FBA in accordance with various embodiments disclosed herein. As shown, the peak molecular weight of the polyhydroxyurethane obtained by the polymerization of FBC-2 and FBA is 3,383 g/mol.

GPC chromatogram of polyhydroxyurethanes (PHUs) obtained by the polymerization of FBC-2 and FBA is provided in FIG. 5.

Example 11

Polymerisation of FBC-2 Obtained from Example 6 with Diamine (DAP/HMDA)

FBC-2 and two drops of mesitylene (as internal standard) were taken into a glass tube and the content was dissolved in anhydrous DMF while stirring on an oil bath at 70° C. (oil bath temperature). The solution was then purged with nitrogen for 15-20 min. A solution of the diamine (1 equiv) was prepared separately in anhydrous DMF, purged with nitrogen and charged into the reaction tube to initiate the reaction. Reaction mixture was then allowed to stir for 24 h. Time to time samples were collected by syringe to monitor monomer conversion by $^1$H NMR spectroscopy. Finally, the reaction mixture was cooled down to room temperature and the polymer was precipitated using excess diethyl ether. Light brown polymer obtained was then dried under air followed by heating at between 60 to 70° C. in high vacuum oven. A small amount of polymer was re-dissolved in small amount of dry DMF, re-precipitated using ether and dried before the final characterization by GPC (DMF eluent) and NMR spectroscopy.

The details of the polymerization conditions and GPC data for FBC-2 based PHUs are provided in Table 2 as follows.

TABLE 2

Details of polymerization conditions and GPC data for FBC-2 based PHUs

| Polymer Code | Solvent (mL) | FBC-2 (mg) | Bis-Amine (mg) | Conversion (%) | GPC Mn, g/mol | Mp, g/mol | PDI |
|---|---|---|---|---|---|---|---|
| BP122 | DMF (3) | 2000 | DAP (616.8) | >99 | 14800 | 23300 | 1.7 |
| BP129 | DMF (0.75) | 500 | DAP (154.2) | >99 | 14400 | 22500 | 1.8 |

TABLE 2-continued

Details of polymerization conditions and GPC data for FBC-2 based PHUs

| Polymer Code | Solvent (mL) | FBC-2 (mg) | Bis-Amine (mg) | Conversion (%) | GPC Mn, g/mol | Mp, g/mol | PDI |
|---|---|---|---|---|---|---|---|
| BP136 | DMF:MeOH (3:1) (0.5) | 300 | DAP (92.5) | >99 | 16340 | 27160 | 1.8 |
| BP138 | DMF (1) | 300 | HMDA (106.2) | 85 | 10020 | 15830 | 1.7 |

Example 12

Gram Scale Polymerisation of FBC-2 with DAP

Figure 6:
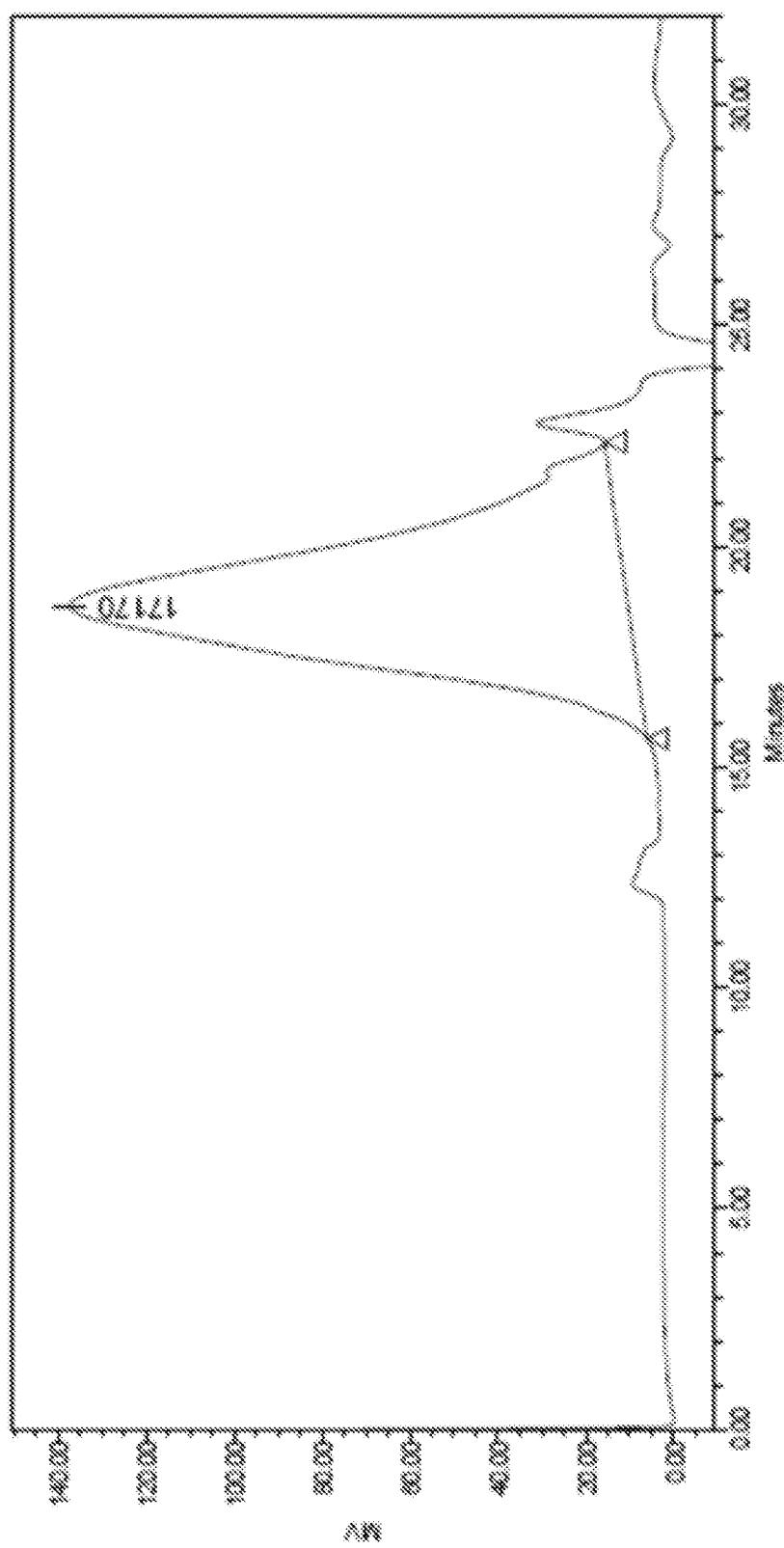
FIG. 6 shows the GPC chromatogram of polyhydroxyurethanes (PHUs) obtained by the polymerization of FBC-2 and DAP in accordance with various embodiments disclosed herein. As shown, the peak molecular weight of the polyhydroxyurethane obtained by the polymerization of FBC-2 and DAP is 17,170 g/mol.

FBC-2 and two drops of mesitylene (as internal standard) were taken into a glass tube and the content was dissolved in anhydrous DMF while stirring on an oil bath at 70° C. (oil bath temperature). The solution was then purged with nitrogen for 15-20 min. A solution of the diamine (1 mol equiv) was prepared separately in anhydrous DMF, purged with nitrogen and charged into the reaction tube to initiate the reaction. Reaction mixture was then allowed to stir for 28 h. Time to time samples were collected by syringe to monitor monomer conversion by $^1$H NMR spectroscopy. Finally, the reaction mixture was cooled down to room temperature and the polymer was precipitated using excess diethyl ether. Light brown polymer obtained was then dried under air followed by heating at 70° C. in high vacuum oven. A small amount of polymer was re-dissolved in small amount of dry DMF, re-precipitated using ether and dried before the final characterization by GPC (DMF eluent), DSC (Tg=14-20° C.) and NMR spectroscopy. The details of the polymerization conditions and GPC data for the gram scale synthesis of FBC-2 based PHU are provided in Table 3 as follows. The GPC chromatogram of PHU obtained by the polymerization of FBC2 and DAP is provided in FIG. 6.

TABLE 3

Details of polymerization conditions and GPC data for the gram scale synthesis of FBC-2 based PHU

| Polymer Code | Solvent (mL) | FBC-2 (g) | Bis-Amine DAP (g) | Conversion (%) | GPC Mn, g/mol | Mp, g/mol | PDI |
|---|---|---|---|---|---|---|---|
| BP142 | DMF (15) | 9.85 | 3.07 | >99 | 11130 | 17380 | 1.8 |
| BP147 | DMF (30) | 19.8 | 6.15 | >99 | 11190 | 17170 | 1.9 |

Example 13

Polymerization of FBC-2 with DAP at 60 g Scale

FBC-2 (60 g, 183 mmol) was dissolved in 70 mL of dry DMF in a 500 mL two neck flask. The flask was purged with argon gas and heated to 70° C. Mesitylene was added as an internal reference and a small sample of mixture was taken to be analysed by $^1$H NMR and labelled as 0 h. Pentane-1,5-diamine [DAP] (18.7 g, 183 mmol) was dissolved in 20 mL of DMF and added into round bottom flask. The reaction was stirred for 28-52 h with sample being taken at 1 h, 3 h, 6 h, 24 h, 28 h for NMR analysis. Reaction mixture was added drop by drop into glass bottle containing diethyl ether (200 mL) with stirring. Product was washed further with diethyl ether (2×200 mL) before drying overnight in a vacuum oven at 60° C. (75 g, 95%). GPC: Mn 12731 g/mol, Mp 19103 g/mol, PDI 1.8.

Example 14

Polymerisation of PBC-2 Obtained from Example 9 with Diamine (FBA/DAP)

PBC-2 and two drops of mesitylene (as internal standard) were taken into a glass tube and the content was dissolved in anhydrous DMF while stirring on an oil bath at 70° C. (oil bath temperature). The solution was then purged with nitrogen for 15-20 min. A solution of the diamine (1 equiv) was prepared separately in anhydrous DMF, purged with nitrogen and charged into the reaction tube to initiate the reaction. Reaction mixture was then allowed to stir for 48 h. Time to time samples were collected by syringe to monitor monomer conversion by $^1$H NMR spectroscopy. Finally, the reaction mixture was cooled down to room temperature and the polymer was precipitated using excess diethyl ether. Light brown polymer was then dried under air followed by heating at 70° C. in high vacuum oven. A small amount of polymer was re-dissolved in small amount of dry DMF, re-precipitated using ether and dried before the final characterization by GPC (DMF eluent) and NMR spectroscopy.

The details of the polymerization conditions and GPC data for PBC-2 based PHU are provided in Table 4 as follows.

TABLE 4

Details of polymerization conditions and GPC data for PBC-2 based PHUs

| Polymer Code | Solvent (mL) | PBC-2 (mg) | Bis-Amine (mg) | Conversion (%) | GPC Mn, g/mol | GPC Mp, g/mol | PDI |
|---|---|---|---|---|---|---|---|
| BP125 | DMF (3.5) | 500 | FBA (174) | >99 | 2740 | 3170 | 1.3 |
| BP126 | DMF (3) | 500 | DAP (141) | >99 | 4230 | 4810 | 1.3 |

Post-Functionalization of Polyhydroxyurethanes

The novel PHUs obtained can be further functionalized through the hydroxyl group to achieve new functionalized PHUs having desired properties such as hydrophilicity, hydrophobicity, oil solubility and dispersibility in water and oil for various applications. The functionalization could lead to neutral, anionic, cationic or zwitterionic polymers. This strategy could also be applied to any polyhydroxyurethanes obtained through the reaction between any bis/multi-carbonate and any bis/multi-amine and the corresponding obtained PHU having one or more unfunctionalised primary or secondary hydroxyl groups. The functionalization strategy includes, but is not limited to esterification, sulphonylation, phosphorylation, zwitterion formation, grafting suitable molecular entities/oligomers/polymers, etc. The following examples illustrate the said component of the invention.

Anionic Isocyanate Free Polyurethanes

The hydroxyl groups of the PHUs were functionalized introducing anionic phosphate ester or alkylsulfonate groups as pendants. The counter cations can be varied and the degree of functionalization optimized to modify solubility, dispersion and crosslinking characteristics of the PHUs in water at different pHs as well as in various organic solvents.

Example 15

Synthesis of PHU-Organophosphate Monoester

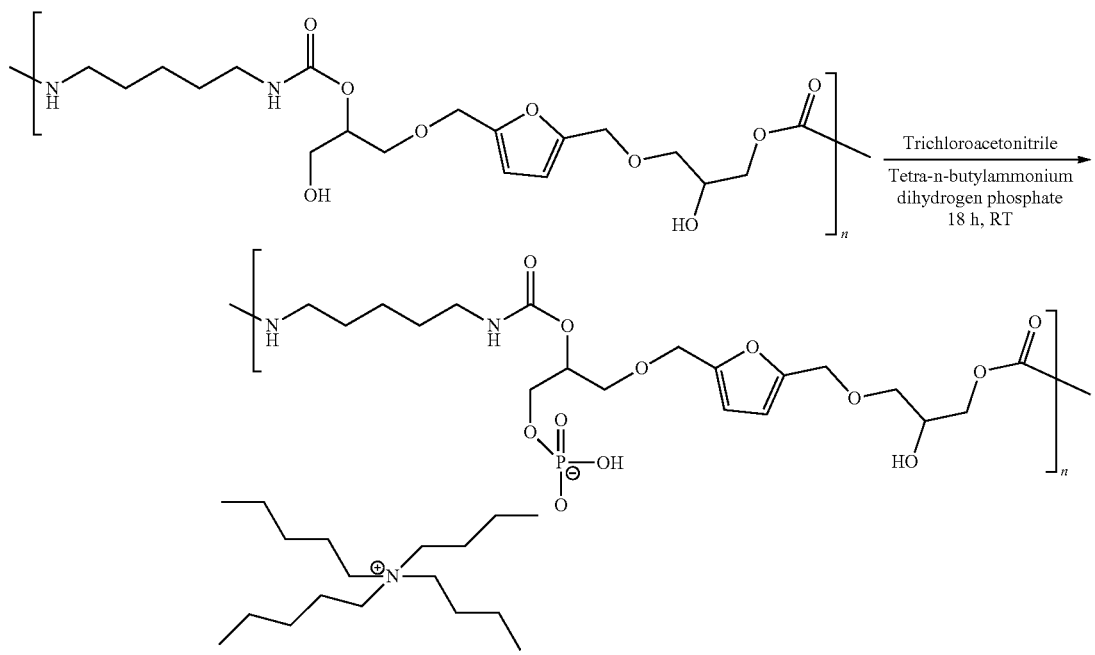

Scheme 12. Procedure for the synthesis of PHU-organophoasphate monoester

To a solution of a representative PHU (1.00 g) in anhydrous DMF (5 mL) and acetonitrile (1 mL) mixture was added with the desired amount of trichloroacetonitrile (TCAN, 1.1 equiv. to TBAP). Desired amount of tetra-n-butylammonium dihydrogen phosphate (TBAP) was dissolved separately in anhydrous acetonitrile (1 mL) and added into the polymer solution dropwise. The reaction mixture was stirred at room temperature for 18 h. Solvent was removed under reduced pressure and the residue was re-dissolved in a small amount of acetonitrile (1 mL). The phosphate-functionalized PHU was precipitated out using diethyl ether (10 mL) as anti-solvent. Characterization was done using $^1$H and $^{31}$P NMR (DMSO-$d_6$), TGA, DSC and DLS (Table 5). $^1$H NMR showed n-butyl peaks at 1.57, 1.32 and 0.93 ppm. Multiple peaks between 2.00-10.00 ppm were observed in $^{31}$P NMR. Preliminary solubility data are demonstrated in Table 6.

TABLE 5

Synthesis of PHU-organophosphate monoester and their characterization studies

| Polymer | TBAP (mg) | % of hydroxyl groups phosphorylated[a] | Yield (%) | TGA at 5% loss under $N_2$ (° C.) | DSC Tg, (° C.) | DLS Particle size (nm) | DLS Zeta potential (mV) |
|---|---|---|---|---|---|---|---|
| FBC2 + DAH | 143 | 5 | >99 | 219 | 28 | n.d | n.d |
|  | 340 | 15 | >99 | 180 | 25 | 218 | −55 |
|  | 1710 | 50 | 56 | 172 | 36 | n.d | n.d |

[a](determined from $^1$H NMR using furanyl proton as reference)

TABLE 6

Solubility of representative PHU-organophosphate monoesters

| Polymer | % of hydroxyl groups phosphorylated[a] | Solubility | | | | | | |
|---|---|---|---|---|---|---|---|---|
| | | pH 4 | pH 7 | pH 9 | DMF | MeOH | THF | Acetone |
| FBC2 + DAP | 5 | ☒ | ☒ | ☒ | ☑ | Dispersed | ☒ | ☒ |
|  | 15 | Dispersed | Dispersed | Dispersed | ☑ | Dispersed | ☒ | ☒ |
|  | 50 | ☑ | ☑ | ☑ | ☑ | ☑ | ☒ | ☒ |

[a](determined from $^1$H NMR using furanyl proton as reference)

Example 16

Functionalization of PHUs with Alkyl Sulfonate

Scheme 13. Procedure for functionalization of PHUs with alkyl sulfonate

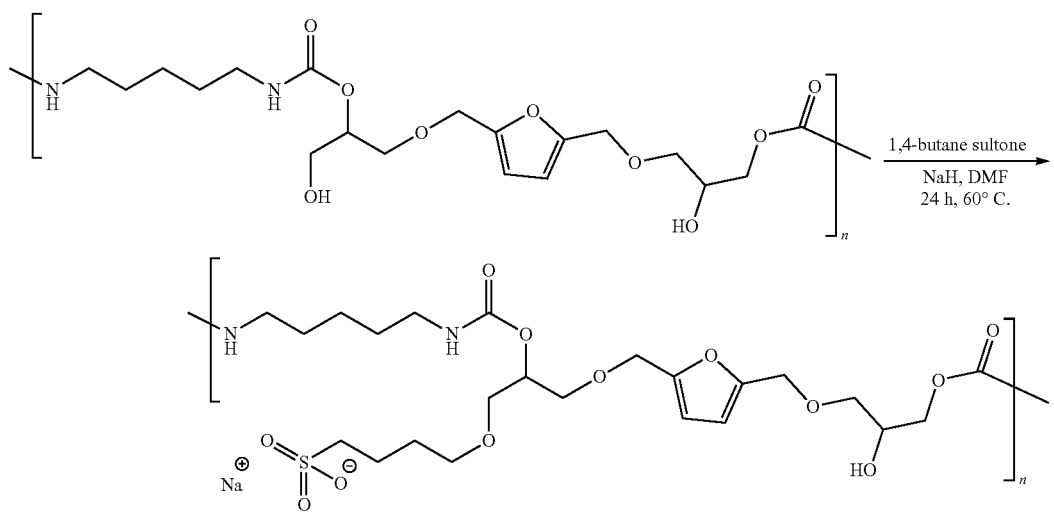

To a solution of a representative PHU (1.00 g) (Table 7) in anhydrous DMF (5 mL) was added with 1,4-butane sultone (1.1 equiv). 60% sodium hydride in oil (1.1 equiv) was then slowly added to the reaction mixture at room temperature and was stirred at room temperature for about 30 min before heating up to 60° C. and stirred for another 24 h. The reaction mixture was cooled to 0° C. and 20 mL methanol was added to quench the reaction. After the solvent was removed under reduced pressure and the solid was washed with diethyl ether (3×10 mL) characterization/preliminary solubility studies were done using $^1$H NMR in DMSO-$d_6$ with butyl peaks observed at 1.73 and 1.73 ppm (Tables 7 and 8).

TABLE 7

Details on the functionalization of PHU with 1,4-butane sultone

| Polymer | 60% NaH (mg) | 1,4-butane sultone (μL) | % of hydroxyl groups sulfonated[a] | Yield (%) |
|---|---|---|---|---|
| FBC2 + DAP | 36 | 92 | 6 | >99 |
| | 132 | 338 | 42 | >99 |

[a](determined from $^1$H NMR using furanyl proton as reference)

TABLE 8

Solubility of representative PHUs with pendant n-butyl sulfate groups

| Polymer | % of hydroxyl groups sulfonated[a] | Solubility | | | | | | |
|---|---|---|---|---|---|---|---|---|
| | | pH 4 | pH 7 | pH 9 | DMF | MeOH | THF | Acetone |
| FBC2 + DAP | 6 | Dispersed | Dispersed | Dispersed | ☑ | Dispersed | ☒ | ☒ |
| | 42 | ☑ | ☑ | ☑ | ☑ | Dispersed | ☒ | ☒ |

[a](determined from $^1$H NMR using furanyl proton as reference)

Example 17

Representative Procedure for the Synthesis of Phosphocholine Functionalized PHUs To a representative PHU based on FBC-2 and DAP (0.215 g, 0.50 mmol) in anhydrous DMF (5 mL) solution, triethylamine (0.080 g, 0.80 mmol) was added followed by ethylene chlorophosphate (0.072 g, 0.50 mmol) at room temperature. After stirring the reaction at RT for 18 h, the solvent was removed and the product precipitated using water. The precipitate obtained was washed with water (3×10 mL) and with diethyl ether. Based on the $^1$H NMR, the hydroxyl groups in the PHU were completely reacted. In $^{31}$P NMR a single phosphorous peak was observed at 15.8 ppm. Phosphocholine functionalized PHUs can be obtained by the reaction of this product with trimethylamine.

Post Functionalization of PHUs Using Amino Acids to Form Novel Types of Amino and Thiol Functionalized PHUs PHUs can be functionalized with amino acids or peptides or proteins by any standard esterification protocols introducing amino and thiol pendant groups. The degree of functionalization can be tuned. The thiol groups can facilitate reversible self-crosslinking or cross linking with other substrates such as peptides by disulfide chemistry.

Scheme 14. Post functionalization of PHUs using amino acids

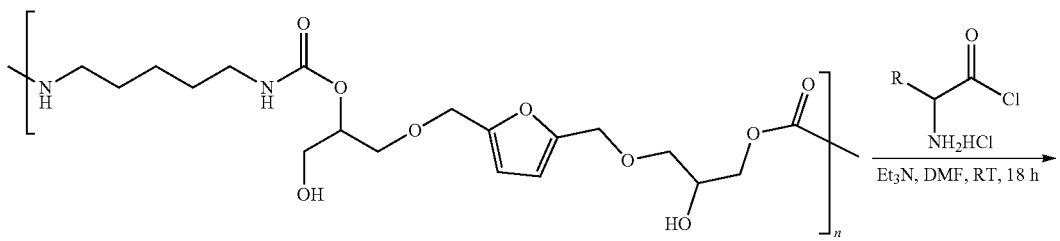

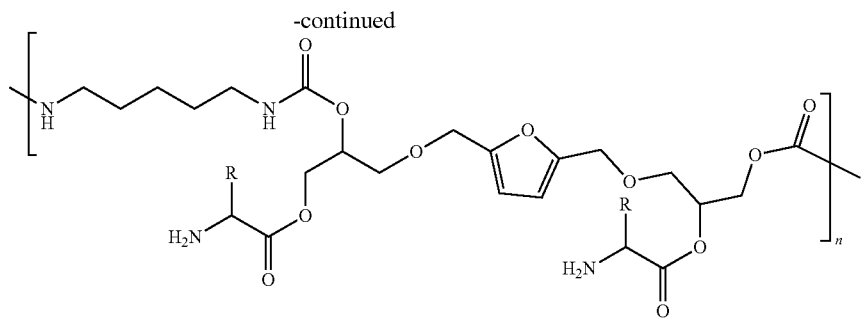

Example 18

Procedure for Esterification of PHUs with Amino Acid Chloride Hydrochloride A representative PHU based on FBC-2 and DAP (0.1 g, 0.23 mmol) in anhydrous DMF (5 mL) solution was added to the desired amino acid chloride hydrochloride (0.5 mmol) in DMF followed by (0.21 mL, 1.50 mmol) triethylamine at room temperature. After 18 h of stirring, the reaction was stopped and subjected to different methods of work-up.

Method A: 10 mL of water was added to quench the reaction. After removing the solvent, the residue obtained was dissolved in water (5 mL). The aqueous layer was washed with ethyl acetate (3×10 mL) and evaporated to dryness under reduced pressure and then re-dissolved in small amount of acetone (1 mL). The functionalized PHU was precipitated out using diethyl ether (10 mL) as anti-solvent.

Method B: 10 mL of water was added at ambient temperature to quench the reaction. After removing the solvent, the residue obtained was dissolved in DCM (5 mL) and was washed with dilute bicarbonate solution (10 mL) followed by water (10 mL). The organic layer was separated and dried with sodium sulfate, filtered and evaporated to dryness under reduced pressure. The residue was re-dissolved in DCM (1 mL). The functionalized PHU was precipitated out using diethyl ether (5 mL) as anti-solvent.

Method C: 10 mL of water was added at ambient temperature to quench the reaction. The polymer precipitated out from the reaction was collected by filtration. The polymer was redissolved in DMF (1 mL) and chloroform was used as anti-solvent to re-precipitate the polymer which was then dried under vacuum (1.18 g (yield 88%)) as a brown syrup. Characterization was done using $^1$H NMR.

TABLE 9

$^1$H NMR characterization of PHUs functionalized with amino acids

| Amino acid | Method for work-up | $^1$H NMR characterization |
| --- | --- | --- |
| glycine | A | glycine peak: 3.44 ppm in CD$_3$OD |
| D-phenylalanine | B | aromatic ring of D-phenylalanine peak: 7.25 ppm in CDCl$_3$ |
| N-acetyl Cysteine | C | N-acetyl peak observed as a singlet at 1.98 ppm in DMSO-d$_6$ |

Hydrophobic Isocyanate Free Polyurethanes

The introduction of pendant medium and long chain alkyl or alkenyl or arylalkyl or arylalkenyl functionalities to PHUs by esterification using fatty acid/or carboxylic acid derivatives by standard esterification protocols resulting in hydrophobic isocyanate free polyurethanes which are oil soluble/dispersible and air/photo/thermo crosslinkable and photoreversibly crosslinkable is reported herein.

Example 19

Synthesis of Fatty Acid Esters of PHUs

A representative PHU based on FBC-2 and DAP (1.00 g, 2.3 mmol) in anhydrous DMF (25 mL) solution was added to the desired acylation reagent (5.0 mmol) followed by (1.05 mL, 7.5 mmol) triethylamine at room temperature. After 24 h of stirring, 10 mL of water was added to quench the reaction. After removing the solvent, the residue obtained was dissolved in DCM (30 mL). The organic layer was washed with dilute bicarbonate solution (20 mL) followed by water (20 mL). The organic layer was separated and dried over sodium sulfate, filtered and evaporated to obtain the expected product.

Scheme 15. Procedure for the synthesis of fatty acid esters of PHUs

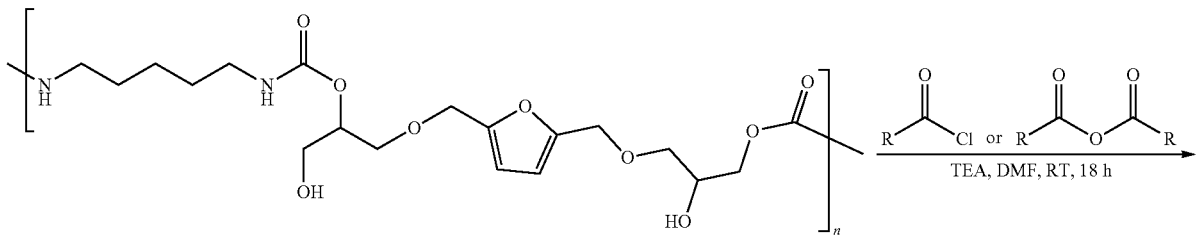

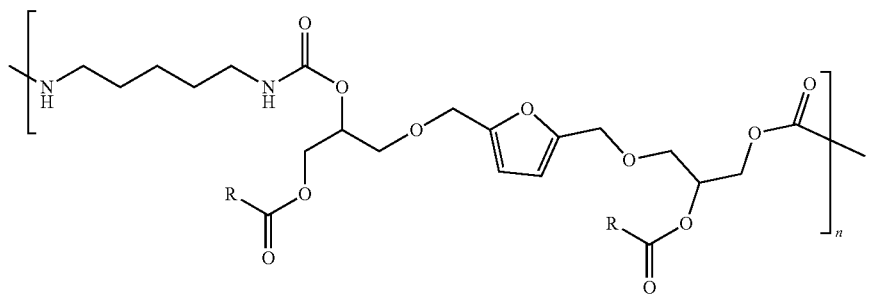

TABLE 10

¹H NMR characterization of PHUs functionalized with acylation reagent

| Entry | Pendant group | Yield (%) | Mn, g/mol | PDI | ¹H NMR characterization in CDCl₃ |
|---|---|---|---|---|---|
| 1 | Butyric acid anhydride | 96 | 6440 | 2.1 | Butyl peak: 2.25, 1.61, 0.91 ppm |
| 2 | Palmitic acid chloride | 95 | 4630 | 2.3 | Palmityl peak: 2.28, 1.58, 1.41, 1.25, 0.87 ppm |
| 3 | Cinnamic acid chloride | 97 | 5920 | 2.2 | Cinnamate alkene peak: 6.41 ppm |
| 4 | Oleic acid chloride | 93 | 10070 | 1.8 | Oleyl alkene peak: 5.32 ppm |
| 5 | Linoleic acid chloride | 94 | 12070 | 2.9 | Linoleyl alkene peak: 5.35 ppm |

Example 20

Modification of PHUs with Lactide

Scheme 16. Procedure for the modification of PHUs with lactide

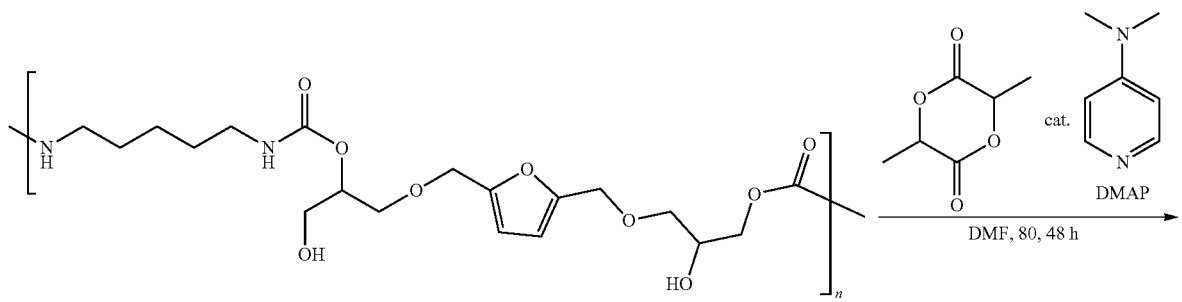

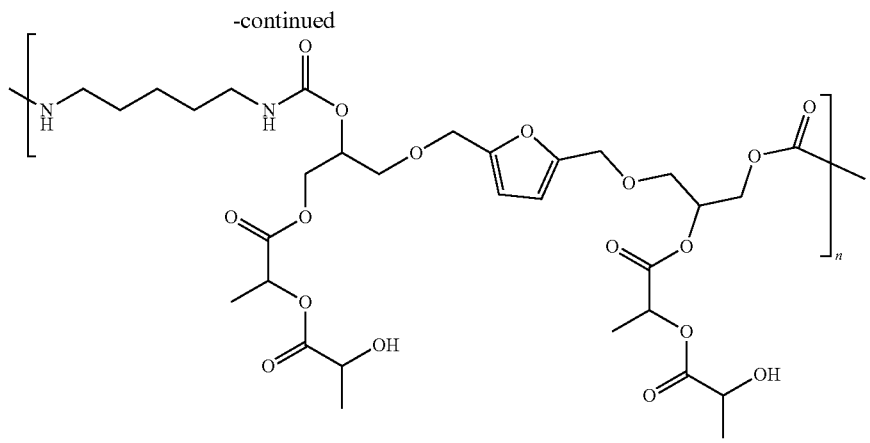

To a representative PHU based on FBC-2 and DAP (1.00 g, 2.5 mmol) in anhydrous DMF (10 mL) solution, lactide (1.08 g, 7.5 mmol) and DMAP (15 mg, 0.1 mmol) were added at room temperature. After 48 h of stirring at 80° C., the solvent was removed and the residue was subsequently dissolved in DCM (5 mL) and precipitated out using diethyl ether as the anti-solvent (10 mL). The product is subsequently washed two times with diethyl ether and dried to obtain the product (1.0 g, 58%). Characterization was done using $^1$H NMR in MeOH-d4 (Lactyl peaks observed at 5.16, 4.22 and 1.2 ppm) and GPC (Mn=8890 g/mol, Mp=10950 g/mol, PDI=1.6.)

PHU Graft Polymers

Different types of polymers can be grafted from or to PHUs resulting in novel functional materials. In one of these approaches exemplified herein, polymers were grafted from PHUs by ring opening polymerization using lactide and lactone to form PHU-graft co-polymers. Other types of ROP using lactams, cyclic carbonates are also possible. An example for the "graft to" approach can be demonstrated using grafting PDMS to PHUs resulting in new functional PHUs, which can be used in anti-smudge coatings. An example on using furan based PHUs for grafting via Diel's-Alder reaction (DA reaction) is also demonstrated. Similarly, peptides or proteins can also be grafted to PHUs resulting in stimuli responsive active delivery, functional coatings materials for biomedical devices etc. For example, DA reaction of maleimide functionalized peptides or proteins to furan based PHUs or coupling of cysteine modified PHU with peptides containing cysteine residue by disulfide chemistry.

Example 21

Ring Opening Polymerization (ROP) of Lactide from PHUs to Form PHU-q-PLA

Scheme 17. Procedure for the ROP of lactide from PHUs to form PHU-g-PLA

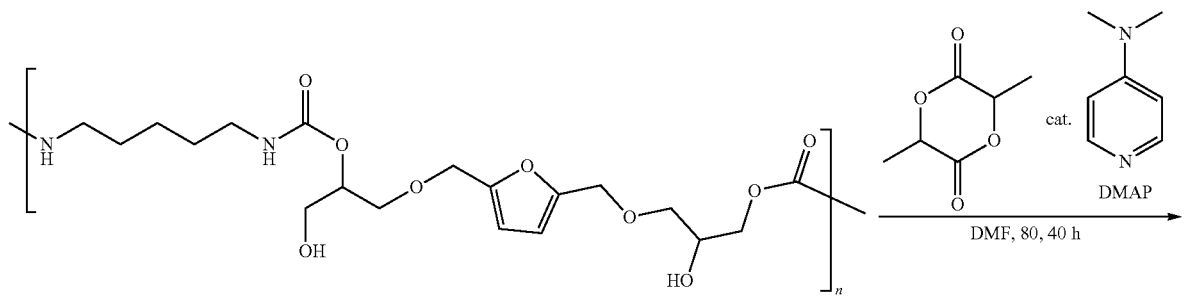

-continued

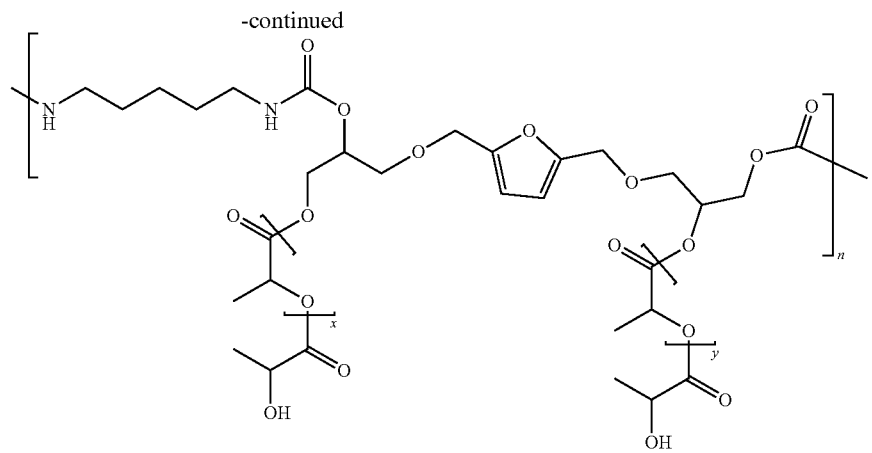

To a representative PHU based on FBC-2 and DAP (1.00 g, 2.5 mmol) in anhydrous DMF (10 mL) solution, lactide (9.08 g, 63 mmol) and DMAP (26 mg, 0.5 mmol) were added at room temperature. After 48 h of stirring at 80° C., the solvent was removed and the residue was subsequently dissolved in DCM (5 mL) and precipitated out using diethyl ether as the anti-solvent (10 mL). The product is washed two times with diethyl ether and dried to obtain the product (3.3 g, 90%). Characterization was done using $^1$H NMR in CDCl$_3$ with lactyl peaks observed at 5.16, 4.10, 1.56 & 1.48 ppm and GPC: Mn=28940 g/mol, Mp=36770 g/mol, PDI=1.4.

Example 22

Grafting Caprolactone from PHUs to Form PHU-c-PCL

Scheme 18. Procedure for grafting caprolactone from PHUs to form PHU-g-PCL

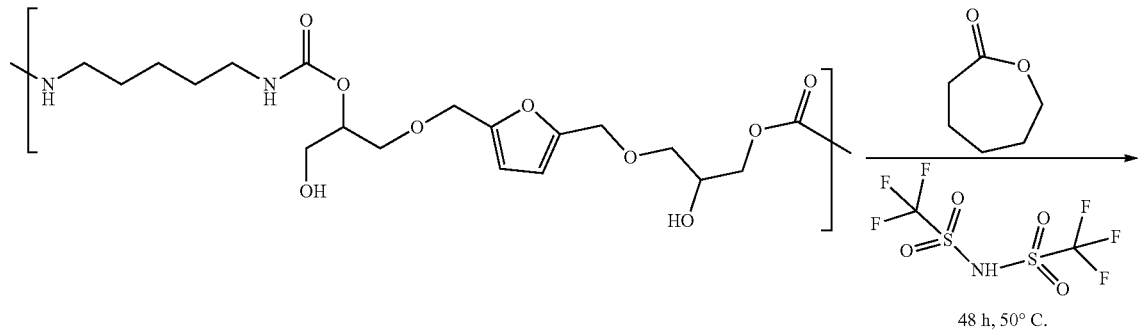

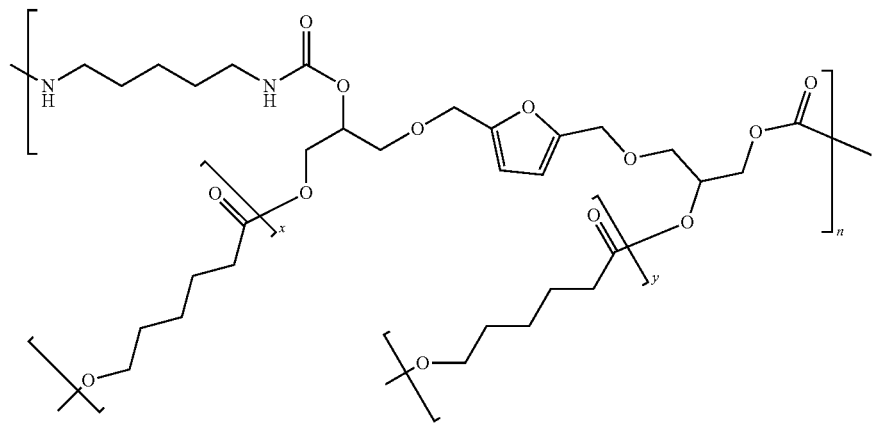

To a solution of a representative PHU based on FBC-2 and DAP (2.00 g) in anhydrous DMF (10 mL) s-caprolactone (16 g, 30 equiv) and trifluromethanesulfonimide (132 mg, 0.1 equiv) were added and the reaction mixture was stirred at 50° C. for 48 h. Solvent was removed under reduced pressure and the product re-dissolved in small amount of chloroform (2 mL). Product was precipitated out using diethyl ether (10 mL) as anti-solvent. Characterization was done using $^1$H NMR in CDCl$_3$ with caproyl peaks observed at 4.05, 2.03, and 1.6

Example 23

Grafting PDMS to PHUs to Form PHU-q-PDMS

Scheme 19. Procedure for grafting PDMS to PHUs to form PHU-g-PDMS

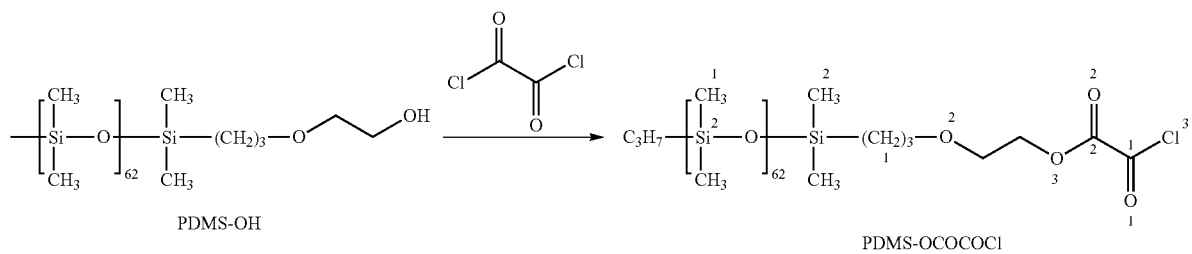

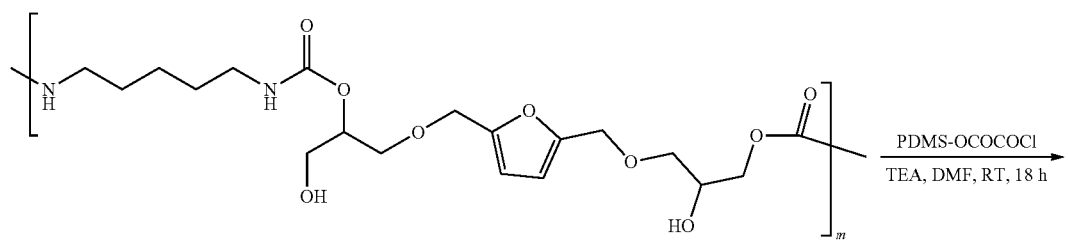

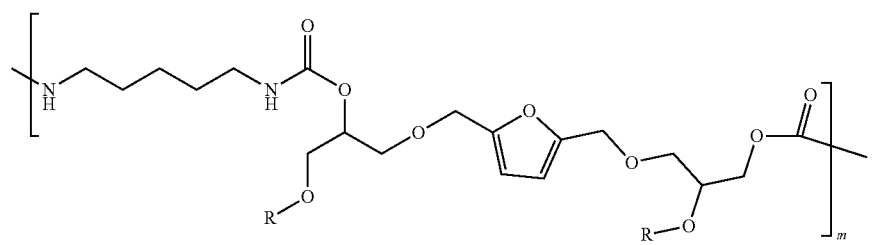

R = H or —COCO$_2$PDMS

To a 50 mL reaction flask filled with Argon was added oxalyl chloride (COCl)$_2$ (1.0 mL, 11.6 mmol). Subsequently, hydroxyl-terminated polydimethylsiloxane (Mn~4670) PDMS-OH (1.1 mL, 0.228 mmol) was added dropwise into the oxalyl chloride. The reaction mixture was allowed to stir at room temperature for 12 h. Unreacted oxalylchloride and volatile impurities were removed by keeping the reaction mixture under vacuum at room temperature for 1 h and at 45° C. for 4 h to yield PDMS-OCOCOCl as a clear liquid.

In the next step, a representative PHU polymer based on FBC-2 and DAP (107.5 mg) was dissolved in anhydrous DMF (5.0 mL) followed by addition of 2 mL THF solution of PDMS-OCOCOCl. The reaction mixture was stirred at room temperature for 48 h and quenched with 1 mL of water. The solvent was removed under vacuum and the residue redissolved in 20 mL of chloroform and was washed with bicarbonate solution (10 mL) followed by water (10 mL). After concentrating this solution to 5 mL, the petroleum ether was added to precipitate out 310 mg (58% yield) of the product as a yellow syrup. Characterization was done using $^1$H NMR in CDCl$_3$ with siloxane peak observed as large board singlets at 0.03 ppm and the furan peak was observed as a singlet at 6.26 ppm.

Example 24

Representative Procedure for Grafting PLA to PHU Via Diel's Alder (DA) Reaction

Scheme 20. Procedure for grafting PLA to PHU via Diel's Alder (DA) reaction

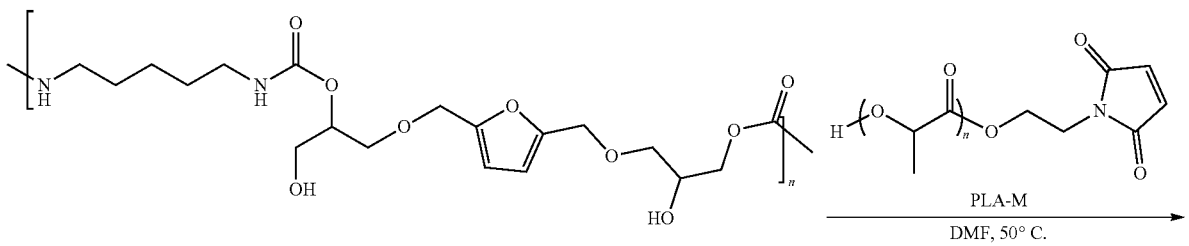

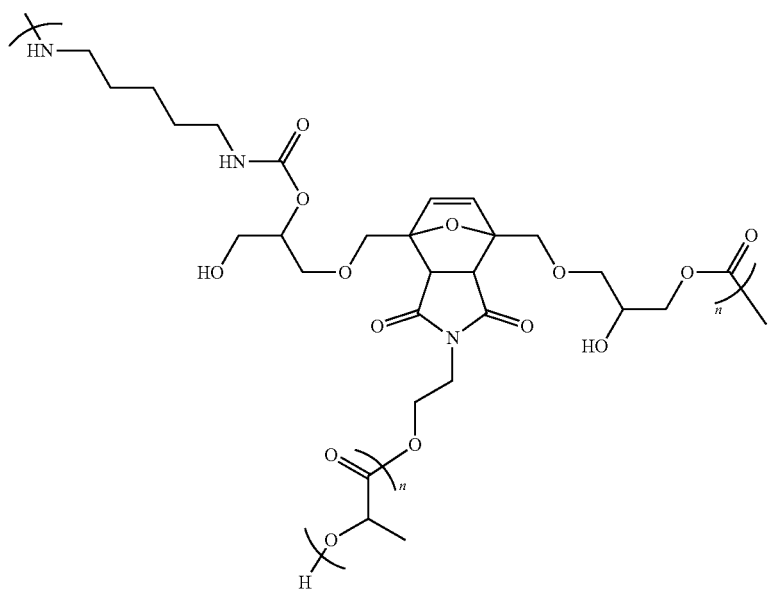

To a solution of a representative PHU based on FBC-2 and DAP (120 mg, 0.106 mmol based on mole of furan) in DMF (1 mL) was added PLA-M (90 mg, Mn~2000, 0.01 mmol based on mole of maleimide). The reaction mixture was stirred at 50° C. for 6 hours. After cooling to room temperature, the reaction mixture was added into diethyl ether to precipitate the polymer. The crude polymer was washed with ethyl acetate to remove the unreacted PLA-M. The purified polymer was obtained as white solid (85 mg, yield 40%). $^1$H NMR (400 MHz, DMSO) δ 7.11 (br, 2H), 6.37 (br, 2H), 6.34 (br, DA adduct peak), 5.21 (br, 2H), 5.01 (br, 1H), 4.81-4.68 (br, 1H), 4.38 (br, PLA peak), 3.92-3.74 (m, 5H), 3.51-3.21 (m, 8H), 2.93 (br, 4H), 1.47 (m, 6H), 1.36-1.10 (m, 8H).

APPLICATIONS

Various embodiments of the present disclosure provide a green and sustainable strategy to produce cyclic biscarbonates and polyhydroxyurethanes by using precursor compounds derived from a bio-based source. In various embodiments, the precursor compound, monomer and/or reaction product may be partially bio-based/bio-derived or fully bio-based/bio-derived. In various embodiments of the methods disclosed herein, the process does not involve the use of toxic isocyanates and phosgene, thereby making the production process friendly to the environment.

In various embodiments thereof, the compound (i.e. monomer) and reaction product (i.e. polymer) disclosed herein are high value products for specialty applications such as coating, foams and adhesives, which will not only further value-add bio-feedstocks supporting biorefineries but also provide alternative sustainable materials for future applications.

Various embodiments of the present disclosure provide non-isocyanate polyhydroxylurethanes (NIPUs/PHUs) having high thermal and hydrolytic stability, enhanced adhesion properties and are chemically resistant to non-polar solvents. Various embodiments of the present disclosure provide compounds that are capable of serving as monomers in a polymerization reaction and that comprise aromatic units that are atypical of cyclic biscarbonates known in the art. In various embodiments therefore, the reaction products of these monomers and polymers disclosed herein may be in the form of a new emerging class of functional isocyanate free polyurethanes and that can be used in a wide array of applications such as in the manufacturing of foams, solvent/water borne coating, adhesives in the building and construction, automotive, packaging, textiles, fibers, apparel, and electronics industry etc; in applications such as pigment/hydrophobic material dispersing agents, film formers, gelling agents, rheology modifiers, oil thickners etc; in personal care industry and in applications such as antifouling coating and drug delivery in biomedical industries. The present disclosure has demonstrated the principles involved, and opens the way for further scale-up in many applications.

It will be appreciated by a person skilled in the art that other variations and/or modifications may be made to the embodiments disclosed herein without departing from the spirit or scope of the disclosure as broadly described. For example, in the description herein, features of different exemplary embodiments may be mixed, combined, interchanged, incorporated, adopted, modified, included etc. or the like across different exemplary embodiments. The present embodiments are, therefore, to be considered in all respects to be illustrative and not restrictive.

The invention claimed is:

1. A compound represented by general formula (Ib):

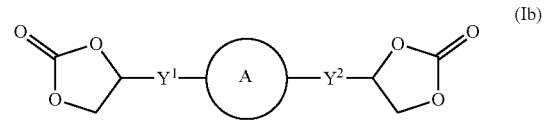

wherein
ring A is selected from the group consisting of thiophene, pyrrole, oxazole, isoxazole, isothiazole, tetrahydrofuran, tetrahydrothiophene, pyrrolidine, pyridine, pyrone, pyridazine, pyrimidine, pyrazine, triazine, piperidine and piperazine;
$Y^1$ and $Y^2$ are each independently selected from the group consisting of:
a single bond,
—Z—O—Z—,
—Z—NR$^b$—Z—,
—Z—O—C(=O)—Z—, —Z—C(=O)—O—Z—,
—Z—NR$^b$—C(=O)—Z—, —Z—C(=O)—NR$^b$—Z—,
—Z—NR$^b$—C(=O)—O—Z, Z—O—C(=O)—NR$^b$—Z—;
where each Z is independently selected from the group consisting of a single bond, optionally substituted saturated aliphatic chain and optionally substituted unsaturated aliphatic chain; and
where R$^b$ is H or $C_1$-$C_6$ alkyl.

2. The compound according to claim 1, wherein ring A is selected from any one of the general formulae (III) to (V):

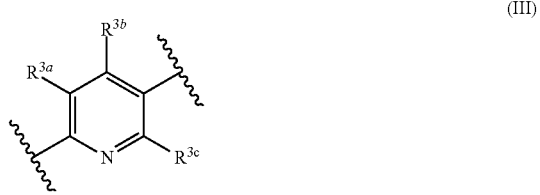

(III)

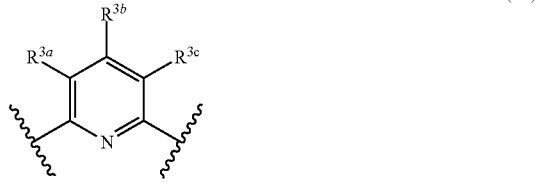

(IV)

(V)

wherein
$R^{3a}$, $R^{3b}$ and $R^{3c}$ are each independently selected from the group consisting of a hydrogen, hydroxy, halogen, cyano, amino, nitro, carboxyl, alkyl, alkenyl, alkynyl, alkoxy, haloalkyl, haloalkoxy, cycloalkyl, cycloalkenyl, alkylcarbonyl and alkoxycarbonyl.

3. The compound according to claim 1, wherein
$Y^1$ is selected from the group consisting of —Z—O—Z— and —Z—O—C(=O)—Z—;
$Y^2$ is selected from the group consisting of —Z—O—Z— and —Z—C(=O)—O—Z—;

each Z is independently selected from the group consisting of a single bond and $C_1$-$C_6$ alkyl.

4. The compound according to claim 1 selected from the following:

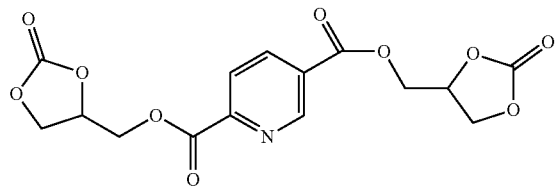 [SMILES: O=C1OCC(COC(=O)c2ccc(C(=O)OCC3COC(=O)O3)nc2)O1]

bis((2-oxo-1,3-dioxolan-4-yl)methyl)pyridine-2,5-dicarboxylate (PBC);

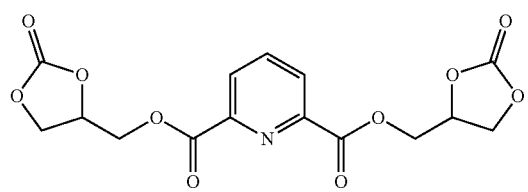 [SMILES: O=C1OCC(COC(=O)c2cccc(C(=O)OCC3COC(=O)O3)n2)O1]

bis((2-oxo-1,3-dioxolan-4-yl)methyl)pyridine-2,6-dicarboxylate (PBC-2); and

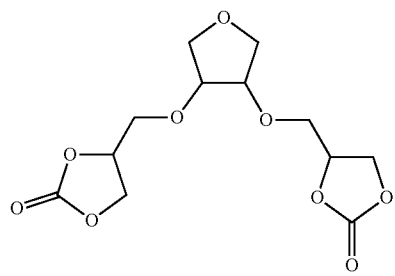 [SMILES: O=C1OCC(COC2COCC2OCC2COC(=O)O2)O1]

4,4'-(((tetrahydrofuran-3,4-diyl)bis(oxy))bis(methylene)) bis(1,3-dioxolan-2-one) (HFBC).

5. A method of preparing the compound according to claim 1, the method comprising:
converting a precursor compound represented by general formula (VI) to the compound of claim 1 through one or more chemical reactions:

(VI)

wherein
ring A is selected from the group consisting of disubstituted thiophene, disubstituted pyrrole, disubstituted oxazole, disubstituted isoxazole, disubstituted isothiazole, disubstituted tetrahydrofuran, disubstituted tetrahydrothiophene, disubstituted pyrrolidine, disubstituted pyridine, disubstituted pyrone, disubstituted pyridazine, disubstituted pyrimidine, disubstituted pyrazine, disubstituted triazine, disubstituted piperidine and disubstituted piperazine;
$R^4$ and $R^5$ are each independently selected from the group consisting of —OH, —C(=O)H, —C(=O)—OH, —NR$^c$R$^d$, —C(=O)—NR$^c$R$^d$, —($C_1$-$C_6$ alkyl)-OH, —($C_1$-$C_6$ alkyl)-C(=O)H, —($C_1$-$C_6$ alkyl)-C(=O)—OH, —($C_1$-$C_6$ alkyl)-NR$^c$R$^d$ and —($C_1$-$C_6$ alkyl)-C(=O)—NR$^c$R$^d$,
where R$^c$ and R$^d$ are independently selected from the group consisting of H or $C_1$-$C_6$ alkyl, and
wherein at least one of the one or more chemical reactions is carried out in the presence of a halogenated compound.

6. The method according to claim 5, wherein the precursor compound is selected from the group consisting of pyridine-2,5-dicarboxylic acid, pyridine-2,6-dicarboxylic acid and 1,4-anhydroerythritol.

7. A reaction product of the reaction between one or more compounds according to claim 1 and one or more amine containing compounds, the reaction product having hydroxyl groups and urethane/carbamate linkages.

8. The reaction product according to claim 7, wherein the reaction product is a polymer having a repeating unit represented by general formula (VIIb) or a derivative thereof:

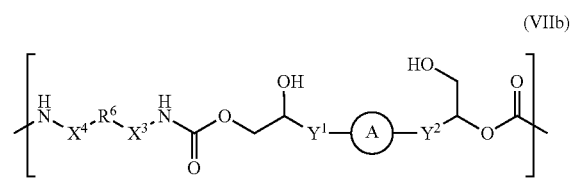

(VIIb)

wherein
ring A is selected from the group consisting of thiophene, pyrrole, oxazole, isoxazole, isothiazole, tetrahydrofuran, tetrahydrothiophene, pyrrolidine, pyridine, pyrone, pyridazine, pyrimidine, pyrazine, triazine, piperidine and piperazine;
$Y^1$ and $Y^2$ are each independently selected from the group consisting of:
a single bond,
—Z—O—Z—,
—Z—NR$^b$—Z—,
—Z—O—C(=O)—Z—, —Z—C(=O)—O—Z—,
—Z—NR$^b$—C(=O)—Z—, —Z—C(=O)—NR$^b$—Z—,
—Z—NR$^b$—C(=O)—O—Z, Z—O—C(=O)—NR$^b$—Z—;
where each Z is independently selected from the group consisting of a single bond, optionally substituted saturated aliphatic chain and optionally substituted unsaturated aliphatic chain;
where R$^b$ is H or $C_1$-$C_6$ alkyl;
$R^6$ is selected from the group consisting of optionally substituted alkyl, optionally substituted alkenyl, optionally substituted alkynyl, optionally substituted polyether, optionally substituted 5-membered or 6-membered hydrocarbon cyclic ring and an optionally substituted 5-membered or 6-membered heterocyclic ring having up to three heteroatoms independently selected from the group consisting of O, and S;
$X^3$ and $X^4$ are each independently selected from the group consisting of a single bond and —($C_1$-$C_6$ alkyl).

9. The reaction product according to claim 7, wherein ring A is selected from any one of the general formulae (III) to (V):

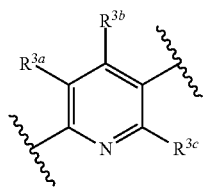

(III)

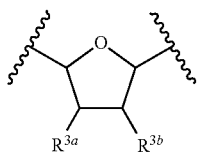

(V)

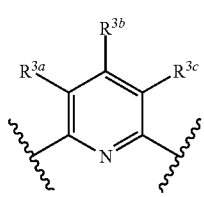

(IV)

wherein
R³ᵃ, R³ᵇ and R³ᶜ are each independently selected from the group consisting of a hydrogen, hydroxy, halogen, cyano, amino, nitro, carboxyl, alkyl, alkenyl, alkynyl, alkoxy, haloalkyl, haloalkoxy, cycloalkyl, cycloalkenyl, alkylcarbonyl and alkoxycarbonyl.

10. The reaction product according to claim 8, wherein
Y¹ is selected from the group consisting of —Z—O—Z— and —Z—O—C(=O)—Z—;
Y² is selected from the group consisting of —Z—O—Z— and —Z—C(=O)—O—Z—;
each Z is independently selected from the group consisting of a single bond and C₁-C₆ alkyl.

11. The reaction product according to claim 7 selected from the following:

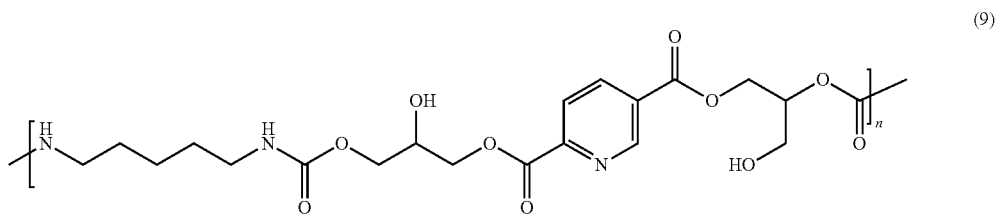

(9)

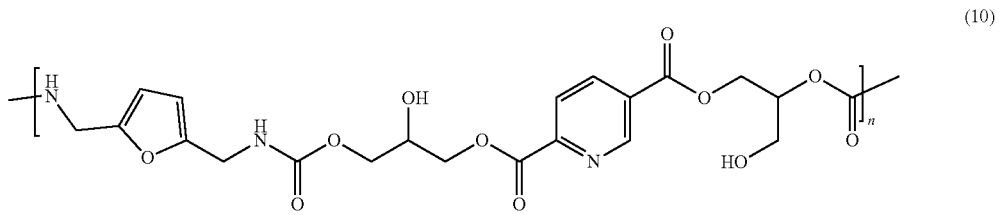

(10)

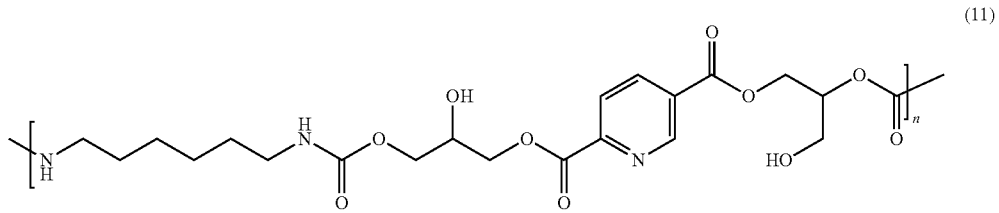

(11)

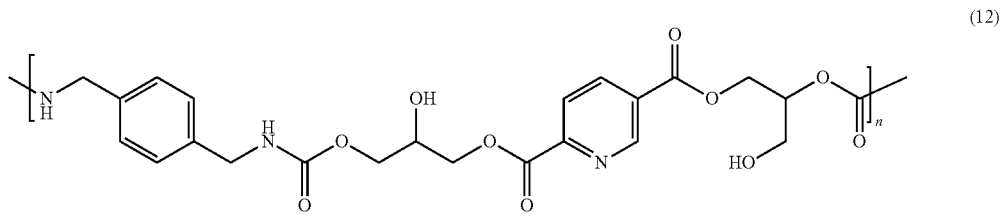

(12)

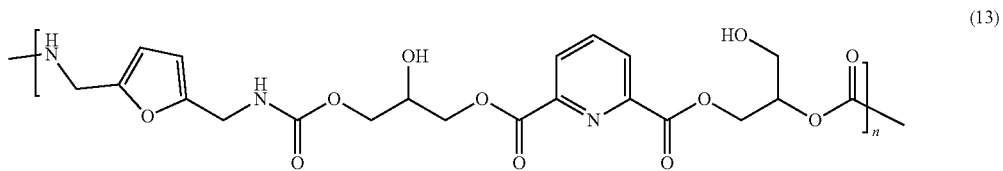

(13)

(14)
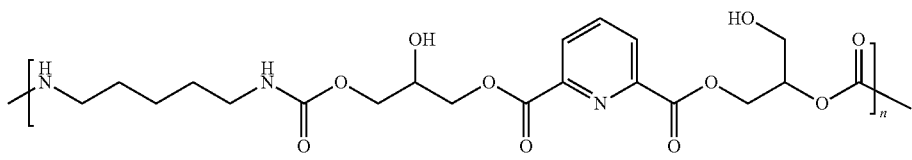
(15)
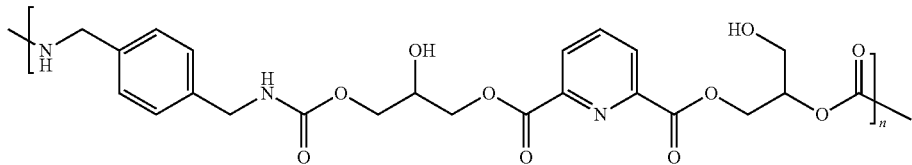
(16)
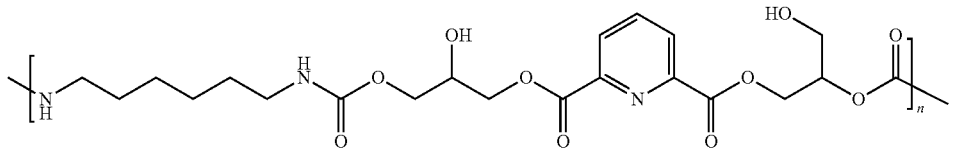
(17)
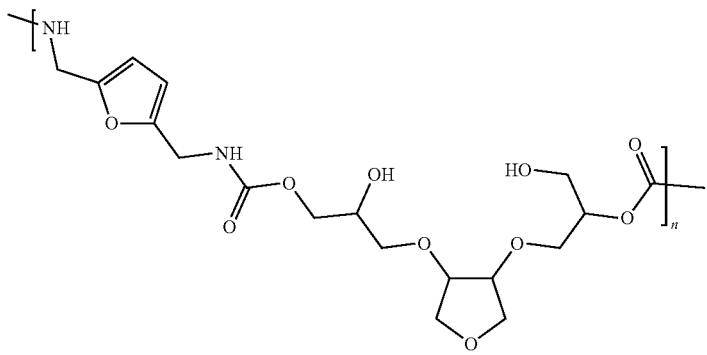
(18)
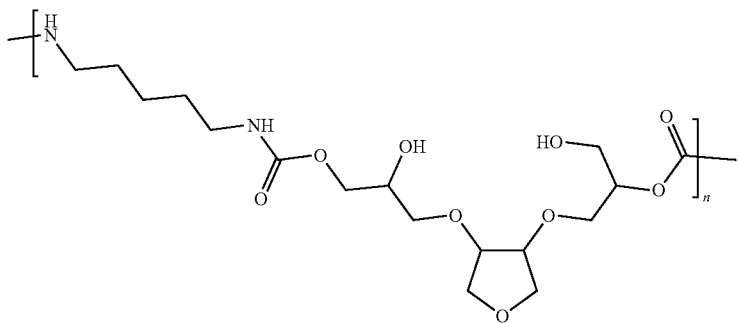
(19)
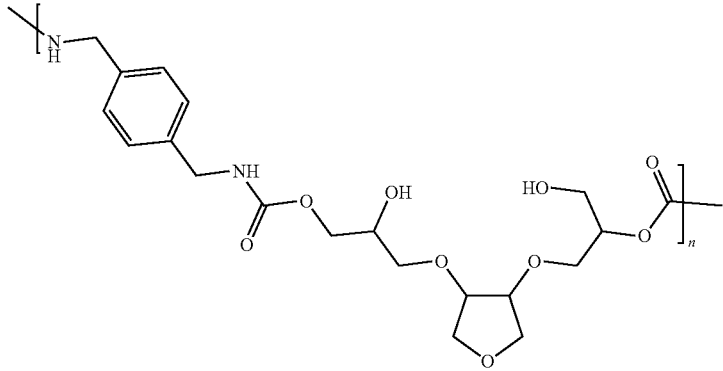

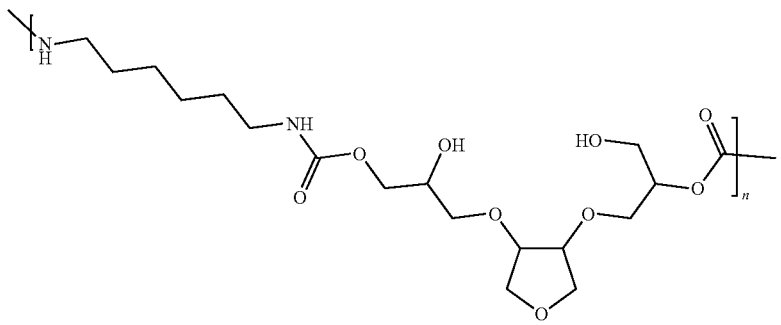

(20)

or a derivative thereof.

12. The reaction product according to claim 7, wherein the product has one or more of the following properties: number average molecular weight (Mn) in the range of 2,000 g/mol to 50,000 g/mol, peak molecular weight (Mp) in the range of 1,500 g/mol to 60,000 g/mol and the polydispersity index (PDI) is in the range of 1.0 to 5.0, wherein the number average molecular weight, peak molecular weight and polydispersity index are determined by gel permeation chromatography using polymethyl methacrylate (PMMA) calibration.

13. The reaction product according to claim 7, wherein the reaction product is a functionalised or grafted product having one or more of the following properties: solubility or dispersibility in water, solubility or dispersibility in oil, photo or thermo or redox or pH response and crosslinking ability under air, photo, thermal, redox or ionic conditions.

14. The reaction product according to claim 13, wherein the reaction product is a functionalised product obtained by reacting one or more compounds according to claim 1 with one or more amine containing compounds and further functionalising one or more hydroxyl groups present in the reaction product.

15. The reaction product according to claim 13, wherein the reaction product is a grafted product obtained by reacting one or more compounds according to claim 1 with one or more amine containing compounds and further grafting a polymer to one or more hydroxyl groups present in the reaction product.

16. The reaction product according to claim 13, wherein the reaction product is a grafted product obtained by reacting one or more compounds according to claim 1 with one or more amine containing compounds and further grafting one or more molecular entities or polymers to one or more furan rings present in the reaction product.

17. The reaction product according to claim 7, wherein the amine containing compound comprises at least two amine functional groups, optionally wherein the amine containing compound is selected from the group consisting of furan-2, 5-diyldimethanamine (FBA), xylene diamine (XDA), diaminopentane (DAP), hexamethylenediamine (HDA), ethylenediamine, diaminopropane, diaminobutane, ether diamine, polyether diamine, dimer diamine, lysine, isophorone diamine and phenylenediamine.

* * * * *